(12) United States Patent
Liu et al.

(10) Patent No.: US 6,399,773 B1
(45) Date of Patent: Jun. 4, 2002

(54) COMPOUNDS DERIVED FROM AN AMINE NUCLEUS THAT ARE INHIBITORS OF IMPDH ENZYME

(75) Inventors: Chunjian Liu, Trenton, NJ (US); T. G. Murali Dhar, Newtown, PA (US); Henry H. Gu, Bordentown, NJ (US); Edwin J. Iwanowicz, Cranbury, NJ (US); Katerina Leftheris, Skillman, NJ (US); William J. Pitts, Newtown, PA (US)

(73) Assignee: Bristol-Myers Squibb Co., Princeton, NJ (US)

( * ) Notice: Subject to any disclaimer, the term of this patent is extended or adjusted under 35 U.S.C. 154(b) by 0 days.

(21) Appl. No.: 09/428,432

(22) Filed: Oct. 27, 1999

Related U.S. Application Data

(60) Provisional application No. 60/106,186, filed on Oct. 29, 1998.

(51) Int. Cl.[7] .................... C07D 265/28; C07D 413/00; C07D 263/00; A61K 31/5355
(52) U.S. Cl. .................... 544/106; 544/111; 544/165; 514/231.5; 514/235.5; 514/236.5; 514/237.5; 548/233; 548/234
(58) Field of Search .................... 514/231.5, 235.5, 514/236.8, 237.8; 544/185, 106, 111; 548/233, 234

(56) References Cited

U.S. PATENT DOCUMENTS

| 4,686,234 A | 8/1987 | Nelson et al. ............... 514/469 |
| 4,725,622 A | 2/1988 | Nelson et al. ............... 514/469 |
| 4,727,069 A | 2/1988 | Nelson et al. ............... 514/211 |
| 4,753,935 A | 6/1988 | Nelson et al. ............... 514/233 |
| 4,786,637 A | 11/1988 | Allison et al. ............ 514/233.5 |
| 4,808,592 A | 2/1989 | Nelson et al. ............ 514/233.5 |
| 4,861,776 A | 8/1989 | Nelson et al. ............ 514/233.5 |
| 4,868,153 A | 9/1989 | Allison et al. .............. 514/470 |
| 4,948,793 A | 8/1990 | Allison et al. ........... 514/233.5 |
| 4,952,579 A | 8/1990 | Nelson et al. ............ 514/233.5 |
| 4,959,387 A | 9/1990 | Nelson et al. ............... 524/469 |
| 4,992,467 A | 2/1991 | Allison et al. .............. 514/464 |
| 5,247,083 A | 9/1993 | Knox et al. .................. 544/153 |
| 5,380,879 A | 1/1995 | Sjogren ....................... 549/310 |
| 5,444,072 A | 8/1995 | Patterson et al. ........... 514/320 |
| 5,665,583 A | 9/1997 | Collart et al. ............... 435/191 |
| 5,807,876 A | 9/1998 | Armistead et al. .......... 514/374 |

FOREIGN PATENT DOCUMENTS

| EP | 837063 | * 4/1998 |
| WO | WO94/01105 | 1/1994 |
| WO | WO94/12184 | 6/1994 |
| WO | WO97/40028 | 10/1997 |
| WO | WO98/40381 | 9/1998 |
| WO | WO99/55663 | 11/1999 |

OTHER PUBLICATIONS

Nature 256:331–333 (1975) Jackson et al.
J. Biol. Chem. 263:15769–15672 (1988) Collart et al.
J. Biol. Chem. 265:5292–5295 (1990) Natsumeda et al.
J. Biol. Chem. 266:506–509 (1991) Weber
J. Biol. Chem. 268:27286–27290 (1993) Carr.

\* cited by examiner

*Primary Examiner*—Mukund J. Shah
*Assistant Examiner*—Sudhaker B. Patel
(74) *Attorney, Agent, or Firm*—Audrey F. Sher; Anastasia P. Winslow

(57) ABSTRACT

The present invention discloses the identification of the novel inhibitors of IMPDH (inosine-5'-monophosphate dehydrogenase). The compounds and pharmaceutical compositions disclosed herein are useful in treating or preventing IMPDH mediated diseases, such as transplant rejection and autoimmune diseases.

26 Claims, No Drawings

COMPOUNDS DERIVED FROM AN AMINE NUCLEUS THAT ARE INHIBITORS OF IMPDH ENZYME

This application claims priority from provisional U.S. Application Ser. No. 60/106,186, filed Oct. 29, 1998, which is incorporated herein by reference in its entirety.

FIELD OF THE INVENTION

The present invention relates to novel compounds which inhibit IMPDH, and to methods of making such compounds. The invention also encompasses pharmaceutical compositions comprising these compounds. The compounds and pharmaceutical compositions of the invention are particularly well suited for inhibiting IMPDH enzyme activity and, consequently, may be advantageously used as therapeutic agents for IMPDH-associated disorders. This invention also relates to methods for inhibiting the activity of IMPDH using the compounds of this invention and related compounds.

BACKGROUND OF THE INVENTION

Inosine monophosphate dehydrogenase (IMPDH) has been shown to be a key enzyme in the regulation of cell proliferation and differentiation. Nucleotides are required for cells to divide and replicate. In mammals, nucleotides may be synthesized through one of two pathways: the de novo synthesis pathway or the salvage pathway. The extent of utilization of each pathway is dependent on the cell type. This selectivity has ramifications with regard to therapeutic utility as described below.

IMPDH is involved in the de novo synthesis of guanosine nucleotides. IMPDH catalyzes the irreversible NAD-dependent oxidation of inosine-5'-monophosphate ("IMP") to xanthosine-5'-monophosphate ("XMP"), Jackson et al., *Nature* 256:331–333 (1975).

IMPDH is ubiquitous in eukaryotes, bacteria and protozoa. The prokaryotic forms share 30–40% sequence identity with the human enzyme.

Two distinct cDNA's encoding IMPDH have been identified and isolated. These transcripts are labeled type I and type II and are of identical size (514 amino acids). Collart et al., *J. Biol. Chem.* 263:15769–15772 (1988); Natsumeda et al., *J. Biol. Chem.* 265:5292–5295 (1990); and U.S. Pat. No. 5,665,583 to Collart et al. These isoforms share 84% sequence identity. IMPDH type I and type II form tetramers in solution, the enzymatically active unit.

B and T-lymphocytes depend on the de novo, rather than salvage pathway, to generate sufficient levels of nucleotides necessary to initiate a proliferative response to mitogen or antigen. Due to the B and T cell's unique reliance on the de novo pathway, IMPDH is an attractive target for selectively inhibiting the immune system without also inhibiting the proliferation of other cells.

Immunosuppression has been achieved by inhibiting a variety of enzymes. Examples include: phosphatase calcineurin (inhibited by cyclosporin and FK-506); dihydroorotate dehydrogenase (DHODase), an enzyme involved in the biosynthesis of pyrimidines (inhibited by leflunomide and brequinar); the kinase FRAP (inhibited by rapamycin); and the heat shock protein hsp70 (inhibited by deoxyspergualin).

Inhibitors of IMPDH have also been described in the art. WO 97/40028 and U.S. Pat. No. 5,807,876 describe a class of urea derivatives that possess a common urea backbone. A large number of compounds are described in WO 97/40028 and U.S. Pat. No. 5,807,876, but several of the compounds suffer from drawbacks such as inferior solubility. A recent publication, WO 98/40381, describes a series of heterocyclic substituted anilines as inhibitors of IMPDH.

U.S. Pat. Nos. 5,380,879 and 5,444,072 and PCT publications WO 94/01105 and WO 94/12184 describe mycophenolic acid ("MPA") and some of its derivatives as potent, uncompetitive, reversible inhibitors of human IMPDH type I and type II. MPA has been demonstrated to block the response of B and T-cells to mitogen or antigen. Immunosuppressants, such as MPA and derivatives of MPA, are useful drugs in the treatment of transplant rejection and autoimmune disorders, psoriasis, inflammatory diseases, including, rheumatoid arthritis, tumors and for the treatment of allograft rejection. These are described in U.S. Pat. Nos. 4,686234, 4,725622, 4,727,069, 4,753,935, 4,786,637, 4,808,592, 4,861,776, 4,868,153, 4,948,793, 4,952,579, 4,959,387, 4,992,467; 5.247,083; and U.S. patent application Ser. No. 07/927,260, filed Aug. 7, 1992. MPA does display undesirable pharmacological properties, such as gastrointestinal toxicity and poor bioavailability.

Tiazofurin, ribavirin and mizoribine also inhibit IMPDH. These nucleoside analogs are competitive inhibitors of IMPDH, however these agents inhibit other NAD dependent enzymes. This low level of selectivity for IMPDH limits the therapeutic application of tiazofurin, ribavirin and mizoribine. Thus, new agents which have improved selectivity for IMPDH would represent a significant improvement over the nucleoside analogs.

Mycophenolate mofetil, sold under the trade name CELLCEPT, is a prodrug which liberates MPA in vivo. It is approved for use in preventing acute renal allograft rejection following kidney transplantation. The side effect profile limits the therapeutic potential of this drug. MPA is rapidly metabolized to the inactive glucuronide in vivo. In humans, the blood levels of glucuronide exceed that of MPA. The glucuronide undergoes enterohepatic recycling causing accumulation of MPA in the bile and subsequently in the gastrointestinal tract. This together with the production of the inactive glucuronide effectively lowers the drug's in vivo potency, while increasing its undesirable gastrointestinal side effects.

Unlike type I, type II mRNA is preferentially upregulated in human leukemic cell lines K562 and HL-60. Weber, J. Biol. Chem. 266: 506–509 (1991). In addition, cells from human ovarian tumors and leukemic cells from patients with chronic granulocytic, lymphocytic and acute myeloid leukemias also display an up regulation type II mRNA. This disproportionate increase in IMPDH activity in malignant cells may be addressed through the use of an appropriate IMPDH inhibitor. IMPDH has also been shown to play a role in the proliferation of smooth muscle cells, indicating that inhibitors of IMPDH may be useful in preventing restenosis or other hyperproliferative vascular diseases.

IMPDH has been shown to play a role in viral replication in some viral cell lines. Carr, *J. Biol. Chem.* 268:27286–27290 (1993). The IMPDH inhibitor VX-497, is currently being evaluated for the treatment of hepatitis C virus in humans. Ribavirin has also been used in the treatment of hepatitis C and B viruses and when used in combination with interferon an enhancement in activity was observed. The IMPDH inhibitor ribavirin is limited by its lack of a sustained response in monotherapy and broad cellular toxicity.

There remains a need for potent selective inhibitors of IMPDH with improved pharmacological properties, physical properties and fewer side effects. Such inhibitors would have therapeutic potential as immunosuppressants, anti-cancer agents, anti-vascular hyperproliferative agents, anti-inflammatory agents, antifungal agents, antipsoriatic and anti-viral agents. The compounds of the present invention differ from those taught by the prior art and are effective inhibitors of IMPDH.

SUMMARY OF THE INVENTION

The present invention provides heterocyclic compounds of the following formula (I), their enantiomers, diastereomers, tautomers and pharmaceutically acceptable salts, prodrugs and solvates thereof, for use as IMPDH inhibitors:

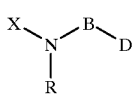

(I)

wherein:

X is a monocyclic or bicyclic ring system optionally containing up to 4 heteroatoms selected from N, O, and S, and wherein a $CH_2$ adjacent to any of the said N, O or S heteroatoms is optionally substituted with oxo (=O), and wherein X is optionally substituted by 0–5 substituents chosen from A, $R^1$, or $R^2$;

A is $R^3$ or $R^4$;

$R^3$ is a 5- or 6-membered heterocyclic ring system containing up to 4 heteroatoms selected from N, O, and S, said heterocyclic ring system being optionally substituted with 0–3 $R^5$, wherein when $R^5$ is hydroxy, the heterocycle may undergo tautomerization to an oxo species, or exist as an equilibrium mixture of both tautomers;

$R^4$ is selected from H, F, Cl, Br, I, $NO_2$, $CF_3$, $C_0$–$C_4$ alkylCN, $C_1$–$C_4$alkoxy-, $C_0$–$C_4$ alkylhydroxy, $C_1$–$C_4$ alkyl-, $C_1$–$C_4$ alkylcarbonyl-, $C_0$–$C_4$ alkylOCOR$^6$, $C_0$–$C_4$ alkylOC(=O)OR$^6$, $C_0$–$C_4$ alkylOC(=O)NR$^6$R$^7$, $NH_2$, NHR$^6$, $C_0$–$C_4$ alkylNR$^6$R$^7$, $C_0$–$C_4$ alkylNR$^7$C(=O)OR$^6$, $C_0$–$C_4$ alkylNR$^6$SO$_2$NR$^6$R$^7$, $C_0$–$C_4$ alkylNR$^7$SO$_2$R$^6$, $C_0$–$C_4$ alkylSR$^6$, $C_0$–$C_4$ alkylS(O)R$^6$, $C_0$–$C_4$ alkylSO$_2$R$^6$, SO$_3$R$^7$, $C_0$–$C_4$ alkylSO$_2$NR$^6$R$^7$, $C_0$–$C_4$alkyl SO$_2$NR$^7$ CO(CR$^9$R$^{10}$)$_q$ R$^6$, $C_0$–$C_4$ alkylCO$_2$H, $C_0$–$C_4$ alkylCO$_2$R$^6$, $C_0$–$C_4$ alkylCONR$^6$R$^7$, and $C_0$–$C_4$CONR$^7$SO$_2$(CR$^9$R$^{10}$)$_q$R$^6$;

$R^5$ is selected from H, halogen, $NO_2$, $C_1$–$C_4$alkyl, $C_3$–$C_{10}$cycloalkyl, $C_2$–$C_6$alkenyl, $C_2$–$C_6$alkynyl, haloalkyl, haloalkoxy, OH, oxo, $C_1$–$C_4$alkoxy, $C_1$–$C_4$alkylcarbonyl, CN, $NH_2$, NHR$^6$, NR$^6$R$^7$, SR$^7$, S(O)R$^7$, SO$_2$R$^7$, SO$_3$R$^7$, SO$_2$NR$^6$, CO$_2$H, CO$_2$R$^6$, and CONR$^6$R$^7$;

R is H or $C_1$–$C_4$alkyl;

$R^1$ and $R^2$ are each independently selected from H, halogen, $NO_2$, $C_1$–$C_4$alkyl, $C_3$–$C_{10}$cycloalkyl, $C_2$–$C_6$alkenyl, $C_2$–$C_6$alkynyl, haloalkyl, haloalkoxy, OH, $C_1$–$C_4$alkoxy-, OR$^6$, O(CR$^9$R$^{10}$)$_r$CO$_2$R$^6$, O(CR$^9$R$^{10}$)$_m$ NR$^6$R$^7$, O(CR$^9$R$^{10}$)$_p$CN, O(CR$^9$R$^{10}$)$_r$C (=O)NR$^6$R$^7$, $C_1$–$C_4$alkylcarbonyl-, CN, $NH_2$, NHR$^6$, NR$^6$R$^7$, NR$^7$(CR$^9$R$^{10}$)$_r$CO$_2$R$^6$, NR$^7$OR$^6$, NR$^7$ (CR$^9$R$^{10}$)$_m$OR$^6$, NR$^7$CH[(CR$^9$R$^{10}$)$_p$OR$^6$]$_2$, NR$^7$C [(CR$^9$R$^{10}$)$_p$OR$^6$]$_3$, NR$^7$C(=O)R$^6$, NR$^7$(CR$^9$R$^{10}$)$_m$ OR$^6$, NR$^7$(CR$^9$R$^{10}$)$_m$NR$^6$R$^7$, NR$^7$(CR$^9$R$^{10}$)$_m$SO$_2$ (CR$^9$R$^{10}$)$_q$R, SR$^7$, S(O)R$^7$, SO$_2$R$^7$, SO$_2$NR$^6$, SO$_3$R$^7$, SO$_2$NR$^6$, CO$_2$H, CO$_2$R$^6$, and CONR$^6$R$^7$; or, alternatively, $R^1$ and $R^2$, when on adjacent carbon atoms, may be taken together to be methylenedioxy or ethylenedioxy;

$R^6$, $R^7$ and $R^8$ are each independently selected from H, $C_1$–$C_6$alkyl, $C_3$–$C_{10}$ cycloalkyl, $C_2$–$C_6$alkenyl, $C_2$–$C_6$alkynyl, $C_1$–$C_6$ alkylcarbonyl, $C_3$–$C_7$ cycloalkyl ($C_1$–$C_5$ alkyl)carbonyl, $C_1$–$C_6$ alkoxycarbonyl, aryl ($C_0$–$C_5$ alkyl)carbonyl, aryl($C_1$–$C_5$ alkyloxy)carbonyl, heterocyclic($C_0$–$C_5$ alkyl)carbonyl, heterocyclic ($C_1$–$C_5$ alkoxy)carbonyl, $C_1$–$C_6$alkylsulfonyl, aryllsulfonyl, heteroarylsulfonyl, $C_0$–$C_4$alkylaryl, $C_0$–$C_4$alkylheterocyclic, wherein said cycloalkyl, aryl or heterocyclic groups are substituted with 0–2 substituents independently selected from the group consisting of $C_1$–$C_4$alkyl, hydroxy, $C_1$–$C_4$ alkoxy, F, Cl, Br, haloalkyl, $NO_2$ and CN;

or, alternatively, $R^6$ and $R^7$, or $R^6$ and $R^8$, or $R^7$ and $R^8$, when both substituents are on the same nitrogen atom [as in (—NR$^6$R$^7$) or (—NR$^7$R$^8$)], can be taken together with the nitrogen atom to which they are attached to form a heterocycle selected from 1-aziridinyl, 1-azetidinyl, 1-piperidinyl, 1-morpholinyl, 1-pyrrolidinyl, thiamorpholinyl, thiazolidinyl, 1-piperazinyl, 1-imidazolyl, 3-azabicyclo[3,2,2]nonan-3-yl, and 1-tetrazolyl, the said heterocycle being optionally substituted with 0–3 groups selected from oxo, $C_0$–$C_4$alkylOH, $C_0$–$C_4$alkylOC$_1$–$C_4$alkyl, $C_0$–$C_4$alkylCONH$_2$, $C_0$–$C_4$alkylCO$_2$C$_0$–$C_4$alkyl, $C_1$–$C_6$ alkyl, $C_1$–$C_4$ alkoxy, $C_3$–$C_7$ cycloalkyl, —$C_0$–$C_6$ alkylcarbonyl, $C_3$–$C_7$ cycloalkylcarbonyl, $C_1$–$C_6$ alkoxycarbonyl, $C_3$–$C_7$ cycloalkoxycarbonyl, —NHCOalkyl, aryl, heteroaryl, aryl alkoxycarbonyl, heteroaryl alkoxycarbonyl, $C_1$–$C_6$ alkylsulfonyl, arylsulfonyl and heteroarylsulfonyl;

B is a monocyclic or bicyclic ring system optionally containing up to 4 heteroatoms selected from N, O, and S, and wherein a $CH_2$ adjacent to any of the said N, O or S heteroatoms is optionally substituted with oxo (=O), and wherein B is optionally substituted by one to four $R^{11}$ groups;

D is a monocyclic or bicyclic ring system optionally containing up to 4 heteroatoms selected from N, O, and S, and wherein a $CH_2$ adjacent to any of the said N, O or S heteroatoms is optionally substituted with oxo (=O), and wherein D is optionally substituted by one to four (CR$^9$R$^{10}$)$_n$ E groups;

n is an integer having a value from 0–4;

m is an integer having a value from 2–6;

p is an integer having a value from 1–3;

q is an integer having a value from 0–3;

r is an integer having a value from 0–6;

$R^9$ is H or $C_1$–$C_4$alkyl;

$R^{10}$ is selected from H or $C_1$–$C_4$ alkyl, $C_1$–$C_4$ alkylhydroxy, $C_1$–$C_4$alkylaryl or $C_1$–$C_4$alkylheteroaryl, wherein said aryl or heteroaryl group may be substituted with 0–3 groups independently selected from H, halogen, $NO_2$, $C_1$–$C_4$alkyl, $C_3$–$C_{10}$cycloalkyl, $C_2$–$C_6$alkenyl, $C_2$–$C_6$alkynyl, haloalkyl, haloalkoxy, OH, $C_1$–$C_4$alkoxy, $C_1$–$C_4$alkylcarbonyl, CN, $NH_2$, NR$^6$R$^7$, SR$^6$, S(O)R$^6$, SO$_2$R$^6$, SO$_3$R$^6$, SO$_2$NR$^6$, CO$_2$H, CO$_2$R$^6$, and CONR$^6$R$^7$;

$R^{11}$ is selected from H, halogen, $NO_2$, $C_1$–$C_4$alkyl, $C_3$–$C_{10}$cycloalkyl, $C_2$–$C_6$alkenyl, $C_2$–$C_6$alkynyl, haloalkyl, haloalkoxy, OH, $C_1$–$C_4$alkoxy-, OR$^6$, O(CR$^9$R$^{10}$)$_r$CO$_2$R$^6$, O(CR$^9$R$^{10}$)$_m$NR$^6$R$^7$, O(CR$^9$R$^{10}$)$_p$ CN, O(CR$^9$R$^{10}$)$_r$C(=O)NR$^6$R$^7$, C$_1$–C$_4$alkylcarbonyl-, CN, NH$_2$, NHR$^6$, NR$^6$R$^7$, NR$^7$(CR$^9$R$^{10}$)$_r$CO$_2$R$^6$, NR$^7$OR$^6$, NR$^7$(CR$^9$R$^{10}$)$_m$OR$^6$, NR$^7$CH[(CR$^9$R$^{10}$)$_p$OR$^6$]$_2$, NR$^7$C[(CR$^9$R$^{10}$)$_p$OR$^6$]$_3$, NR$^7$C(=O)R$^6$, NR$^7$(CR$^9$R$^{10}$)$_m$OR$^6$, NR$^7$(CR$^9$R$^{10}$)$_m$NR$^6$R$^7$, NR$^7$(CR$^9$R$^{10}$)$_m$SO$_2$(CR$^9$R$^{10}$)$_q$R$^6$, SR$^7$, S(O)R$^7$, SO$_2$R$^7$, SO$_2$NR$^6$, SO$_3$R$^7$, CO$_2$H, CO$_2$R$^6$, and CONR$^6$R$^7$;

E is selected from H, halogen, NO$_2$, C$_1$–C$_4$alkyl, C$_3$–C$_{10}$cycloalkyl, C$_2$–C$_6$ alkenyl, C$_2$–C$_6$ alkynyl, haloalkyl, haloalkoxy, OH, OR$^6$, CN, CHO, CO$_2$R$^6$, CONR$^6$R$^7$, OCOR$^6$, OC(=O)OR$^6$, OC(=O)NR$^6$R$^7$, OCH$_2$CO$_2$R$^6$, C(=O)R$^6$, NH$_2$, NHR$^6$, NR$^6$R$^7$, NR$^7$C(=O)R$^6$, NR$^7$C(=O)OR$^6$, NR$^7$C(=O)C(=O)OR$^6$, NR$^7$C(=O)C(=O)NR$^6$R$^7$, NR$^7$C(=O)C(=O)(C$_1$–C$_6$alkyl), NR$^7$C(=NCN)OR$^6$, NR$^7$C(=O)NR$^6$R$^7$, NR$^7$C(=NCN)NR$^6$R$^7$, NR$^7$C(=NR$^6$)NR$^7$R$^8$, NR$^6$SO$_2$NR$^6$R$^7$, NR$^7$SO$_2$R$^6$, SR$^6$, S(=O)R$^6$, SO$_2$R$^6$, SO$_3$R$^7$, SO$_2$NR$^6$R$^7$, NHOH, NHOR$^6$, NR$^6$NR$^7$NR$^8$, N(COR$^6$)OH, N(CO$_2$R$^6$)OH, CO$_2$R$^6$, CONR$^6$R$^7$, CONR$^7$(CR$^9$R$^{10}$)$_r$R$^6$, CO(CR$^9$R$^{10}$)$_p$O(CHR$^9$)$_q$CO$_2$R$^6$, CO(CR$^9$R$^{10}$)$_r$OR$^6$, CO(CR$^9$R$^{10}$)$_p$O(CR$^9$R$^{10}$)$_q$R$^6$, CO(CR$^9$CR$^{10}$)$_r$NR$^6$R$^7$,OC(O)O(CR$^9$R$^{10}$)$_m$NR$^6$R$^7$, O(CO)N(CR$^9$R$^{10}$)$_r$R$^6$, O(CR$^9$R$^{10}$)$_m$NR$^6$R$^7$, NR$^7$C(O)(CR$^9$R$^{10}$)$_r$R$^6$, NR$^7$C(O)(CR$^9$R$^{10}$)$_r$OR$^6$, NR$^7$C(=NC)(CR$^9$R$^{10}$)$_r$OR$^6$, NR$^7$C(=NC)(CR$^9$R$^{10}$)$_r$R$^6$, NR$^7$CO(CR$^9$R$^{10}$)$_r$NR$^6$R$^7$, NR$^7$(CR$^9$R$^{10}$)$_m$OR$^6$, NR$^7$(CR$^9$R$^{10}$)$_r$CO$_2$R$^6$, NR$^7$(CR$^9$R$^{10}$)$_m$NR$^6$R$^7$, NR$^7$(CR$^9$R$^{10}$)$_n$SO$_2$(CR$^9$R$^{10}$)$_q$R$^6$, CONR$^7$(CR$^9$R$^{10}$)$_n$SO$_2$(CR$^9$R$^{10}$)$_q$, SO$_2$NR$^7$(CR$^9$R$^{10}$)$_n$CO(CR$^9$R$^{10}$)$_q$R$^6$, SO$_2$NR$^6$(CR$^9$R$^{10}$)$_m$OR$^6$, C$_2$–C$_6$ alkenyl, C$_3$–C$_{10}$ cycloalkyl, C$_3$–C$_{10}$ cycloalkylmethyl, aryl, heterocyclic and alkylaryl, wherein said aryl groups may be substituted with 0–2 substituents independently selected R$^{12}$;

R$^{12}$ at each occurence are independently selected from H, halogen, NO$_2$, C$_1$–C$_4$alkyl, C$_3$–C$_{10}$cycloalkyl, C$_2$–C$_6$alkenyl, C$_2$–C$_6$alkynyl, haloalkyl, haloalkoxy, OH, oxo, C$_1$–C$_4$alkoxy-, OR$^6$, O(CR$^9$R$^{10}$)$_r$CO$_2$R$^6$, O(CR$^9$R$^{10}$)$_m$NR$^6$R$^7$, O(CR$^9$R$^{10}$)$_p$CN, O(CR$^9$R$^{10}$)$_r$C(=O)NR$^6$R$^7$, C$_1$–C$_4$alkylcarbonyl-, CN, NH$_2$, NHR$^6$, NR$^6$R$^7$, NR$^7$(CR$^9$R$^{10}$)$_r$CO$_2$R$^6$, NR$^7$OR$^6$, NR$^7$(CR$^9$R$^{10}$)$_m$OR$^6$, NR$^7$CH[(CR$^9$R$^{10}$)$_p$OR$^6$]$_2$, NR$^7$C[(CR$^9$R$^{10}$)$_p$OR$^6$]$_3$, NR$^7$C(=O)R$^6$, NR$^7$(CR$^9$R$^{10}$)$_m$OR$^6$, NR$^7$(CR$^9$R$^{10}$)$_m$NR$^6$R$^7$, NR$^7$(CR$^9$R$^{10}$)$_m$SO$_2$(CR$^9$R$^{10}$)$_q$R$^6$, SR$^7$, S(O)R$^7$, SO$_2$R$^7$, SO$_2$NR$^6$, SO$_3$R$^7$, CO$_2$H, CO$_2$R$^6$, and CONR$^6$R$^7$.

Compounds of formula I, their enantiomers, diasteromers, tautomers and pharmaceutically acceptable salts, prodrugs and solvates thereof, are novel.

The present invention also provides pharmaceutical compositions comprising the compounds of formula I and methods of treating IMPDH-associated disorders using the compounds of formula I.

The compounds of the present invention offer therapeutic advantages over known prior art compounds, and are useful in treating IMPDH-associated disorders. These advantages include increased solubility (which in turn increases overall therapeutic benefit) and reduction in negative side effects.

DETAILED DESCRIPTION OF THE INVENTION

As described above, the present invention encompasses compounds of the following formula I, and salts thereof, for use as IMPDH inhibitors:

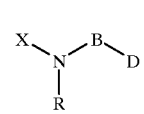

(I)

X is a monocyclic or bicyclic ring system optionally containing up to 4 heteroatoms selected from N, O, and S, and wherein a CH$_2$ adjacent to any of the said N, O or S heteroatoms is optionally substituted with oxo (=O), and wherein X is optionally substituted by 0–3 substituents chosen from A, R$^1$, or R$^2$;

A is R$^3$or R$^4$;

R$^3$ is a 5- or 6-membered heterocyclic ring system containing up to 4 heteroatoms selected from N, O, and S, said heterocyclic ring system being optionally substituted with 0–3 R$^5$, wherein when R$^5$ is hydroxy, the heterocycle may undergo tautomerization to an oxo species, or exist as an equilibrium mixture of both tautomers;

R$^4$ is selected from H, F, Cl, Br, I, NO$_2$, CF$_3$, C$_0$–C$_4$ alkylCN, C$_1$–C$_4$alkoxy-, C$_0$–C$_4$ alkylhydroxy, C$_1$–C$_4$ alkyl-, C$_1$–C$_4$ alkylcarbonyl-, C$_0$–C$_4$ alkylOCOR$^6$, C$_0$–C$_4$ alkylOC(=O)OR$^6$, C$_0$–C$_4$ alkylOC(=O)NR$^6$R$^7$, NH$_2$, NHR$^6$, C$_0$–C$_4$ alkylNR$^6$R$^7$, C$_0$–C$_4$ alkylNR$^7$C(=O)OR$^6$, C$_0$–C$_4$ alkylNR$^6$SO$_2$NR$^6$R$^7$, C$_0$–C$_4$ alkylNR$^7$SO$_2$R$^6$, C$_0$–C$_4$ alkylSR$^6$, C$_0$–C$_4$ alkylS(O)R$^6$, C$_0$–C$_4$ alkylSO$_2$R$^6$, SO$_3$R$^7$, C$_0$–C$_4$ alkylSO$_2$NR$^6$R$^7$, C$_0$–C$_4$alkylSO$_2$NR$^7$CO(CR$^9$R$^{10}$)$_q$R$^6$, C$_0$–C$_4$ alkylCO$_2$H, C$_0$–C$_4$ alkylCO$_2$R$^6$, C$_0$–C$_4$ alkylCONR$^6$R$^7$, and C$_0$–C$_4$CONR$^7$SO$_2$(CR$^9$R$^{10}$)$_q$R$^6$;

R$^5$ is selected from H, halogen, NO$_2$, C$_1$–C$_4$alkyl, C$_3$–C$_{10}$cycloalkyl, C$_2$–C$_6$alkenyl, C$_2$–C$_6$alkynyl, haloalkyl, haloalkoxy, OH, C$_1$–C$_4$alkoxy, C$_1$–C$_4$alkylcarbonyl, CN, NH$_2$, NHR$^6$, NR$^6$R$^7$, SR$^7$, S(O)R$^7$, SO$_2$R$^7$, SO$_3$R$^7$, SO$_2$NR$^6$, CO$_2$H, CO$_2$R$^6$, and CONR$^6$R$^7$;

R is H or C$_1$–C$_4$alkyl;

R$^1$ and R$^2$ are each independently selected from H, halogen, NO$_2$, C$_1$–C$_4$alkyl, C$_3$–C$_{10}$ cycloalkyl, C$_2$–C$_6$alkenyl, C$_2$–C$_6$alkynyl, haloalkyl, haloalkoxy, OH, C$_1$–C$_4$alkoxy-, OR$^6$, O(CR$^9$R$^{10}$)$_r$CO$_2$R$^6$, O(CR$^9$R$^{10}$)$_m$NR$^6$R$^7$, O(CR$^9$R$^{10}$)$_p$CN, O(CR$^9$R$^{10}$)$_r$C(=O)NR$^6$R$^7$, C$_1$–C$_4$alkylcarbonyl-, CN, NH$_2$, NHR$^6$, NR$^6$R$^7$, NR$^7$(CR$^9$R$^{10}$)$_r$CO$_2$R$^6$, NR$^7$OR$^6$, NR$^7$(CR$^9$R$^{10}$)$_m$OR$^6$, NR$^7$CH[(CR$^9$R$^{10}$)$_p$OR$^6$]$_2$, NR$^7$C[(CR$^9$R$^{10}$)$_p$OR$^6$]$_3$, NR$^7$C(=O)R$^6$, NR$^7$(CR$^9$R$^{10}$)$_m$OR$^6$, NR$^7$(CR$^9$R$^{10}$)$_m$NR$^6$R$^7$, NR$^7$(CR$^9$R$^{10}$)$_m$SO$_2$(CR$^9$R$^{10}$)$_q$R$^6$, SR$^7$, S(O)R$^7$, SO$_2$R$^7$, SO$_2$NR$^6$, SO$_3$R$^7$, CO$_2$H, CO$_2$R$^6$, and CONR$^6$R$^7$; or, alternatively, R$^1$ and R$^2$, when on adjacent carbon atoms, maybe taken together to be methylenedioxy or ethylenedioxy;

R$^6$, R$^7$ and R$^8$ are each independently selected from H, C$_1$–C$_6$alkyl, C$_3$–C$_{10}$ cycloalkyl, C$_2$–C$_6$alkenyl, C$_2$–C$_6$alkynyl, C$_1$–C$_6$ alkylcarbonyl, C$_3$–C$_7$ cycloalkyl (C$_0$–C$_5$ alkyl)carbonyl, C$_1$–C$_6$ alkoxycarbonyl, aryl (C$_0$–C$_5$ alkyl)carbonyl, aryl(C$_1$–C$_5$ alkoxy)carbonyl heterocyclic(C$_0$–C$_5$ alkyl)carbonyl, heterocyclic (C$_1$–C$_5$ alkoxy)carbonyl, C$_1$–C$_6$alkylsulfonyl, aryllsulfonyl, heteroarylsulfonyl, C$_0$–C$_4$alkylaryl, C$_0$–C$_4$alkylheterocyclic, wherein said cycloalkyl, aryl or heterocyclic groups are substituted with 0–2 substituents independently selected from the group consisting of C$_1$–C$_4$alkyl, hydroxy, C$_1$–C$_4$ alkoxy, F, Cl, Br, haloalkyl, NO$_2$ and CN;

or, alternatively, $R^6$ and $R^7$, or $R^6$ and $R^8$, or $R^7$ and $R^8$, when both substituents are on the same nitrogen atom [as in (—$NR^6R^7$) or (—$NR^7R^8$)], can be taken together with the nitrogen atom to which they are attached to form a heterocycle selected from 1-aziridinyl, 1-azetidinyl, 1-piperidinyl, 1-morpholinyl, 1-pyrrolidinyl, thiamorpholinyl, thiazolidinyl, 1-piperazinyl, 1-imidazolyl, 3-azabicyclo[3,2,2]nonan-3-yl, and 1-tetrazolyl, the said heterocycle being optionally substituted with 0–3 groups selected from oxo, $C_0$–$C_4$alkylOH, $C_0$–$C_4$alkylO$C_1$–$C_4$alkylCON$H_2$, $C_0$–C4alkylC$O_2$alkylC0–$C_4$, $C_1$–$C_6$ alkyl, $C_1$–$C_4$ alkoxy, $C_3$–$C_7$ cycloalkyl, —$C_0$–$C_6$ alkylcarbonyl, $C_3$–$C_7$ cycloalkylcarbonyl, $C_1$–$C_6$ alkoxycarbonyl, $C_3$–$C_7$ cycloalkoxycarbonyl, —NHCOalkyl, aryl, heteroaryl, aryl alkoxycarbonyl, heteroaryl alkoxycarbonyl, $C_1$–$C_6$ alkylsulfonyl, arylsulfonyl and heteroarylsulfonyl;

B is a monocyclic or bicyclic ring system optionally containing up to 4 heteroatoms selected from N, O, and S, and wherein a $CH_2$ adjacent to any of the said N, O or S heteroatoms is optionally substituted with oxo (=O), and wherein B is optionally substituted by one to four $R^{11}$ groups;

D is a monocyclic or bicyclic ring system optionally containing up to 4 heteroatoms selected from N, O, and S, and wherein a $CH_2$ adjacent to any of the said N, O or S heteroatoms is optionally substituted with oxo (=O), and wherein D is optionally substituted by one to four $(CR^9R^{10})_n$E groups;

n is an integer having a value from 0–4;
m is an integer having a value from 2–6;
p is an integer having a value from 1–3;
q is an integer having a value from 0–3;
r is an integer having a value from 0–6;
$R^9$ is H or $C_1$–$C_4$alkyl;
$R^{10}$ is selected from H or $C_1$–$C_4$ alkyl, $C_1$–$C_4$ alkylhydroxy, $C_1$–$C_4$alkylaryl or $C_1$–$C_4$alkylheteroaryl, wherein said aryl or heteroaryl group may be substituted with 0–3 groups independently selected from H, halogen, $NO_2$, $C_1$–$C_4$alkyl, $C_3$–$C_{10}$ cycloalkyl, $C_2$–$C_6$alkenyl, $C_2$–$C_6$alkynyl, haloalkyl, haloalkoxy, OH, $C_1$–$C_4$alkoxy, $C_1$–$C_4$alkylcarbonyl, CN, $NH_2$, $NR^6R^7$, $SR^6$, $S(O)R^6$, $SO_2R^6$, $SO_3R^6$, $SO_2NR^6$, $CO_2H$, $CO_2R^6$, and $CONR^6R^7$;

$R^{11}$ at each occurence are independently selected from H, halogen, $NO_2$, $C_1$–$C_4$alkyl, $C_3$–$C_{10}$ cycloalkyl, $C_2$–$C_6$alkenyl, $C_2$–$C_6$alkynyl, haloalkyl, haloalkoxy, OH, $C_1$–$C_4$alkoxy-, $OR^6$, $O(CR^9R^{10})_rCO_2R^6$, $O(CR^9R^{10})_mNR^6R^7$, $O(CR^9R^{10})_pCN$, $O(CR^9R^{10})_rC$(=O)$NR^6R^7$, $C_1$–$C_4$alkylcarbonyl-, CN, $NH_2$, $NHR^6$, $NR^6R^7$, $NR^7(CR^9R^{10})_rCO_2R^6$, $NR^7OR^6$, $NR^7(CR^9R^{10})_mOR^6$, $NR^7CH[(CR^9R^{10})_pOR^6]_2$, $NR^7C[(CR^9R^{10})_pOR^6]_3$, $NR^7C(=O)R^6$, $NR^7(CR^9R^{10})_m OR^6$, $NR^7(CR^9R^{10})_mNR^6R^7$, $NR^7(CR^9R^{10})_mSO_2(CR^9R^{10})_qR^6$, $SR^7$, $S(O)R^7$, $SO_2R^7$, $SO_2NR^6$, $SO_3R^7$, $CO_2H$, $CO_2R^6$, and $CONR^6R^7$;

E is selected from H, halogen, $NO_2$, $C_1$–$C_4$alkyl, $C_3$–$C_{10}$ cycloalkyl, $C_2$–$C_6$ alkenyl, $C_2$–$C_6$ alkynyl, haloalkyl, haloalkoxy, OH, $OR^6$, CN, CHO, $CO_2R^6$, $CONR^6R^7$, $OCOR^6$, $OC(=O)OR^6$, $OC(=O)NR^6R^7$, $OCH_2CO_2R^6$, $C(=O)R^6$, $NH_2$, $NHR^6$, $NR^6R^7$, $NR^7C(=O)R^6$, $NR^7C(=O)OR^6$, $NR^7C(=O)C(=O)OR^6$, $NR^7C(=O)C(=O)NR^6R^7$, $NR^7C(=O)C(=O)(C_1$–$C_6$alkyl), $NR^7C(=NCN)OR^6$, $NR^7C(=O)NR^6R^7$, $NR^7C(=NCN)NR^6R^7$, $NR^7C('NR^6)NR^7R^8$, $NR^6SO_2NR^6R^7$, $NR^7SO_2R^6$, $SR^6$, $S(=O)R^6$, $SO_2R^6$, $SO_3R^7$, $SO_2NR^6R^7$, NHOH, $NHOR^6$, $NR^6NR^7NR^8$, $N(COR^6)OH$, $N(CO_2R^6)OH$, $CO_2R^6$, $CONR^6R^7$, $CONR^7(CR^9R^{10})_rr^6$, $CO(CR^9R^{10})_p$, $O(CHR^9)_qCO_2R^6$, $CO(CR^9CR^{10})_rOR^6$, $CO(CR^9R^{10})_pO(CR^9R^{10})_qR^6$, $CO(CR^9CR^{10})_rNR^6R^7$, $OC(O)O(CR^9R^{10})_mNR^6R^7$, $O(CO)N(CR^9R^{10})_pR^6$, $O(CR^9R^{10})_mNR^6R^7$, $NR^7C(O)(CR^9R^{10})_rR^6$, $NR^7C(O)(CR^9R^{10})_rOR^6$, $NR^7C(=NC)(CR^9R^{10})_rR^6$, $NR^7CO(CR^9R^{10})_r$ $NR^6R^7$, $NR^7(CR^9R^{10})_mOR^6$, $NR^7(CR^9R^{10})_rCO_2R^6$, $NR^7(CR^9R^{10})_mNR^6R^7$, $NR^7(CR^9R^{10})_nSO_2(CR^9R^{10})_qR^6$, $CONR^7(CR^9R^{10})_nSO_2(CR^9R^{10})_qR^6$, $SO_2NR^7(CR^9R^{10})_nCO(CR^9R^{10})_qR^6$, $SO_2NR^6(CR^9R^{10})_mOR^6$, $C_2$–$C_6$ alkenyl, $C_3$–$C_{10}$ cycloalkyl, $C_3$–$C_{10}$ cycloalkylmethyl, aryl, heterocyclic and alkylaryl, wherein said aryl groups may be substituted with 0–2 substituents independently selected $R^{12}$.

$R^{12}$ at each occurence are independently selected from H, halogen, $NO_2$, $C_1$–$C_4$alkyl, $C_3$–$C_{10}$ cycloalkyl, $C_2$–$C_6$alkenyl, $C_2$–$C_6$alkynyl, haloalkyl, haloalkoxy, OH, oxo, $C_1$–$C_4$alkoxy-, $OR^6$, $O(CR^9R^{10})_rCO_2R^6$, $O(CR^9R^{10})_m NR^6R^7$, $O(CR^9R^{10})_pCN$, $O(CR^9R^{10})_rC$(=O)$NR^6R^7$, $C_1$–$C_4$alkylcarbonyl-, CN, $NH_2$, $NHR^6$, $NR^6R^7$, $NR^7(CR^9R^{10})_rCO_2R^6$, $NR^7OR^6$, $NR^7(CR^9R^{10})_mOR^6$, $NR^7CH[(CR^9R^{10})_pOR^6]_2$, $NR^7C[(CR^9R^{10})_pOR^6]_3$, $NR^7C(=O)R^6$, $NR^7(CR^9R^{10})_mNR^7$ $(CR^9R^{10})_mNR^6R^7$, $NR^7(CR^9R^{10})_mSO_2(CR_9R^{10})_qR^6$, $SR^7$, $S(O)R^7$, $SO_2R^7$, $SO_2NR^6$, $SO_3R^7$, $CO_2H$, $CO_2R^6$, and $CONR^6R^7$;

Preferred compounds of the present invention are compounds of the formula I, and salts thereof, wherein:

X is a monocyclic or bicyclic ring system optionally containing up to 4 heteroatoms selected from N, O, and S, and wherein a $CH_2$ adjacent to any of the said N, O or S heteroatoms is optionally substituted with oxo (=O), and wherein X is optionally substituted by 0–3 substituents chosen from A, $R^1$, or $R^2$;

R is H;

$R^3$ is a 5- or 6-membered heterocyclic ring system containing up to 4 heteroatoms selected from N, O, and S, said heterocyclic ring system being optionally substituted with $R^5$, wherein when $R^5$ is hydroxy, the heterocycle may undergo tautomerization to an oxo species, or exist as an equilibrium mixture of both tautomers;

B is a monocyclic or bicyclic ring system optionally containing up to 4 heteroatoms selected from N, O, and S, and wherein a $CH_2$ adjacent to any of the said N, O or S heteroatoms is optionally substituted with oxo (=O), and wherein B is optionally substituted by one to two $R^{11}$ groups;

and all other constituents are as previously described.

Particularly preferred compounds of the invention are compounds of the formula I, or salts thereof, represented by one of the following formulas II through X:

(II)

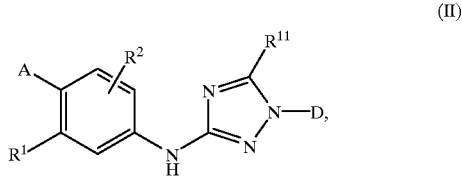

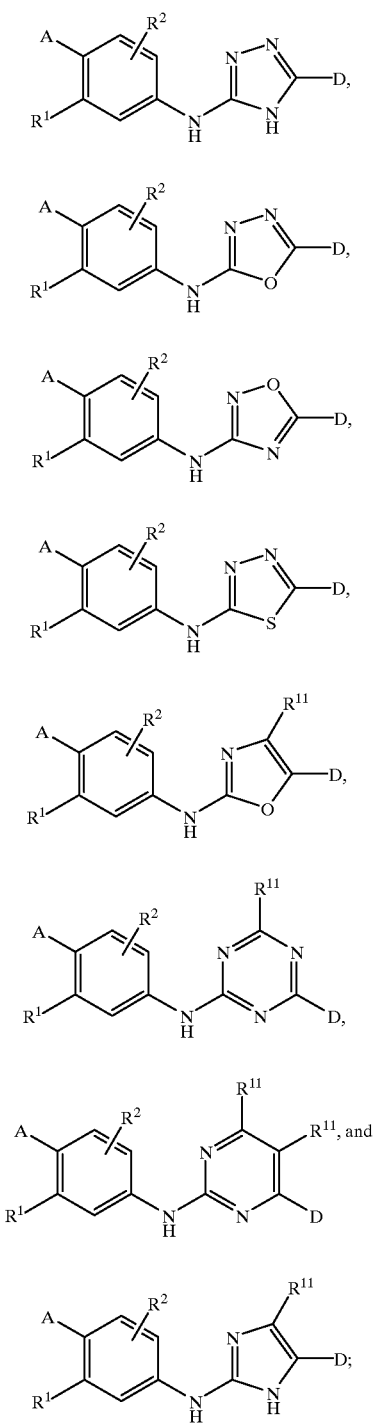

wherein:

R³ is a 5- or 6-membered heterocyclic ring system containing up to 4 heteroatoms selected from N, O, and S, said heterocyclic ring system being optionally substituted with R⁵, wherein when R⁵ is hydroxy, the heterocycle may undergo tautomerization to an oxo species, or exist as an equilibrium mixture of both tautomers;

and all other constituents are as previously described.

In the description above and elsewhere in the specification, including the claims, each occurrence of a particular constituent is independent of each other occurrence of that same constituent.

All documents cited herein are incorporated herein by reference in their entirety.

Listed below are definitions of various terms used in the specification and claims to describe the present invention.

The term "alkyl" refers to straight or branched chain alkyl.

The term "$C_{integer}$–$C_{integer}$" refers to a variable number of carbon atoms in a group depending on the integer values, as in $C_0$–$C_4$alkyl, which is meant to indicate a straight or branched alkyl group containing 0–4 carbon atoms. A group with 0 (zero) carbon atoms indicates that the carbon atom is absent i.e. there is a direct bond connecting adjacent terms. For example the term "$C_0$–$C_4$ alkylhydroxy" in the case "$C_0$" is meant to indicate the group hydroxy.

In the case where a subscript is the integer 0 the group to which the subscript refers to indicates that the group may be absent, i.e. there is a direct bond between the groups. For example in the definition of D which may be substituted with the group "$(CR^9R^{10})_n$E "the subscript may be 0 (zero). This is meant to indicate that D is directly connected to E by a bond i.e. D—E.

The term "halogen" or "halo" refers to fluorine, chlorine, bromine or iodine.

The term "aryl" refers to monocyclic or bicyclic aromatic hydrocarbons having 6 to 12 carbon atoms in the ring portion, such as phenyl, naphthyl, biphenyl and diphenyl groups which may be optionally substituted.

The term "alkenyl" refers to straight or branched chain alkenyl groups.

The term "alkynyl" refers to straight or branched chain alkynyl.

The term "cycloalkyl" refers to an optionally substituted, saturated cyclic hydrocarbon ring system.

The term "monocyclic" or bicyclic" refers to either a "carbocyclic" or a "heterocyclic" ring system.

The term "carbocyclic" refer to an optionally substituted, fully saturated or unsaturated, aromatic or nonaromatic cyclic group, which is a 3 to 7 membered monocyclic, or a 7 to 11 membered bicyclic, and all the atoms in the ring are carbon atoms. Exemplary groups include phenyl, naphthyl, anthracenyl, cyclohexyl, cyclohexenyl and the like.

The terms "heterocycle" and "heterocyclic" refer to an optionally substituted, fully saturated or unsaturated, aromatic or nonaromatic cyclic group, which is a 3 to 7 membered monocyclic, or a 7 to 11 membered bicyclic, which have at least one heteroatom and at least one carbon atom in the ring. Each heterocyclic ring may contain 1, 2, 3, or 4 heteroatoms selected from nitrogen, oxygen and sulfur, where the nitrogen and sulfur heteroatoms may also optionally be oxidized and the nitrogen heteroatoms may also optionally be quaternized. The heterocyclic group may be attached via a nitrogen or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydrothiopyranyl, tetrahydropyranyl, morpholinyl, thiamorpholinyl, thiamorpholinyl sulfoxide, tetrahydrothiopyranylsulfone, thiamorpholinyl sulfone, 1,3-dioxolane and tetrahydro-1,1-dioxothienyl, dioxanyl, isothiazolidinyl, thietanyl, thiiranyl, triazinyl, and triazolyl, and the like.

Exemplary bicyclic heterocyclic groups include benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

"IMPDH-associated disorders" refers to any disorder or disease state in which inhibition of the enzyme IMPDH (inosine monophosphate dehydrogenase, EC1.1.1.205, of which there are presently two known isozymes referred to as IMPDH type 1 and IMPDH type 2) would modulate the activity of cells (such as lymphocytes or other cells) and thereby ameliorate or reduce the symptoms or modify the underlying cause(s) of that disorder or disease. There may or may not be present in the disorder or disease an abnormality associated directly with the IMPDH enzyme. Examples of IMPDH-associated disorders include transplant rejection and autoimmune disorders, such as rheumatoid arthritis, multiple sclerosis, juvenile diabetes, asthma, and inflammatory bowel disease, as well as inflammatory disorders, cancer and tumor disorders, T-cell mediated hypersensitivity diseases, ischemic or reperfusion injury, viral replication diseases, proliferative disorders and vascular diseases.

As used herein the term "treating" includes prophylactic and therapeutic uses, and refers to the alleviation of symptoms of a particular disorder in a patient, the improvement of an ascertainable measurement associated with a particular disorder, or the prevention of a particular immune response (such as transplant rejection). The term "patient" refers to a mammal, preferably a human.

The compounds of this invention may contain one or more asymmetric carbon atoms and thus may occur as racemates and racemic mixtures, single enantiomers, diastereomeric mixtures and individual diastereomers. All such isomers of the compounds disclosed herein are expressly included within the scope of the present invention. Each stereogenic carbon may be of the R or S configuration.

Combinations of substituents and variables thereof that result in stable compounds are also contemplated within the present invention. The term "stable" as used herein refers to compounds which possess stability sufficient to allow manufacture and which maintain their integrity for a sufficient period of time to be useful as a therapeutic or diagnostic agent.

As used herein, the compounds of this invention are defined to include pharmaceutically acceptable derivatives and prodrugs thereof. A "pharmaceutically acceptable derivative or prodrug" includes any pharmaceutically acceptable salt, ester, salt of an ester, or other derivative of a compound of the present invention which, upon administration to a subject, is capable of providing (directly or indirectly) a compound of the invention. Particularly favored derivatives and prodrugs are those that increase the bioavailability of the compounds of the present invention when such compound is administered to a subject (e.g., by allowing an orally administered compound to be more readily absorbed into the blood) or which enhance delivery of the parent compound to a biological compartment (e.g., the brain or lymphatic system) relative to the parent species. Preferred prodrugs include derivatives where a group that enhances aqueous solubility or active transport through the gut membrane is appended to a compound of the present invention.

Pharmaceutically acceptable salts of the compounds disclosed herein include those derived from pharmaceutically acceptable inorganic and organic acids and bases known to those skilled in the art. Examples of suitable acid salts include, but are not limited to, the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, trifluoroacetic, tosylate and undecanoate. Other acids, for example oxalic, while not in themselves pharmaceutically acceptable, may be employed in the preparation of salts useful as intermediates in obtaining the compounds of the present invention and their pharmaceutically acceptable acid additional salts.

Salts derived from appropriate bases include, but are not limited to, the following: alkali metal (e.g., sodium), alkaline earth metal (e.g., magnesium), ammonium and N—$(C_{1-4}$ alkyl$)_4^+$ salts. The present invention also envisions the quaternization of any basic nitrogen-containing groups of the compounds disclosed herein. Water- or oil-soluble or dispersible products may be obtained by such quaternization.

Methods of Preparation

The compounds of the present invention may be synthesized using conventional techniques known in the art. Advantageously, these compounds are conveniently synthesized from readily available starting materials. Following are general synthetic schemes for manufacturing compounds of the present invention. These schemes are illustrative and are not meant to limit the possible techniques one skilled in the art may use to manufacture compounds disclosed herein. Different methods will be evident to those skilled in the art. Additionally, the various steps in the synthesis may be performed in an alternate sequence or order to give the desired compound(s). All documents cited herein are incorporated herein by reference in their entirety.

The group "D" in the synthetic schemes below is intended to designate the group in the claims defined by the letter "D", and in these schemes is not intended to imply or designate the element deuterium which is often symbolized in the chemical literature by the lower case letter "d", or in some chemical literature as the upper case letter "D".

Compounds of the present invention can be made by many methods, which will be known to one skilled in the art of organic chemistry. In general, the time taken to complete a reaction procedure will be judged by the person performing the procedure, preferably with the aid of information obtained by monitoring the reaction by methods such as HPLC or TLC. A reaction does not have to go to completion to be useful to this invention. The preparation of heterocycles useful to this invention are described in the series of books: "Comprehensive Heterocyclic Chemistry. The Structure, Reactions, Synthesis and Uses, of Heterocyclic Compounds" Katritzky, A. R., Rees, C. W. Ed's Pergamon Press New York, First edition 1984, and "Comprehensive Heterocyclic Chemistry II. A Review of the Literature 1982–1995. The Structure, Reactions, Synthesis and Uses, of Heterocyclic Compounds" Katritzky, A. R., Rees, C. W. and Scriven, E., F. Ed's Pergamon Press New York, 1996. Examples of methods useful for the production of compounds of this invention are illustrated in schemes 1–24:

Appropriately substituted 1,2,4-aminotriazoles of type (II), which are useful to this invention, can be made by several means, for example as shown in scheme 1, reaction of an appropriately substituted amine with a reagent such as 1,1'-thiocarbonyldi-2(1H)-pyridone,1,1'-thiocarbonyldiimidazole or thiophosgene in a solvent such as methylene chloride or dioxane yields the isothiocyanate. Treatment of the isothiocyanate with sodium salt of cyanamide yields the sodium salt of N-cyanothiourea which is cyclized to the aminotriazole (II) using an appropriately substituted hydrazine and a dehydrating agent such as 1-ethyl-3-(3-dimethylaminopropyl)carbodiimide hydrochloride (EDC), or DCC.

Scheme 1

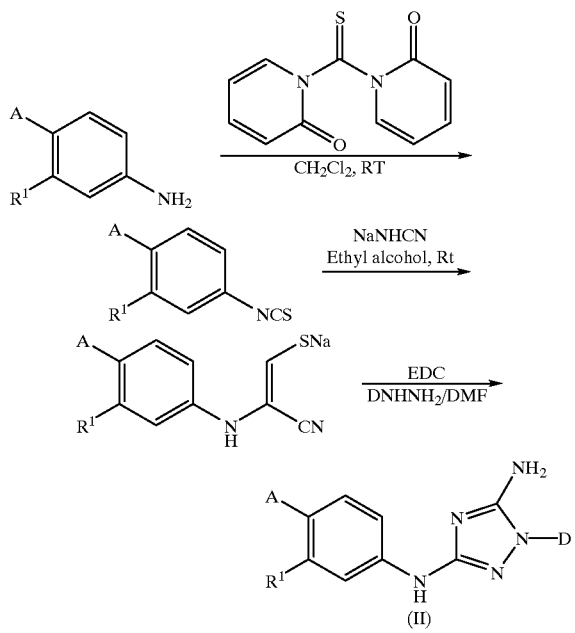

1,2,4-Aminotriazoles of type (II) which are useful to this invention, may also be prepared as outlined in Scheme 2. An appropriately substituted amine can react with diphenyl cyanocarbonimidate to yield the N-cyano-O-phenylisourea. Cyclization of N-cyano-O-phenylisourea to the appropriately substituted triazole (II) is achieved using a appropriately substituted hydrazine and a solvent such as acetonitrile.

Scheme 2

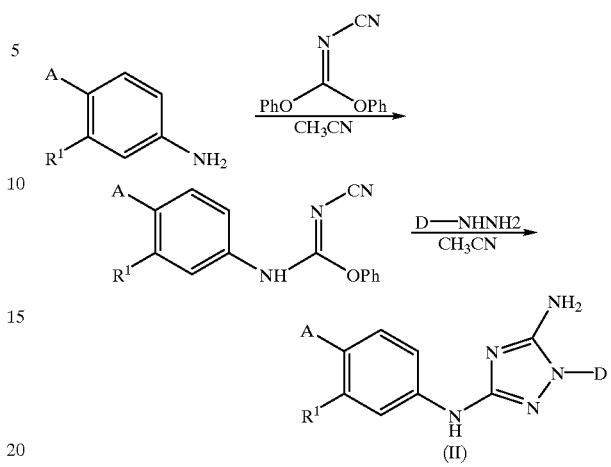

Appropriately substituted 1,2,4-triazoles of type (III), which are useful to this invention, can be prepared as by several methods for example as outlined in Scheme 3. Acylisothiocyanates are useful intermediates in the production of some compounds of this invention and are either commercially available or readily prepared by reaction of an acid chloride, with either sodium or potassium isothiocyanate in an inert solvent such as dioxane. Acid chlorides are either commercially available or readily prepared by reaction of a carboyxylic acid and a reagent such a as thionyl chloride, or oxalyl chloride in the presence of a catalytic amount of N,N-dimethylformamide, in an inert solvent such as chloroform or methylene chloride. Reaction of an appropriately substituted amine with an acylisothiocyanate yields the thiourea. The thiourea is cyclized to (III) using hydrazine in a solvent such as ethyl alcohol or a solvent mixture such as THF and ethyl alcohol, at a temperature preferably between 60° C. and the boiling point of the solvents utilized.

Scheme 3

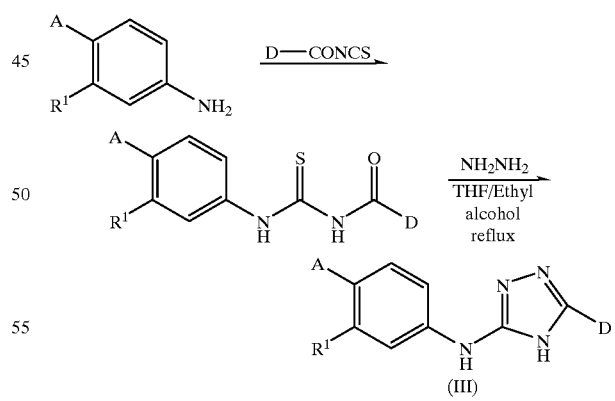

Appropriately substituted 2-amino-1,3,4-oxadiazoles of type (IV), which are useful to this invention, can be prepared by several methods one of which is outlined in Scheme 4. Reaction of an appropriately substituted amine with a activating agent such as 1,1'carbonyldiimidazole followed by treatment with a appropriately substituted hydrazine yields the carbonylhydrazide. The carbonylhydrazide on treatment with 1,2-dibromotetrachloroethane and triphenylphosphine in the presence of a suitable base such as triethylamine and an appropriate solvent such as acetonitrile yields compound (IV).

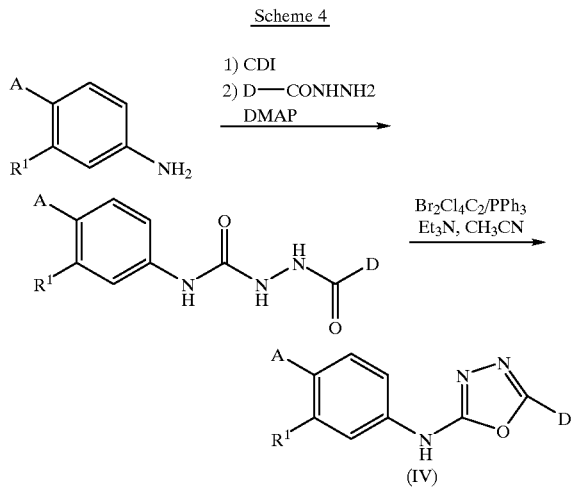

Appropriately substituted 3-amino-1,2,4 oxadiazoles of type (V), useful to this invention, can be prepared by several methods one of which is outlined in Scheme 5. Reaction of an appropriately substituted amine with a appropriately substituted acylisothiocyanate yields the thiourea. Reaction of the thiourea with a base such as sodium hydroxide or sodium hydride followed by a alkylating agent such as methyl iodide gives the S-methylisothiocarbamoyl intermediate which on treatment with hydroxylamine in the presence of a suitable solvent such as ethyl alcohol or butyl alcohol at a temperature preferably between 60 and 110° C. results in cyclization to the desired 3-amino-1,2, 4oxadiazole.

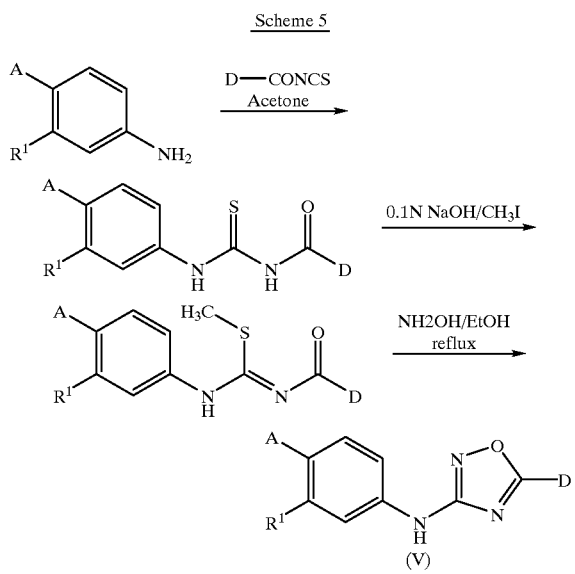

Appropriately substituted 2-amino-1,3,4-thiadiazoles of type (VI), which are useful to this invention, can be prepared by several methods one of which is illustrated in Scheme 6. Reaction of an appropriately substituted isothiocyanate with a appropriately substituted hydrazide yields the thiourea which is cyclized to the desired heterocycle using a dehydrating agent such as methansulphonic acid, in an inert solvent such as toluene or xylene, at a temperature preferably between 80° C. to 140° C.

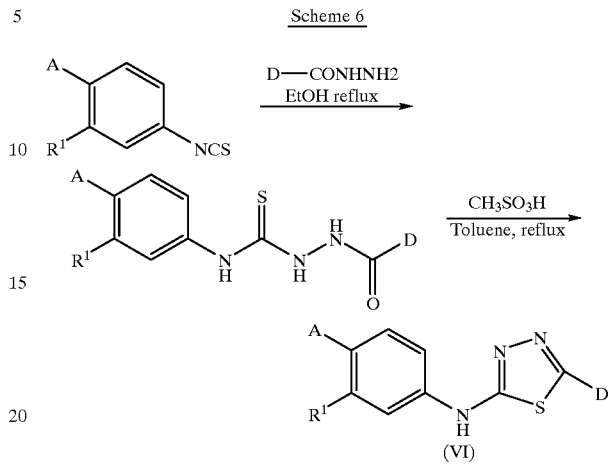

Appropriately substituted 3-amino-1,2,4-thiadiazoles, useful to this invention, can be made by several methods known to one skilled in the art of organic chemistry. One method is outlined in scheme 7. Reaction of an appropriately substituted isothiocyanate and amidoxime in a solvent such as chloroform, or toluene at a temperature preferably between 60° C. and 110° C. results in the production of the desired heterocycle. Amidoximes useful to this invention are either commercially available, or readily prepared by many methods known to one skilled in the art of organic chemistry such as reaction of a nitrile with anhydrous hydrochloric acid in anhydrous methanol followed by reaction of resulting imidate with hydroxylamine.

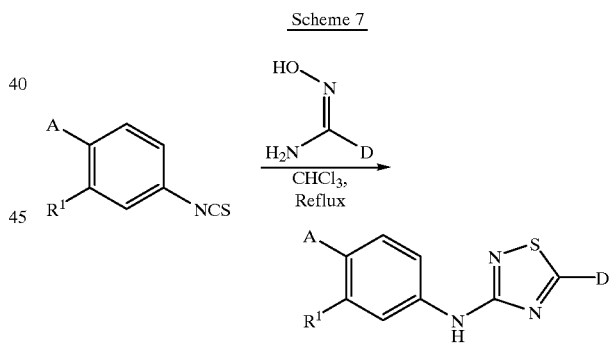

Appropriately substituted diarylamines, useful to this invention can be prepared by several methods include the one illustrated in Scheme 8. The coupling of amines with haloaryl compounds has been described in the chemical literature for example in "Rational Development of Practical Catalysts for Aromatic carbon-Nitrogen Bond Formation" in Accounts of Chemical Research (1998) 31, 805–818. Reaction of an appropriately substituted aniline with an appropriately substituted haloaryl compound in the presence of a catalyst such as tris(dibenzylideneacetone)dipalladium, a ligand such as BINAP, a base such as sodium tert-butoxide and a solvent such as toluene, or dioxane, preferably at a temperature between 80–110° C. results in production of the desired diarylamines.

Bromo or Iodo aryl intermediates such as 3-bromobiphenyl, are either commercially available or readily prepared by methods known to one skilled in the art of organic chemistry, by a variety of methods such as bromination of the aryl ring with Br$_2$, in the presence of iron, and other methods described in chapter 11 of "Advanced Organic Chemistry"3rd edition, Part B, Carey, F. A., and Sundberg, R. J., Plenum Press New York, 1990.

Scheme 8

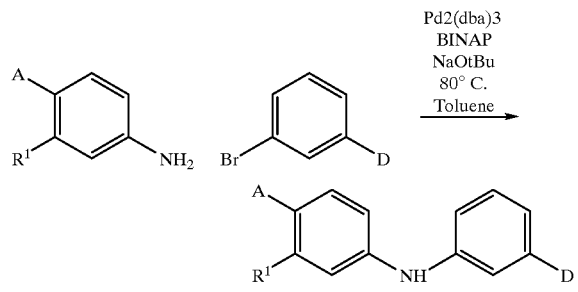

3-Aminoisoxazoles which are useful to this invention, can be prepared by several methods including the method outlined in scheme 9. Reaction of an appropriately substituted isocyanate with a ketone in the presence of a base such as sodium hydride and an alkylating agent such as methyl iodide gives a thiomethyl intermediate which on treatment with hydroxylamine in a solvent such as ethyl or butyl alcohol at a temperature preferably between 60–120° C. yields the appropriately substituted 3-aminoisoxazoles. Ketones useful to this invention are either commercially available or readily prepared by several methods such as Friedle-Crafts acylation as described in in chapter 11 of "Advanced Organic Chemistry "3rd edition, Part B, Carey, F. A., and Sundberg, R. J., Plenum Press New York, 1990, hydrolysis of an enol ether, or oxidation of an alcohol, as outlined in "Comprehensive Organic Transformations, A Guide to Functional Group Preparations" Larock, R. C., VCH Publishers, New York, 1989.

Scheme 9

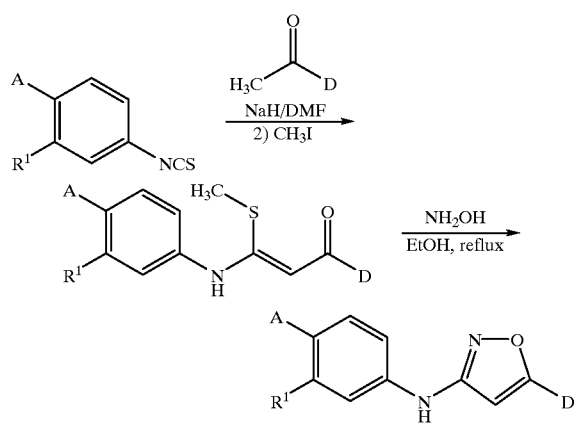

5-Aminothiazoles which are useful to this invention can be prepared by several methods including the method outlined in scheme 10. Reaction of an amine with a amino acid in the presence of an activating agent such as 1,1'-carbonyldiimidazole in a suitable solvent such as tetrahydrofuran yields an amide. Amides may be readily prepared by a number of methods including reaction of an amine with an acid chloride, or coupling of a carboxylic acid and the amine in the presence of a variety of coupling agents such as EDC, DCI, in the presence of an amine base. The coupling reaction may be enhanced by the addition of 1-hydroxybenzotriazole or similar additives. Reaction of the amide with Lawesson's reagent in the presence of a base such as pyridine at a temperature preferably between 80–120° C. yields the appropriately substituted 5-aminothiazoles.

Scheme 10

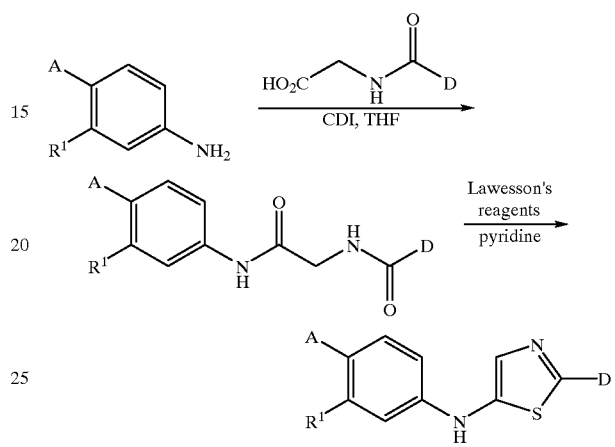

2-aminothiazoles useful to this invention can be prepared by several methods including the method outlined in scheme 11. Reaction of an isothiocyanate with ammonia in a solvent such as dioxane yields the thiourea. Aryl bromides useful to this invention, are either commercially available or readily prepared by reaction of a carboxylic acid with thionylbromide. Treatment of the thiourea with an acylbromide, in the presence of a solvent such as ethyl alcohol or dioxane, at a temperature preferably between 60° C. and 110° C., yields the appropriately substituted 2-amino-1,3-thiazoles.

Scheme 11

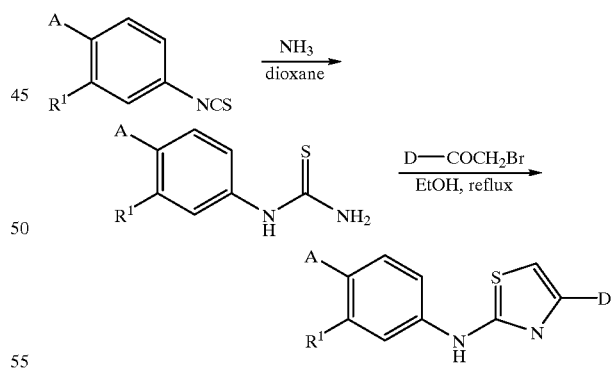

2-Amino 1,3-oxazolines useful to this invention may be prepared by several methods, an example of which is outlined in scheme 12. An appropriately substituted isothiocyanate is reacted with an aminoalcohol in a suitable solvent such as dioxane to yield the thiourea. Treatment of the thiourea with 2-chloro-3-ethylbenzoxazolium tetrafluoroborate in the presence of a base such as triethylamine in a solvent such as acetonitrile yields the appropriately substituted 2-amino-1,3-oxazolines.

Aminoalcohols useful to this invention are either commercially available or readily prepared by several methods.

One convenient method is reduction of azidoketones of the type described in schemes 15a–15d, either by catalytic hydrogenation in the presence of palladium on carbon in a solvent such as ethanol or ethyl acetate, or by a hydride reagent such as lithium aluminum hydride in a solvent such as dioxane or tetrahydrofuran.

Scheme 12

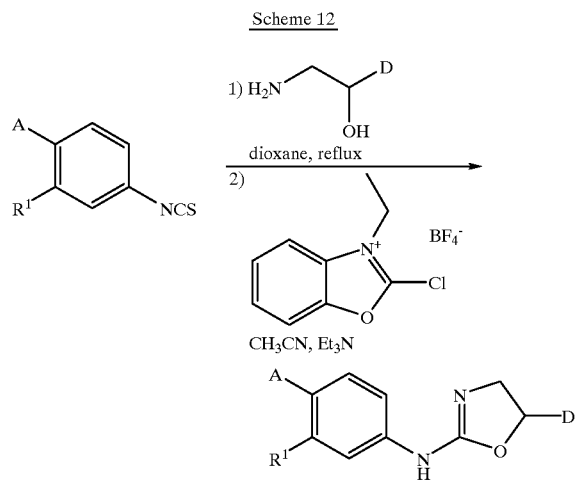

2-Aminooxazoles which are useful to this invention, can be prepared by several methods, including the method outlined in Scheme 13. Reaction of a isothiocyanate with a β-ketoamine in the presence of a base such as triethylamine and a solvent such as dioxane yields the thiourea. Reaction of the thiourea in the presence of a dehydrating agent such as dicyclohexylcarbodiimide or EDC, in a solvent such as dioxane or toluene, at a temperature preferably between 60° C. and 110° C., to yield the appropriately substituted 2-aminooxazoles. β-ketoamines useful to this invention are either commercially available or readily prepared by several methods. One method is reduction of azidoketones of the type described in schemes 15a–15d, by phosphine reagents such as triphenylphosphine in a solvent such as dioxane, followed by the addition of water or dilute ammonium hydroxide.

Scheme 13

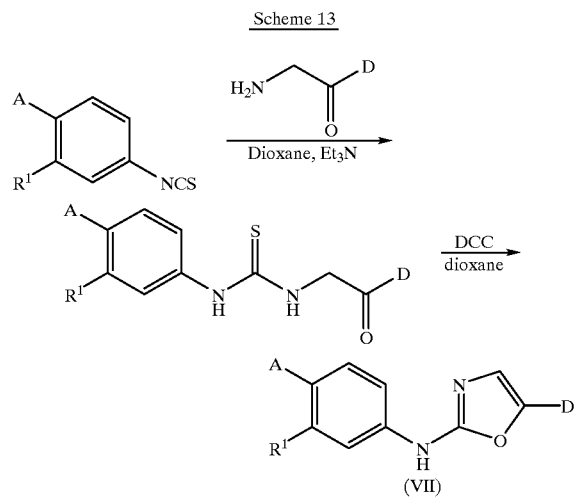

A second method of preparing 2-aminooxazoles is outlined in Scheme 14. Reaction of an appropriately substituted isothiocyanate with an acylazide of the type described in schemes 15a–15d in the presence of a phosphine such as triphenylphosphine in a solvent such as dichloromethane or dioxane at a temperature from room temperature to 100° C.

Caution: Appropriate safety methods, which are known to those experienced in conducting azide reactions, such as use of a blast shield, blast wall, or similar containment device, particularly when the reaction involves heating the organic azide, as well as the use of appropriate personal protection to avoid exposure to azides which may be toxic must be exercised during the preparation and use of organic azides.

Scheme 14

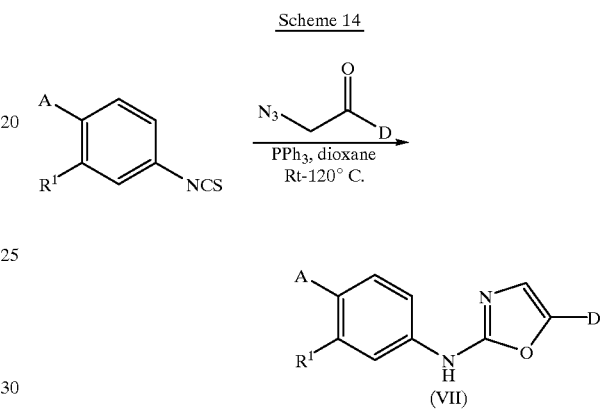

Azides useful to this invention may be prepared using one of the sequences outlined in scheme 15a–15d.

Scheme 15a outlines the treatment of the α-bromoketone with sodium azide in a solvent such as acetone, generally at room temperature, to yield the desired α-azidoketones useful as intermediates in this invention. α-Bromoketones are either commercially available or readily prepared by reaction of a ketone with a brominating agent such as bromine in acetic acid or pyridinium bromide perbromide and 30% hydrobromic acid.

Scheme 15a

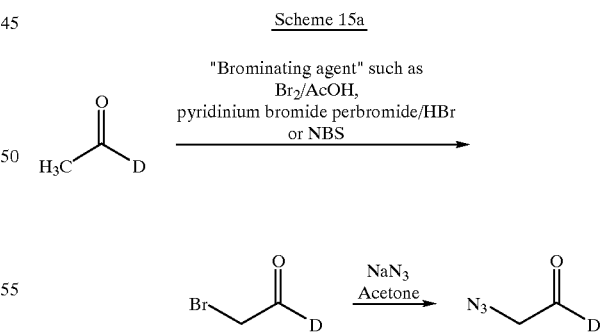

Scheme 15b outlines the treatment of the α-bromoketone with sodium azide in acetone gives the α-azidoketone. In this case, the α-bromoketone is prepared by reaction of a carboxylic acid with iso-butylchloroformate and N-methylmorpholine to provide the mixed anhydride, which on treatment with diazomethane gives the α-diazoketone. Reaction of the α-diazoketone with either HBr gas in a solvent such as ether or dioxane, or aqueous 48% HBr, provides the α-bromoketone.

Scheme 15b

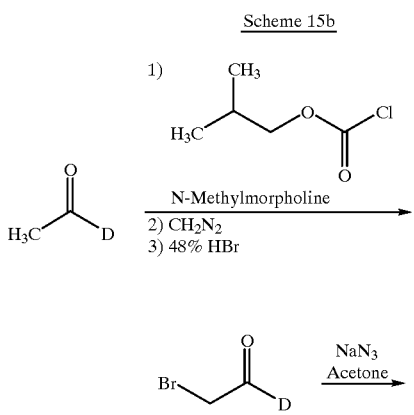

Scheme 15c illustrated preparation of α-bromoketone by reaction of a ketone with sulfuric acid and bromine to yield the α,α-dibromoketone, which on treatment with diethylphosphite and triethylamine yields the α-(mono) bromoketone. Treatment of the α-bromoketone with sodium azide in acetone gives the α-azidoketone.

Scheme 15c

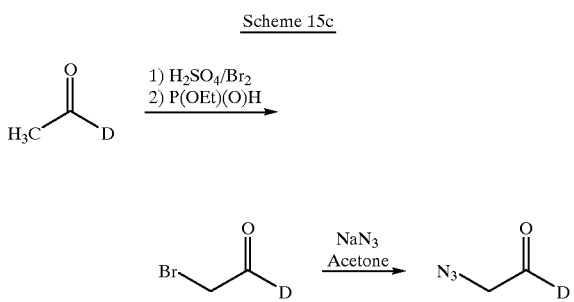

Scheme 15d illustrated preparation of a-bromoketone by reaction of an aryl bromide with tributyl(1-ethoxyvinyl)tin and bis-(triphenylphosphine)palladium dichloride to provide an intermediate enol ether. Treatment of the enol ether with N-bromosuccinamide at a temperature from 0° C. to room temperature yields the α-bromoketone. As previously described treatment of the α-bromoketone with sodium azide in acetone gives the α-azidoketone.

Scheme 15d

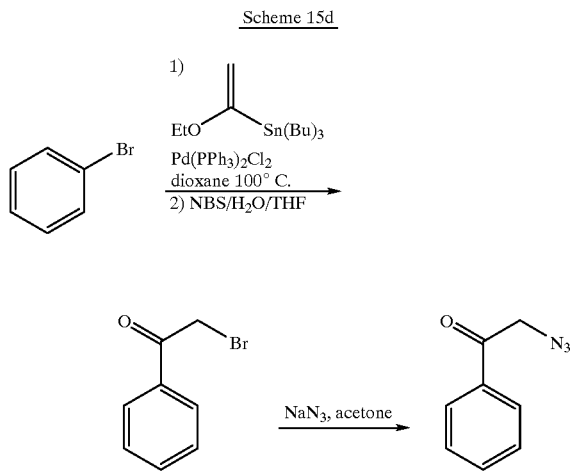

Triazines useful to this invention may be prepared by many methods including the methods outlined in schemes 16–18.

Reaction of a commercially available cyanuric halide such as cyanuric chloride with an aryl Grignard reagent yields the 2-aryl substituted-4,6-dichlorotriazine. Treatment of the dichlorotriazine with an aniline in a solvent such as acetone or dioxane with or without the addition of a base such as potassium carbonate, yields the intermediate 2-arylamino-6-aryl-4-chloro triazine. The remaining chloro group on the triazine may be replaced by a variety of nucleophiles such as amines in a solvent such as dioxane at a temperature preferably between 60–140° C., or a sodium salt of a thiol in a inert solvent or a sodium alkoxides in an appropriate alcoholic or inert solvent such as dioxane or toluene, to provide triazines of type (VIII).

Scheme 16

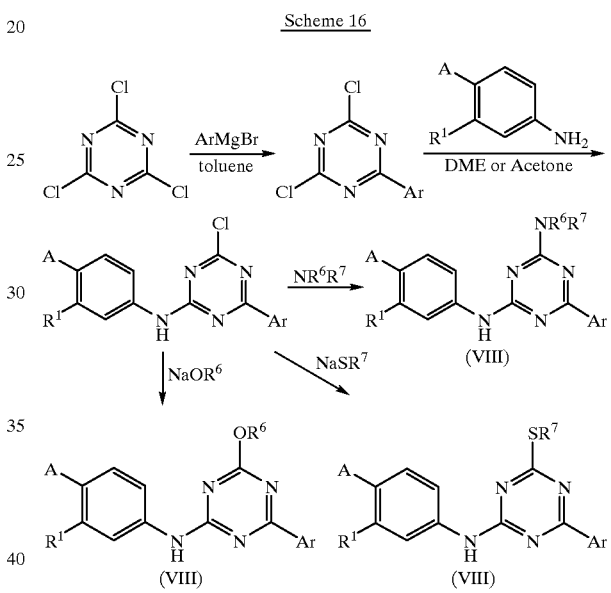

An alternative method of producing compounds useful to this invention is outlined in Scheme 17. Consecutive displacement of the chloro groups in cyanuric chloride by nucleophiles can be accomplished by careful choice of reaction conditions with particular attention to the reaction temperature and order of nucleophile addition. This has been documented in the chemical literature, for example, monosubstitution of cyanuric chloride is is depicted in Cambell, J. R., and Hatton, R. E., J. Org. Chem., 26, 2786, 1961, disubstitution of a triazine is illustrated in Thurston, J. T., Dudley, J. R, Kaiser, D. W., Schaefer, F. C, et. al. J. Amer. Chem. Soc. 73, 2981, 1954, and trisubstitution is shown in Controulis, J., Banks, C. K., J. Amer. Chem. Soc. 67, 1946, 1945. In the illustrated case, reaction of cyanuric chloride with an aniline yields the 2-arylamino-4,6-dichlorotriazine, preferably at a temperature between −45° C. and room temperature. Addition of a second amine to the 2-arylamino-4,6-dichlorotriazine at an extended period of time at room temperature or preferably less than 40° C., provides the monochlortriazine intermediate. Treatment of the monochlorotriazine intermediate with an amine at a temperature preferably between 60° C. and 140° C. provides the trisubstituted triazine.

Scheme 17

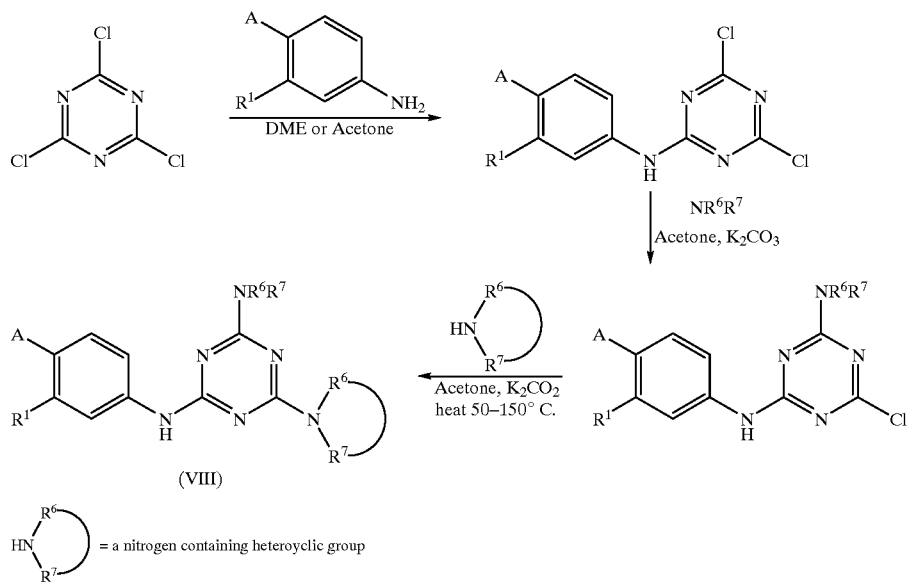

Scheme 18 illustrates another alternative preparation for triazines useful to this invention. A monochlortriazine intermediate produced in a manner similar to that described in scheme 17, is coupled with an aryl(trialkyl)tin or arylboronic acid or heteroaryl(trialkyl)tin or heteroarylboronic acid, in the presence of a palladium catalyst such as tetrakis triphenylphosphine palladium (0) to provide an aryl or heteroaryl substituted triazines of type (VIII).

Scheme 18

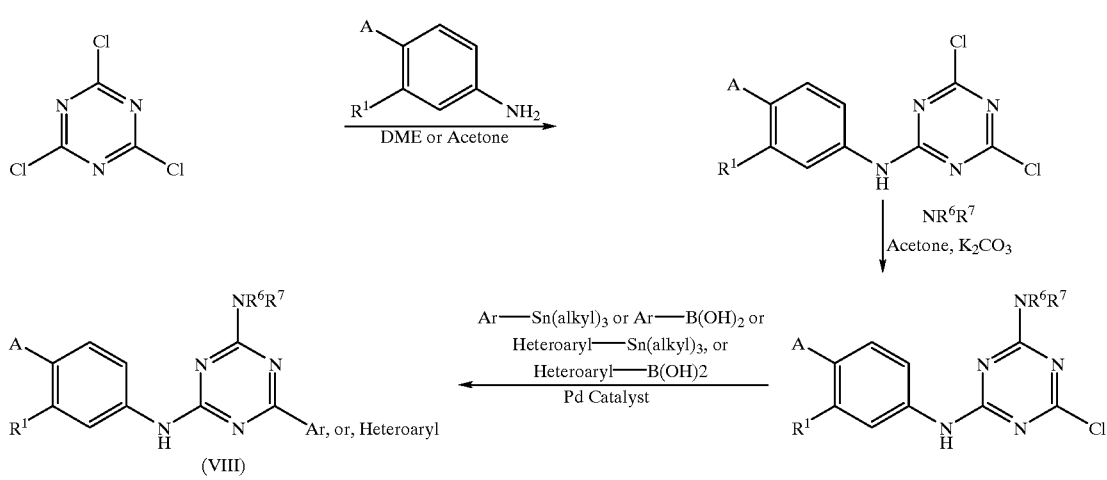

Pyrimidines useful for this invention may be prepared by several methods, one of which is illustrated in scheme 19. Reaction of an appropriately substituted aniline with 1,3 bis(tert-butoxycarbonyl)-2-methyl-2-thiopseudourea and triethylamine yields the bis-tert-butoxycarbonylguanidine. Cleavage of Boc groups using an acid such as TFA or 4N HCl in dioxane to yield the guanidine salt. There are many methods of liberating the free base of a guanidine including treatment with a base, such as sodium methoxide in anhydrous methanol, followed by filtration to remove the salt, or stirring with a commercially available strongly basic resin followed by filtration, and evaporation of the solvent. The guanidine was treated with a β-ketoester and heated in a suitable solvent such as ethanol or dioxane at a temperature preferably between 50° C.–150° C. to yield the pyrimidinone (XI). It is recognized that more than one isomeric pyrimidone may be produced during this reaction, and the desired product may require purification by chromatography or recrystalization. Pyrimidone are also useful intermediates which can be readily converted to the chloropyrimidine by treatment with phosphoryl chloride. Displacement of the chloro group of pyrimidines can be accomplished with a variety of nucleophiles in a manner similar to that described for the triazines above.

Scheme 19

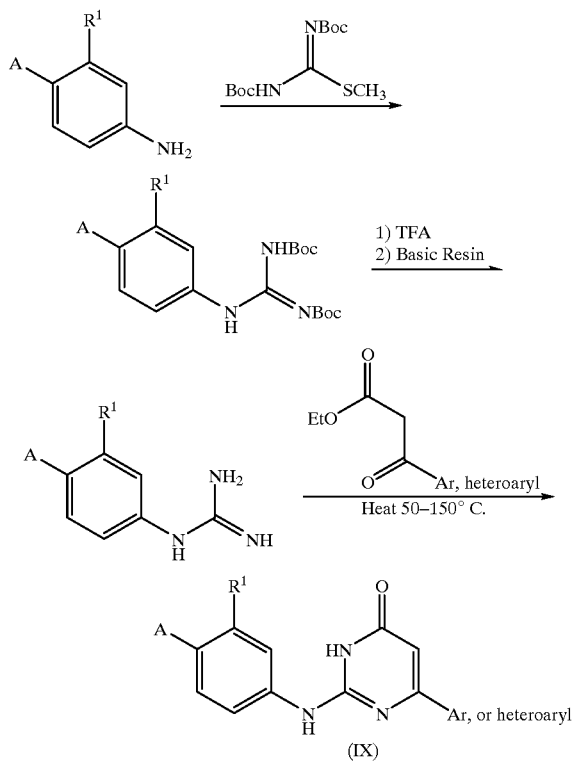

Imidazoles useful for this invention may be prepared according to the method outlined in scheme 20. Reaction of a guanidine (which can be obtained by the method outlined in scheme 19) with an α-bromoketone yields 2-aminoimidazoles of type (X) in the presence of a base such as potassium carbonate in a solvent such as N,N-dimethylformamide provides the desired aminoimidazoles. It is recognized that more than one isomeric imidazole can form during this reaction and the desired product can be obtained by a suitable chromatographic method or by recrystalization.

Scheme 20

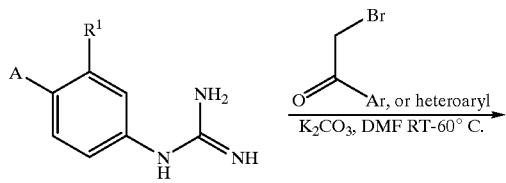

Amines attached to aryl or heteroaryl ring systems are useful as intermediates in this invention. There are many methods of preparing such intermediates known to one skilled in the art of organic chemisty. Several methods of preparing amines useful to this invention are illustrated in schemes 21–25.

A general method for the synthesis of an amine by metal catalyzed cross coupling methods is illustrated in Scheme 21, and similar examples have been reported in the chemical literature. The simplest case is a Suzuki type cross coupling (Miyaura, N., Yanagi, T. Suzuki, A., Synth. Comm. 11(7):513–519 (1981); A. Suzuki et. al., J. Am. Chem. Soc. 111:513 (1989); and V. N. Kalinin, Russ. Chem. Rev. 60:173 (1991)) of an aryl boronic acid or ester (21.1) with an appropriate bromoheterocycle in the presence of a suitable catalyst such as tetrakis(triphenylphosphine) palladium. After the cross coupling has been performed the product may be deprotected. The choice of protecting group and its method of removal will be readily apparent to one skilled in the art of organic chemistry. Such considerations and methods are, for example, described by Greene, Theodora W. and Wuts, Peter G. M. in "Protective Groups in Organic Synthesis." 2nd Ed. (1991) Publisher: (John Wiley and Sons, Inc., New York, N.Y. For example, if the protecting group is acetyl the product may be deprotected by treatment with aqueous potassium hydroxide at a concentration of 0.5N to 5 N at room temperature to 100° C. for a period between 0.5 h and 24 h, to provide amine (21.4).

For example aryl boronic acid (21.5) may react with the known 5-bromothiazole(21.6) in the presence of tetrakis (triphenylphosphine) palladium (0), to provide (21.7) which may be deprotected by an appropriate method.

Scheme 21

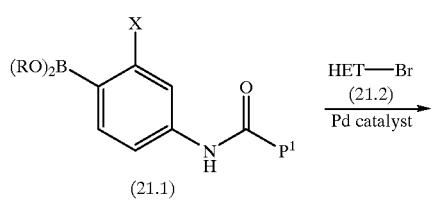

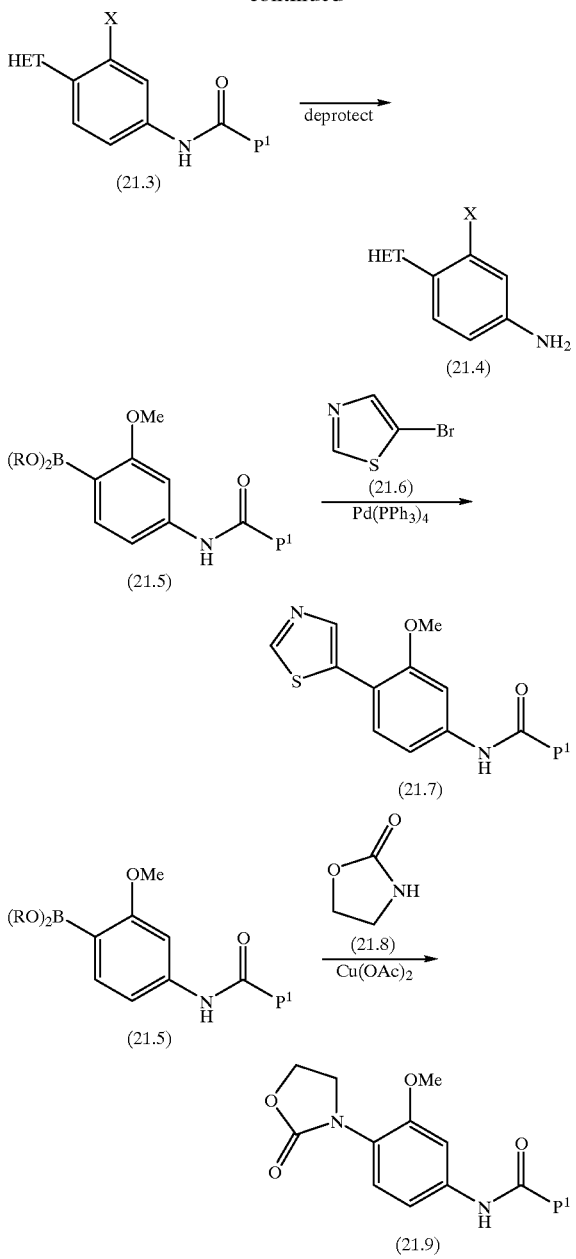

R = H, Alkyl
X = H, OMe, ect.
HET = a 5 or 6 membered ring containing at least one O, N, S atom with an unsaturated bond directly attached to the bromine
P¹ = alkyl, O-benzyl, O-tertbutyl, ect.

Copper has been recently been shown to be an effective catalyst for cross coupling of aryl boronic acids to N-unsubstituted heterocycles as described by Chan. et al., Tetrahed. Lett. 39:2933–2936 (1998); and Lam et al., Tetrahed. Lett. 39:2941–2944 (1998). This results in compounds in which the heterocycle is attached to the aryl ring through nitrogen rather than carbon. For example aryl boronic acid (21.5) may react with oxazolone (21.8) in the presence of copper (II) acetate in the presence of an amine base such as pyridine to provide intermediate (21.9) which may be deprotected by an appropriate method.

In general aryl boronic acids and ester, of type (21.1), where X is not Br or I, may be prepared as shown in Scheme 22, from the corresponding arylbromide 22.1 by treatment with a palladium catalyst such as [1,1'-Bis (diphenylphosphino)-ferrocene] dichloropalladium (II) and bis(pinacolato)diboron, (22.2), as reported by Ishayama et al., J. Org. Chem., (1995) 7508–7510. Aryl boronic esters may be converted to the corresponding boronic acid by several methods including treatment with aqueous HCl. In a variation of the synthesis, the nitrogen may be masked as a nitro group and later reduced by several means including metal reductions, such as by treatment with tin chloride in HCl or by refluxing the nitro compound with zinc in the presence of $CaCl_2$ in a solvent such as ethanol, or in certain cases the nitro group may be reduced by catalytic hydrogenation in the presence of catalysts such as palladium on carbon. The conditions for the reduction of nitro groups are detailed in several references including Hudlicky, M., "Reductions in Organic Chemistry", 2nd Ed., ACS Monograph 188, 1996, pp 91–101 American Chemical Society, Washington, D.C. A second variation of the synthesis allows the aryl bromide to remain through the entire synthesis and elaborated to the boronic acid at the end. This may eliminate the need for a protecting group.

Scheme 22

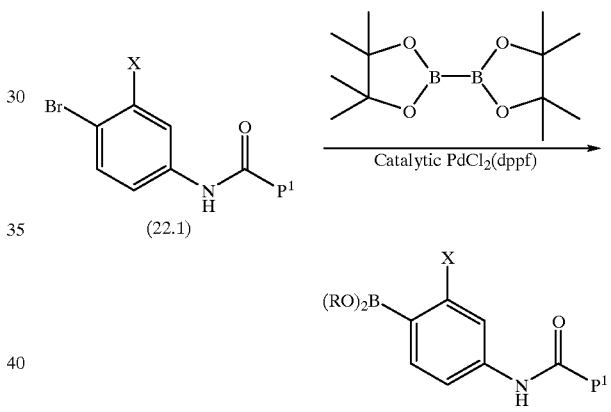

In certain cases it may be more expedient to construct the heterocyclic ring by other methods. A general method for the synthesis of 5-membered heterocycles includes the 1,3-dipolar cycloaddition reaction, which is well known to one skilled in the art of organic chemistry and is described by Padwa, Albert; Editor. in "1,3-Dipolar Cycloaddition Chemistry, Vol. 2" (1984) John Wiley and Sons, New York, N.Y.; and Padwa, Albert; Editor. in "1,3-Dipolar Cyцloaddition Chemistry, Vol. 1" (1984) John Wiley and Sons, New York, N.Y. For example oxazoles may be prepared as described in scheme 23, by 1,3 dipolar cycloaddition of the corresponding aldehyde (23.1) and (p-tolylsulfonyl)methyl isocyanate (TOSMIC) (23.2). The aldehyde may be commercially available or prepared from the corresponding methyl group by oxidation with reagents such as $CrO_3$, $MnO_2$, and ammonium cerium (IV) nitrate by methods well known to one skilled in the art of organic chemistry and is described in Hudlicky, M., "Oxidations in Organic Chemistry", ACS Monograph 186 (1990), American Chemical Society, Washington, D.C. The nitro group in intermediate (23.3) is reduced to an amine (23.4) as discussed above.

Scheme 23

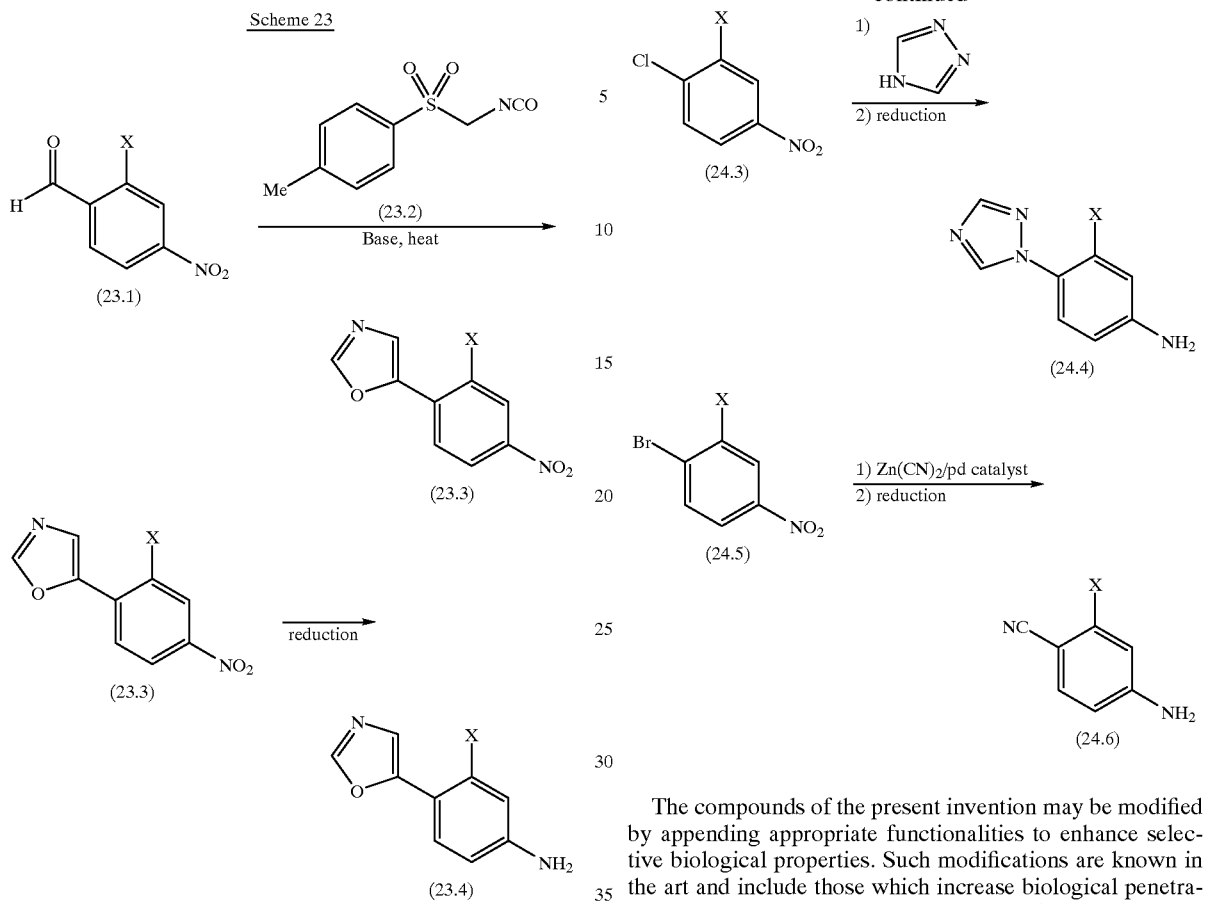

An alternative method of producing amines useful to this invention is by nucleophilic attack an electron deficient ring system as outlined in scheme 24. Halonitrobenzenes (24.1) are either commercially available or readily prepared by methods known to one skilled in the art of organic synthesis. Displacement with a variety of nucleophiles produces compounds of structure (24.2). In one example heating (24.3) with a nucleophilic heterocycle such as triazole with or without the addition of a base provides the intermediate nitro compound which may be reduced as previously described to provide amines (24.4). Alternatively simple organic nucleophiles such as cyanide can be reacted with halonitrobenzene (24.5) to provide an intermediate nitrocompound which can be reduced by many methods to amine (25.6).

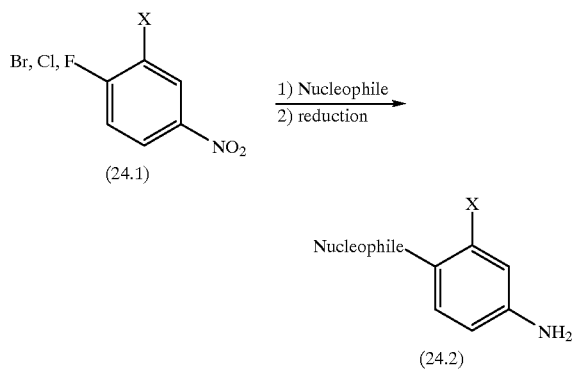

The compounds of the present invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

Utility

The compounds of the present invention inhibit IMPDH enzyme, and are thus useful in the treatment, including prevention and therapy of disorders which are mediated or effected by cells which are sensitive to IMPDH inhibition, as described previously. The present invention thus provides methods for the treatment of IMPDH-associated disorders, comprising the step of administering to a subject in need thereof at least one compound of the formula I, preferably at least one compound represented by formulas II through X, in an amount effective therefor. Other therapeutic agents, such as those described below, may be employed with the inventive compounds in the present methods. In the methods of the present invention, such other therapeutic agent(s) may be administered prior to, simultaneously with or following the administration of the compound(s) of the present invention.

Use of the compounds of the present invention is treating exemplified by, but is not limited to, treating a range of disorders such as: treatment of transplant rejection (e.g., kidney, liver, heart, lung, pancreas (e.g., islet cells), bone marrow, cornea, small bowel, skin allografts, skin homografts (such as employed in burn treatment), heart valve xenografts, serum sickness, and graft vs. host disease, in the treatment of autoimmune diseases, such as rheumatoid arthritis, psoriatic arthritis, multiple sclerosis, juvenile diabetes, asthma, inflammatory bowel disease (such as Crohn's disease and ulcerative colitis), pyoderma gangrenum, lupus (systemic lupus erythematosis), myasthenia gravis, psoriasis, dermatitis, dermatomyositis; eczema, seborrhoea, pulmonary inflammation, eye uveitis, hepatitis, Grave's disease, Hashimoto's thyroiditis, autoimmune thyroiditis, Behcet's or Sjorgen's syndrome (dry eyes/mouth), pernicious or immunohaemolytic anaemia, Addison's disease (autoimmune disease of the adrenal glands), idiopathic adrenal insufficiency, autoimmune polyglandular disease (also known as autoimmune polyglandular syndrome), glomerulonephritis, scleroderma, morphea, lichen planus, viteligo (depigmentation of the skin), alopecia areata, autoimmune alopecia, autoimmune hypopituatarism, Guillain-Barre syndrome, and alveolitis; in the treatment of T-cell mediated hypersensitivity diseases, including contact hypersensitivity, delayed-type hypersensitivity, contact dermatitis (including that due to poison ivy), uticaria, skin allergies, respiratory allergies (hayfever, allergic rhinitis) and gluten-sensitive enteropathy (Celiac disease); in the treatment of inflammatory diseases such as osteoarthritis, acute pancreatitis, chronic pancreatitis, asthma, acute respiratory distress syndrome, Sezary's syndrome and vascular diseases which have an inflammatory and or a proliferatory component such as restenosis, stenosis and artherosclerosis; in the treatment of cancer and tumor disorders, such as solid tumors, lymphomas and leukemia; in the treatment of fungal infections such as mycosis fungoides; in protection from ischemic or reperfusion injury such as ischemic or reperfusion injury that may have been incurred during organ transplantation, myocardial infarction, stroke or other causes; in the treatment of DNA or RNA viral replication diseases, such herpes simplex type 1 (HSV-1), herpes simplex type 2 (HSV-2), hepatitis (including hepatitis B and hepatitis C) cytomegalovirus, Epstein-Barr, and human immunodeficiency virus (HIV).

Additionally, IMPDH is also known to be present in bacteria and thus may regulate bacterial growth. As such, the IMPDH-inhibitor compounds of the present invention may be useful in treatment or prevention of bacterial infection, alone or in combination with other antibiotic agents.

In a particular embodiment, the compounds of the present invention are useful for the treatment of the aforementioned exemplary disorders irrespective of their etiology, for example, for the treatment of transplant rejection, rheumatoid arthritis, inflammatory bowel disease, and viral infections.

The present invention also provides pharmaceutical compositions comprising at least one of the compounds of formula I, preferably at least one of the compounds of formulas II through X, or a salt thereof, capable of treating an IMPDH-associated disorder in an amount effective therefor, alone or in combination with at least one additional therapeutic agent, and any pharmaceutically acceptable carrier, adjuvant or vehicle. "Additional therapeutic agents" encompasses, but is not limited to, an agent or agents selected from the group consisting of an immunosuppressant, an anti-cancer agent, an anti-viral agent, an anti-inflammatory agent, an anti-fungal agent, an antibiotic, or an anti-vascular hyperproliferation compound.

The term "pharmaceutically acceptable carrier, adjuvant or vehicle" refers to a carrier, adjuvant or vehicle that may be administered to a subject, together with a compound of the present invention, and which does not destroy the pharmacological activity thereof. Pharmaceutically acceptable carriers, adjuvants and vehicles that may be used in the pharmaceutical compositions of the present invention include, but are not limited to, the following: ion exchangers, alumina, aluminum stearate, lecithin, self-emulsifying drug delivery systems ("SEDDS") such as d(-tocopherol polyethyleneglycol 1000 succinate), surfactants used in pharmaceutical dosage forms such as Tweens or other similar polymeric delivery matrices, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β- and γ-cyclodextrin, or chemically modified derivatives such as hydroxyalkylcyclodextrins, including 2- and 3-hydroxypropyl-β-cyclodextrins, or other solubilized derivatives may also be used to enhance delivery of the compounds of the present invention.

The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the formula I may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compounds may also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel)

or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

Exemplary compositions for rectal administration include suppositories which may contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.1 to 500 mg/kg of body weight of active compound per day, which may be administered in a single dose or in the form of individual divided doses, such as from 1 to 5 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to IMPDH-associated disorders.

The compounds of the present invention may be employed alone or in combination with each other and/or other suitable therapeutic agents useful in the treatment of IMPDH-associated disorders, such as IMPDH inhibitors other than those of the present invention, immunosuppressants, anti-cancer agents, anti-viral agents, anti-inflammatory agents, anti-fungal agents, antibiotics, or anti-vascular hyperproliferation agents.

Exemplary such other therapeutic agents include the following: cyclosporins (e.g., cyclosporin A), CTLA4-Ig, antibodies such as anti-ICAM-3, anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and CD154 (a.k.a. "gp39"), such as antibodies specific for CD40 and/or CD154, fusion proteins constructed from CD40 and/or CD154/gp39 (e.g., CD40Ig and CD8gp39), inhibitors, such as nuclear translocation inhibitors, of NF-kappa B function, such as deoxyspergualin (DSG), non-steroidal antiinflammatory drugs (NSAIDs) such as ibuprofen, celecoxib and rofecoxib, steroids such as prednisone or dexamethasone, gold compounds, antiviral agents such as abacavir, antiproliferative agents such as methotrexate, leflunomide, FK506 (tacrolimus, Prograf), cytotoxic drugs such as azathiprine and cyclophosphamide, TNF-α inhibitors such as tenidap, anti-TNF antibodies or soluble TNF receptor, and rapamycin (sirolimus or Rapamune) or derivatives thereof.

The above other therapeutic agents, when employed in combination with the compounds of the present invention, may be used, for example, in those amounts indicated in the Physicians' Desk Reference (PDR) or as otherwise determined by one of ordinary skill in the art.

The compounds disclosed herein are capable of targeting and inhibiting IMPDH enzyme. Inhibition can be measured by various methods, including, for example, IMP dehydrogenase HPLC assays (measuring enzymatic production of XMP and NADH from IMP and NAD) and IMP dehydrogenase spectrophotometric assays (measuring enzymatic production of NADH from NAD). See, e.g., Montero et al., *Clinica Chimica Acta* 238:169–178 (1995). Additional assays known in the art can be used in ascertaining the degree of activity of a compound ("test compound") as an IMPDH inhibitor. The inventors used the following assay to determine the degree of activity of the compounds disclosed herein as IMPDH inhibitors:

Activity of IMPDH I and IMPDH II was measured following an adaptation of the method described in WO 97/40028. The reaction mixture was prepared containing 0.1M Tris pH 8.0, 0.1 M KCl, 3 mM EDTA, 2 mM DTT, 0.4 mM IMP and 40 nM enzyme (IMPDH I or IMPDH II). The reaction was started by the addition of NAD to a final concentration of 0.4 mM. The enzymatic reaction was followed by measuring the increase in absorbance at 340 nM that results from the formation of NADH. For the analysis of potential inhibitors of the enzyme, compounds were dissolved in DMSO to a final concentration of 10 mM and added to the assay mixture such that the final concentration of DMSO was 2.5%. The assay was carried out in a 96-well plate format, with a final reaction volume of 200 μl.

The compounds disclosed herein are capable of inhibiting the enzyme IMPDH at a measurable level, under the above-described assay or an assay which can determine an effect of inhibition of the enzyme IMPDH.

The following examples illustrate preferred embodiments of the present invention and do not limit the scope of the present invention which is defined in the claims. Abbreviations employed in the Examples are defined below. Compounds of the Examples are identified by the example and step in which they are prepared (e.g., "1A" denotes the title compound of step A of Example 1), or by the example only where the compound is the title compound of the example (for example, "2" denotes the title compound of Example 2).

| Abbreviations | |
|---|---|
| Ac | Acetyl |
| AcOH | Acetic acid |
| aq. | Aqueous |
| CDI | Carbonyldiimidazole |
| Bn | Benzyl |
| Boc | tert-butoxycarbonyl |
| DMAP | Dimethylaminopyridine |
| DMF | dimethylformamide |
| DMSO | Dimethylsulfoxide |
| EDC | 1-(3-Dimethylaminopropyl)-3-ethylcarbodiimide hydrochloride |
| EtOAc | Ethyl acetate |
| Et | Ethyl |
| EtOH | Ethanol |
| h | Hours |
| i | iso |
| HPLC | High pressure liquid chromatography |
| HOAc | Acetic acid |
| THF | Tetrahydrofuran |
| Lawesson's Reagent | [2,4-bis(4-methoxyphenyl)-1,3-dithia-2,4-diphosphetane-2-4-disufide |
| LC | liquid chromatography |
| Me | Methyl |
| MeOH | Methanol |
| min. | Minutes |
| $M^+$ | $(M + H)^+$ |
| $M^{+1}$ | $(M + H)^+$ |
| MS | Mass spectrometry |
| n | normal |
| Pd/C | Palladium on carbon |
| Ph | Phenyl |
| Pr | Propyl |
| Ret Time | Retention time |
| rt or RT | Room temperature |
| sat. | Saturated |
| TFA | Trifluoroacetic acid |
| THF | Tetrahydrofuran |
| TOSMIC | Tosylmethyl isocyanide |
| YMC | YMC Inc, Wilmington, NC 28403 |

EXAMPLE 1

Preparation of $N^3$-[3-Methoxy-4-(5-oxazolyl)phenyl]-1-phenyl-1H-1,2,4-triazole-3,5-diamine

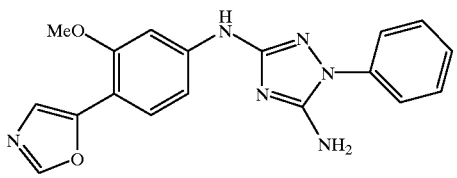

Example 1 Part A

4-Nitro-2-methoxy-(α,α bisacetoxy)toluene

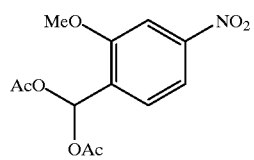

1A

To a 5 L three necked round bottom flask equipped with a mechanical stirrer was added 4-nitro-2-methoxytoluene (150.0 g, 0.8973 mol), HOAc (900 mL) and Ac$_2$O (900 mL). The mixture was stirred and cooled to 8° C. with an acetone/ice bath. Concentrated H$_2$SO$_4$ (136 mL) was carefully added while keeping the reaction temperature below 19° C. After cooling to 0° C., CrO$_3$ (252.6 g, 2.526 mol, 2.815 equiv.) was added portion-wise over 1 hour while maintaining the reaction temperature between 0–10° C. After the addition, the mixture was stirred at 0° C. for 30 minutes at which time the reaction was complete. The reaction mixture was then carefully poured into ice (1.5 kg) with stirring to give a slurry. The remaining black gummy residue was rinsed with HOAc (3×100 mL), and the washes were added to the slurry. After stirring for 10 minutes, the slurry was filtered. The cake was washed with water (3×400 mL) and suction dried for 17 hours to 1A (129.0 g, 51%). $^1$H NMR (CDCl$_3$) d 8.02 (s, 1H), 7.89 (d, J=8.4 Hz, 1H), 7.77 (s, 1H), (d, 8.4 Hz, 1H), 3.98 (s, 3H), 2.16 (s, 6H).

Example 1, Part B

4-Nitro-2-methoxybenzaldehyde

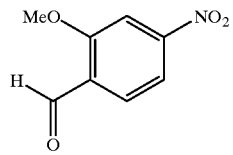

1B

To a 2 L round bottom flask equipped with a condenser and a mechanical stirrer was placed 1A (250.7 g, 0.8851 mol), dioxane (300 mL) and concentrated HCl (60 mL). The reaction mixture was heated to reflux and stirred under N$_2$ for 20 hours. Water (250 mL) was added dropwise while maintaining the reaction mixture at reflux. After cooling to 0° C. with an ice/water bath, the resulting slurry was stirred for 30 minutes and then filtered. The cake was washed with water (4×200 mL) and suction dried for 17 hours to give 1B (146.3 g, 91%) as a yellow solid. $^1$H NMR (CDCl$_3$) d 10.54 (s, 1H), 8.00 (d, J=8.3 Hz, 1H), 7.91 (s, 1H), 7.89 (d, J=8.3 Hz, 1H), 4.08 (s, 3H).

Example 1 Part C 5-(4-Nitro-2-methoxyphenyl)oxazole

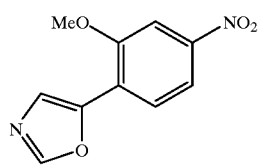

1C

To a 5 L three necked round bottom flask equipped with a condenser and a mechanical stirrer was placed 1B (146.3 g, 0.8076 mol), TOSMIC (157.7 g, 0.8077 mol), K$_2$CO$_3$ (116.6 g, 0.8075 mol) and MeOH (2.5 L). The mixture was heated to reflux under N$_2$ and stirred for 3 hours. Water (1.25 L) was added drop-wise while maintaining the pot temperature between 59–69° C. The resulting slurry was cooled to room temperature, and then to 5° C. with an ice-water bath. After stirring for 30 minutes at 5° C., the slurry was filtered. The resulting cake was washed with water (3×400 mL) and dried in a vacuum oven at 45° C. for 20 hours to 1C (148.5 g, 84%) as a yellow-reddish solid. $^1$H NMR (CDCl$_3$) d 8.02

(s, 1H), 7.97 (d, J=2 Hz, 1H), 7.95 (d, J=2 Hz, 1H), 7.86 (s, 1H), 7.78 (s, 1H), 4.11 (s, 3H).

Example 1, Part D 5-(4-Amino-2-methoxyphenyl)oxazole,

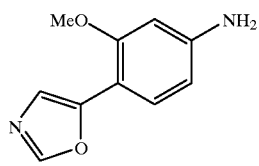

1D

In a 2 L hydrogenation flask was placed 1C (130.0 g, 0.6131 mol), Pd/C (10%, 26.2 g) and absolute EtOH (1280 mL). The mixture was hydrogenated at 35–45 psi $H_2$ until the reaction was complete. The mixture was filtered over a pad of celite (20 g) and the cake was washed with EtOH (3×100 mL). The filtrate was concentrated to a volume of 350 mL. Heptane (500 mL) was added to the resulting slurry. After stirring for 2 hours at room temperature, the slurry was filtered. The cake was washed with heptane (3×100 mL) and air-dried to give 1D (80.0 g). A second portion of product (30.2 g) was recovered from the mother liquor affording a total yield of 95%. $^1$H NMR (CDCl$_3$) d 7.88 (s, 1H), 7.60 (d, J=8.4 Hz, 1H), 7.41 (s, 1H), 6.41 (dd, J=8.4, 2.1 Hz, 1H), 3.34 (d, J=2.1 Hz, 1H), 3.98 (bs, 2H), 3.94 (s, 3H).

Example 1, Part E

3-Methoxy4-(5-oxazolyl)phenyl isothiocyanate

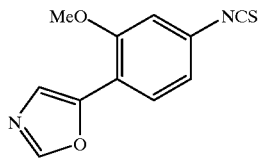

1E

A solution of 1D (3.50 g, 18.4 mmol) and 1,1'-thiocarbonyldi-2(2H)-pyridone (4.41 g, 18.4 mmol) in dichloromethane (100 mL) was stirred at RT for 3 h. The solvent was evaporated under vacuum, and the residue was subjected to column chromatography (30% AcOEt/hexane) to afford 1E (4.02 g, 94%) as white crystals.

Example 1

Part F. Sodium cyanamide

To a solution of cyanamide (3.00 g, 71.4 mmol) in methanol (30 mL) was added sodium methoxide (0.5 M methanol solution, 143 mL, 71.4 mmol) at RT over 25 min, and the resulting solution was stirred at RT for 2 h. Evaporation of the solvent gave 1F (4.57 g, 100% yield) as a white solid.

Example 1 Part G

Sodium Salt of N-cyano-N'-(3-Methoxy-4-(5-oxazolyl)phenyl)thiourea

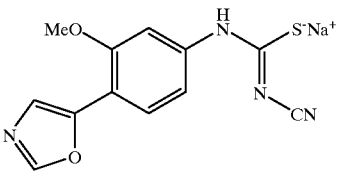

To a solution of 1E (2.50 g, 10.8 mmol) in absolute ethanol (150 mL) was added 1F (sodium cyanamide; 691 mg, 10.8 mmol) in absolute ethanol (100 mL) at rt over 30 min. The resulting solution was stirred at RT for 4 h. Most of the solvent was evaporated under vacuum, and to the residue was added dichloromethane (60 mL). The precipitate was collected by filtration, and was washed with dichloromethane to provide 1G (2.15 g, 67%) as a white solid.

Example 1, Part H $N^3$-[3-Methoxy-4-(5-oxazolyl)phenyl]-1-phenyl-1H-1,2,4-triazole-3,5-diamine To a mixture of 1G (30.0 mg, 0.101 mmol) and 1-ethyl-3-(3-dimethylaminopropyl)carbodiimide hydrochloride (37.2 mg, 0.202 mmol) in DMF (3.0 mL) was added phenylhydrazine (20.0 μL, 0.203 mmol). The resulting mixture was heated at 50° C. for 15 h, diluted with AcOEt, washed with water, brine, and dried over anhydrous MgSO$_4$. After the solvent was removed under vacuum, the residue was purified by preparative HPLC, to afford 1 in the form of trifluoroacetic acid salt (17.0 mg, 36% yield). The product was 99% pure by LC/MS (retention time=3.34 min.; $M^+$=349.18. Column: YMC S5 ODS 4.6×5.0 mm Ballistic. Solvent A=10% MeOH, 90% H$_2$O, 0.1% TFA; Solvent B=90% MeOH, 10% H$_2$O, 0.1% TFA).

EXAMPLE 2

Preparation of $N^3$-[3-Methoxy-4-(5-oxazolyl)phenyl]-1-(2-pyridinyl)-1H-1,2,4-triazole-3,5-diamine

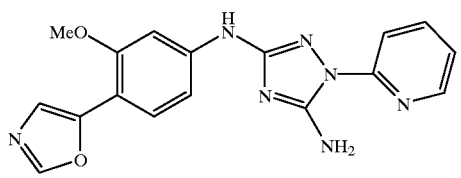

2

Example 2 Part A

N-Cyano-N'-(3-methoxy-4-(5-oxazolyl)phenyl)-O-phenylisourea

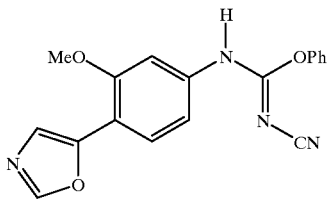

2A

A mixture of 5-(4-amino-2-methoxyphenyl)oxazole (0.200 g, 1.05 mmol) and diphenyl cyanocarbonimidate (0.258 g, 1.05 mmol) in 10 mL of acetonitrile was stirred at reflux for 40 h. As the reaction mixture cooled to room temperature, a yellow solid precipitated out of solution. The volume of solvent was reduced by half, and ether was added. Vacuum filtration afforded 2A (0.330 g, 94%) as a pale yellow solid which was 97% pure by LC/MS (retention time=3.48 min.; $M^+$=335.15. Column: YMC S5 ODS 4.6×5.0 mm Ballistic. Solvent A=10% MeOH, 90% $H_2O$, 0.1% TFA; Solvent B=90% MeOH, 10% $H_2O$, 0.1% TFA).

Example 2 Part B $N^3$-[3-Methoxy-4-(5-oxazolyl)phenyl]-1-(2-pyridinyl)-1H-1,2,4-triazole-3,5-diamine A solution of 2A (150.0 mg, 0.422 mmol) and 2-hydrazinopyridine (92.0 mg, 0.843 mmol) in acetonitrile (5.0 mL) was heated at reflux for 16 h. After cooling to RT, the solution was diluted with AcOEt, washed with water and brine, dried over anhydrous $MgSO_4$. The solvent was removed under vacuum, and the residue was washed first with diethyl ether and then with methanol to give 2 (15.0 mg, 10%) as a beige solid. The product was 99% pure by LC/MS (retention time=3.60 min.; $M^+$=350.10. Column: YMC S5 ODS 4.6×5.0 mm Ballistic. Solvent A=10% MeOH, 90% $H_2O$, 0.1% TFA; Solvent B=90% MeOH, 10% $H_2O$, 0.1% TFA).

EXAMPLE 3

Preparation of 1-Cyclohexyl-$N^5$-[3-methoxy-4-(5-oxazolyl)phenyl]-1H-1,2,4-triazole-3,5-diamine and 1-Cyclohexyl-$N^3$-[3-methoxy-4-(5-oxazolyl)phenyl]-1H-1,2,4-triazole-3,5-diamine

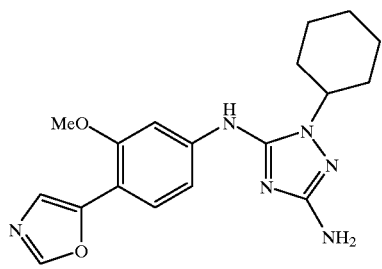

3'

-continued

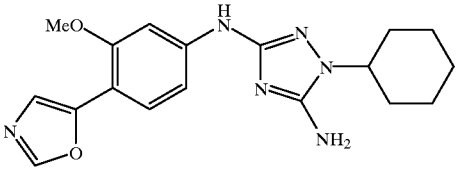

3"

To a solution of cyclohexylhydrazine hydrochloride (61.0 mg, 0.405 mmol) in DMF (5.0 mL) was added triethylamine (84.5 µL, 0.606 mmol), and the mixture was stirred at RT for 10 min. The precipitate produced was removed by suction filtration, and the filtrate was directly treated with 1 G (60.0 mg, 0.202 mmol) and 1-ethyl-3-(3-dimethylaminopropyl) carbodiimide hydrochloride (74.4 mg, 0.404 mmol). The resulting mixture was heated at 60° C. for 16 h before it was diluted with AcOEt, washed with water, brine and dried over anhydrous $MgSO_4$. After the solvent was removed under vacuum, the residue was purified by preparative HPLC, followed by neutralization with 10% $Na_2CO_3$, to afford 3' (1-Cyclohexyl-$N^5$-[3-methoxy-4-(5-oxazolyl)phenyl]-1H-1,2,4-triazole-3,5-diamine; 7.9 mg, 11%) and 3" (1-Cyclohexyl-$N^3$-[3-methoxy-4-(5-oxazolyl)phenyl]-1H-1,2,4-triazole-3,5-diamine; 25.8 mg, 36%). Both products are white solids and 100% pure by LC/MS (for 3', retention time=3.30 min.; $M^+$=355.24. For 3", retention time=3.74 min.; $M^+$=355.24. Column: YMC S5 ODS 4.6×5.0 mm Ballistic. Solvent A 10% MeOH; 90% $H_2O$, 0.1% TFA; Solvent B=90% MeOH, 10% $H_2O$, 0.1% TFA).

EXAMPLE 4

Preparation of $N^3$-[3-Methoxy-4-(5-oxazolyl) phenyl]-1-(2-methylphenyl)-1H-1,2,4-triazole-3,5-diamine

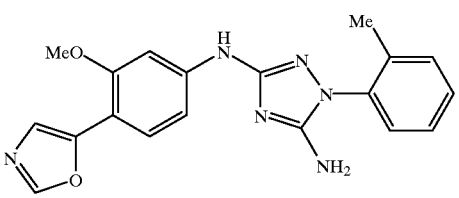

4 o-Tolylhydrazine hydrochloride (64.1 mg, 0.404 mmol), triethylamine (84.5 µL, 0.606 mmol), DMF (6.0 mL), 1G (60.0 mg, 0.202 mmol), and 1-ethyl-3-(3-dimethylaminopropyl)carbodiimide hydrochloride (74.4 mg, 0.404 mmol) was subjected to the same procedure used in Example 3 to afford the title compound 4 in the form of trifluoroacetic acid salt (42.0 mg, 44%) as a white powder. The product was 100% pure by LC/MS (retention time=3.49 min.; $M^+$=363.27. Column: YMC S5 ODS 4.6×5.0 mm Ballistic. Solvent A=10% MeOH, 90% $H_2O$, 0.1% TFA; Solvent B=90% MeOH, 10% $H_2O$, 0.1% TFA).

EXAMPLE 5

Preparation of N³-[3-Methoxy-4-(5-oxazolyl)phenyl]-1-(4-methylphenyl)-1H-1,2,4-triazole-3,5-diamine

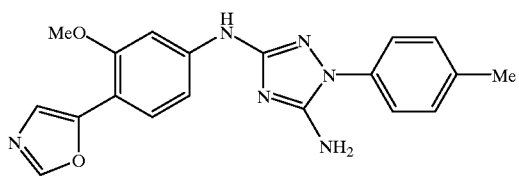

5 p-Tolylhydrazine hydrochloride (64.1 mg, 0.404 mmol), triethylamine (84.5 μL, 0.606 mmol), DMF (6.0 mL), 1G (60.0 mg, 0.202 mmol), and 1-ethyl-3-(3-dimethylaminopropyl)carbodiimide hydrochloride (74.4 mg, 0.404 mmol) was subjected to the same procedure used in Example 3 to afford the title compound 5 in the form of trifluoroacetic acid salt (48.1 mg, 50%) as a white powder. The product was 99% pure by LC/MS (retention time=3.76 min.; 363.27. Column: YMC S5 ODS 4.6×5.0 mm Ballistic. Solvent A=10% MeOH, 90% $H_2O$, 0.1% TFA; Solvent B=90% MeOH, 10% $H_2O$, 0.1% TFA).

EXAMPLE 6

Preparation of N³-[3-Methoxy-4-(5-oxazolyl)phenyl]-1-(3-methylphenyl)-1H-1,2,4-triazole-3,5-diamine

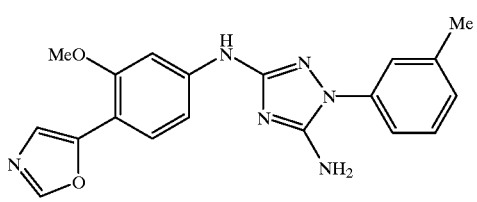

6

A mixture of 1G (60.0 mg, 0.202 mmol), 1-ethyl-3-(3-dimethylaminopropyl)carbodiimide hydrochloride (74.4 mg, 0.404 mmol), and m-tolylhydrazine (50.9 mg, 0.404 mmol) in DMF (6.0 mL) was subjected to the same procedure used in Example 3 to afford the title compound 6 in the form of trifluoroacetic acid salt (57.4 mg, 60%) as a white solid. The product was 99% pure by LC/MS (retention time=3.72 min.; M⁺=363.27. Column: YMC S5 ODS 4.6× 5.0 mm Ballistic. Solvent A=10% MeOH, 90% $H_2O$, 0.1% TFA; Solvent B=90% MeOH, 10% $H_2O$, 0.1% TFA).

EXAMPLE 7

Preparation of N³-[3-Methoxy-4-(5-oxazolyl)phenyl]-1-(3-nitrophenyl)-1H-1,2,4-triazole-3,5-diamine

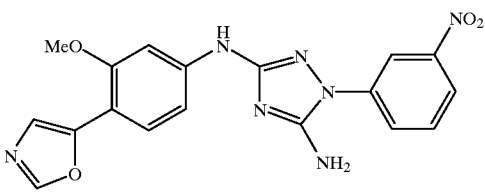

7

3-nitrophenylhydrazine hydrochloride (191.5 mg, 1.01 mmol), triethylamine (0.21 mL, 1.43 mmol), DMF (10 mL), 1G (150 mg, 0.506 mmol), and 1-ethyl-3-(3-dimethylaminopropyl)carbodiimide hydrochloride (194 mg, 1.01 mmol) was subjected to the same procedure used in Example 3 to give the title compound 7 (13.4 mg, 7%) as a yellow solid. The product was 96% pure by LC/MS (retention time=3.84 min.; M⁺=394.24. Column: YMC S5 ODS 4.6×5.0 mm Ballistic. Solvent A=10% MeOH, 90% $H_2O$, 0.1% TFA; Solvent B=90% MeOH, 10% $H_2O$, 0.1% TFA).

EXAMPLE 8

Preparation of N³-[3-Methoxy-4-(5-oxazolyl)phenyl]-1-(4-nitrophenyl)-1H-1,2,4-triazole-3,5-diamine

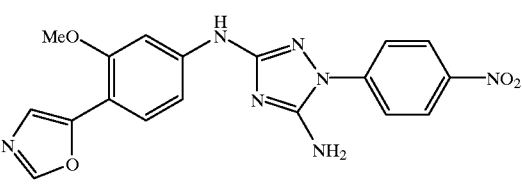

8

A mixture of 1G (150 mg, 0.506 mmol), 1-ethyl-3-(3-dimethylaminopropyl)carbodiimide hydrochloride (194 mg, 1.01 mmol), and 4-nitrophenylhydrazine (172 mg, 1.10 mmol) in DMF (10 mL) was subjected to the same procedure used in the preparation of 1. Purification was carried out by preparative HPLC, followed by neutralization, to give the title compound 8 (32.4 mg, 16%) as a red solid. The product was 100% pure by LC/MS (retention time=3.97 min.; M⁺=394.24. Column: YMC S5 ODS 4.6×5.0 mm Ballistic. Solvent A=10% MeOH, 90% $H_2O$, 0.1% TFA; Solvent B=90% MeOH, 10% $H_2O$, 0.1% TFA).

EXAMPLE 9

Preparation of 1-(4-Aminophenyl)-N³-[3-methoxy-4-(5-oxazolyl)phenyl]-1H-1,2,4-triazole-3,5-diamine

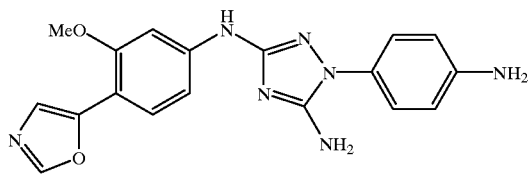

9

A suspension of 8 (27.8 mg, 0.0707 mmol) and 10% Pd/C (10.0 mg) in 1:3 mixture of trifluoroacetic acid and methanol (24 mL) was stirred under hydrogen atmosphere for 7 h. After the Pd/C was removed by filtration and the solvent was evaporated under vacuum, the crude product was purified by preparative HPLC, followed by lyophilization, to give the title compound 9 in the form of two equivalent of trifluoroacetic acid salt (16.3 mg, 39%). The product was 99% pure by LC/MS (retention time=2.77 min.; M⁺=364.28. Column: YMC S5 ODS 4.6×5.0 mm Ballistic. Solvent A=10% MeOH, 90% H₂O, 0.1% TFA; Solvent B=90% MeOH, 10% H₂O, 0.1% TFA).

EXAMPLE 10

Preparation of 1-(3-Aminophenyl)-N³-[3-methoxy-4-(5-oxazolyl)phenyl]-1H-1,2,4-triazole-3,5-diamine

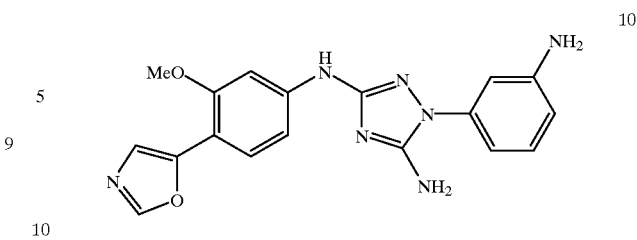

10

A suspension of 7 (11.3 mg, 0.0311 mmol) and 10% Pd/C (5.0 mg) in 1:3 mixture of trifluoroacetic acid and methanol (8 mL) was stirred under hydrogen atmosphere for 5 h. After the Pd/C was removed by filtration and the solvent was evaporated under vacuum, the crude product was purified by preparative HPLC, followed by lyophilization, to give the title compound 10 in the form of two equivalent of trifluoroacetic acid salt (7.4 mg, 40%). The product was 98% pure by LC/MS (retention time=2.89 min.; M⁺=364.28. Column: YMC S5 ODS 4.6×5.0 mm Ballistic. Solvent A=10% MeOH, 90% H₂O, 0.1% TFA; Solvent B=90% MeOH, 10% H₂O, 0.1% TFA).

EXAMPLES 11 TO 17

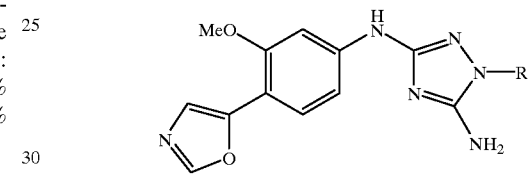

Compounds 11–17 were prepared from 1G by a route analogous to that used in Example 1, replacing hydrazine with the required HN₂NH—R. The compounds of these examples have structures outlined in Table 1 below.

TABLE 1

| Ex. No | R | Compound name | HPLC time (min) | M⁺ |
|---|---|---|---|---|
| 11 | 3-F-C₆H₄ | 1-(3-Fluorophenyl)-N³-[3-methoxy-4-(5-oxazolyl)phenyl]-1H-1,2,4-triazole-3,5-diamine | 3.715 | 367.27 |
| 12 | 4-Br-C₆H₄ | 1-(4-Bromophenyl)-N³-[3-methoxy-4-(5-oxazolyl)phenyl]-1H-1,2,4-triazole-3,5-diamine | 3.960 | 428.12 |
| 13 | 3-CN-C₆H₄ | N³-[5-Amino-3-[[3-methoxy-4-(5-oxazolyl)phenyl]amino]-1H-1,2,4-triazol-1-yl]benzonitrile | 3.563 | 374.20 |
| 14 | 3-OMe-C₆H₄ | N³-[3-Methoxy-4-(5oxazolyl)phenyl]-1-(3-methoxyphenyl)-1H-1,2,4-triazole-3,5-diamine | 3.813 | 379.28 |

TABLE 1-continued

| Ex. No | R | Compound name | HPLC time (min) | M+ |
|---|---|---|---|---|
| 15 | 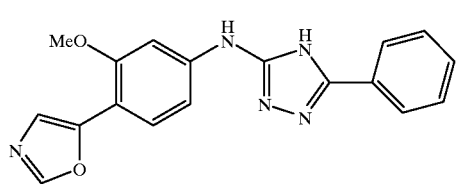 | N³-[3-Methoxy-4-(5oxazolyl)phenyl]-1-[4-(methylsulfonyl)phenyl]-1H-1,2,4-triazole-3,5-diamine | 3.296 | 427.23 |
| 16 | 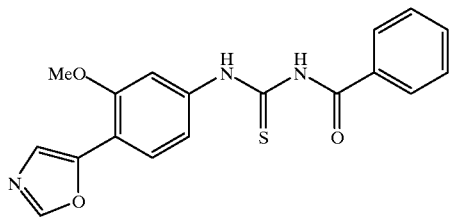 | 6-[3-[[3-Methoxy-4-(5-oxazolyl)phenyl]amino]-1H-1,2,4-triazol-1-yl]-1,3-dimethyl-2,4(1H,3H)-pyrimidinetrione | 3.280 | 411.25 |
| 17 | 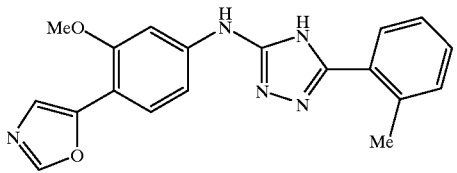 | 1-(2-Fluorophenyl)-N³-[3-methoxy-4-(5-oxazolyl)phenyl]-1H-1,2,4-triazole-3,5-diamine | 3.406 | 367.27 |

EXAMPLE 18

Preparation of N-[3-Methoxy-4-(5-oxazolyl)phenyl]-5-phenyl-1H-1,2,4-triazol-3-amine

Example 18, Part A

N-[[[3-Methoxy-4-(5-oxazolyl)phenyl]amino]thioxo]benzamide

To a solution of 5-(4-amino-2-methoxyphenyl)oxazole (400 mg, 2.10 mmol) in dichloromethane (15 mL) was added benzoyl isothiocyanate (0.38 mL, 2.77 mmol), and the resulting mixture was stirred at room temperature for 3 h. After the solvent was evaporated under vacuum, the residue was washed with diethyl ether to give the title compound 18A (697 mg, 94%) as a yellow solid. The product was 100% pure by LC/MS (retention time=4.32 min.; M+=354.14. Column: YMC S5 ODS 4.6×5.0 mm Ballistic. Solvent A=10% MeOH, 90% H₂O, 0.1% TFA; Solvent B=90% MeOH, 10% H₂O, 0.1% TFA).

Example 18, Part B

N-[3-Methoxy-4-(5-oxazolyl)phenyl]-5-phenyl-1H-1,2,4-triazol-3-amine

A mixture of 18A (150 mg, 0.424 mmol) and hydrazine monohydrate (78.0 mg, 1.56 mmol) in 2:3 THF/ethanol (25 mL) was heated at reflux for 20 h. After the solvent was removed under vacuum. the residue was purified by preparative HPLC, followed by neutralization, to give the title compound 18 (45.0 mg, 32%) as a white solid. The product was 100% pure by LC/MS (retention time=3.76 min.; M+=334.24. Column: YMC S5 ODS 4.6×5.0 mm Ballistic. Solvent A=10% MeOH, 90% H₂O, 0.1% TFA; Solvent B=90% MeOH, 10% H₂O, 0.1% TFA).

EXAMPLE 19

Preparation of N-[3-Methoxy-4-(5-oxazolyl)phenyl]-5-(2-methylphenyl)-1H-1,2,4-triazol-3-amine

Example 19 Part A

N-[[[3-Methoxy-4-(5-oxazolyl)phenyl]amino]thioxo]-2-methylbenzamide

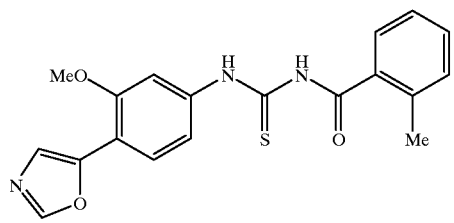

19A

To a solution of 5-(4-amino-2-methoxyphenyl)oxazole (200 mg, 1.05 mmol) in dichloromethane (10 mL) was added 2-methylbenzoyl isothiocyanate (0.19 mL, 1.26 mmol), and the resulting mixture was heated at reflux for 2 h. The precipitated product was collected by suction filtration and washed with diethyl ether to give the title compound 19A (368 mg, 95%) as a yellow solid. The product was 97% pure by LC/MS (retention time=4.28 min.; $M^+$=368.25. Column: YMC S5 ODS 4.6×5.0 mm Ballistic. Solvent A=10% MeOH, 90% $H_2O$, 0.1% TFA; Solvent B=90% MeOH, 10% $H_2O$, 0.1% TFA).

Example 19 Part B

N-[3-Methoxy-4-(5-oxazolyl)phenyl]-5-(2-methylphenyl)-1H-1,2,4-triazol-3-amine

A mixture of 19A (100 mg, 0.272 mmol) and hydrazine monohydrate (84.0 mg, 1.68 mmol) in 3:2 methanol/THF (25 mL) was subjected to the same procedure used in the preparation of 18 to give the title compound 19 (51.2 mg, 54%) as a white solid. The product was 99% pure by LC/MS (retention time=4.06 min.; $M^+$=348.26. Column: YMC S5 ODS 4.6×5.0 mm Ballistic. Solvent A=10% MeOH, 90% $H_2O$, 0.1% TFA; Solvent B=90% MeOH, 10% $H_2O$, 0.1% TFA).

EXAMPLE 20

Preparation of N-[3-Methoxy-4-(5-oxazolyl)phenyl]-5-(3-methylphenyl)-1H-1,2,4-triazol-3-amine

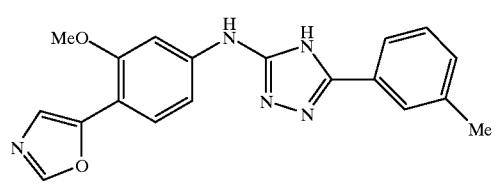

20

Example 20 Part A

N-[[[3-Methoxy-4-(5-oxazolyl)phenyl]amino]thioxo]-3-methylbenzamide

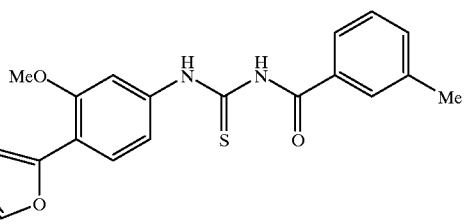

20A

To a solution of 5-(4-amino-2-methoxyphenyl)oxazole (200 mg, 1.05 mmol) in dichloromethane (10 mL) was added 3-methylbenzoyl isothiocyanate (0.19 mL, 1.24 mmol), and the resulting mixture was heated at reflux for 2 h. The product was collected by suction filtration and washed with diethyl ether to give 20A (370 mg, 96%) as a yellow solid. The product was 100% pure by LC/MS (retention time=4.70 min.; $M^+$=368.24. Column: YMC S5 ODS 4.6×5.0 mm Ballistic. Solvent A=10% MeOH, 90% $H_2O$, 0.1% TFA; Solvent B=90% MeOH, 10% $H_2O$, 0.1% TFA).

Example 20 Part B

N-[3-Methoxy-4-(5-oxazolyl)phenyl]-5-(3-methylphenyl)-1H-1,2,4-triazol-3-amine

A mixture of 20A (100 mg, 0.272 mmol) and hydrazine monohydrate (100 mg, 1.96 mmol) in 3:2 methanol/THF (25 mL) was subjected to the same procedure used in the preparation of 18 to give the title compound 20 (25.2 mg, 27%) as a white solid. The product was 100% pure by LC/MS (retention time=3.96 min.; $M^+$=348.28. Column: YMC S5 ODS 4.6×5.0 mm Ballistic. Solvent A=10% MeOH, 90% $H_2O$, 0.1% TFA; Solvent B=90% MeOH, 10% $H_2O$, 0.1% TFA).

EXAMPLE 21

Preparation of N-[3-Methoxy-4-(5-oxazolyl)phenyl]-5-phenyl-1,3,4-oxadiazol-2-amine

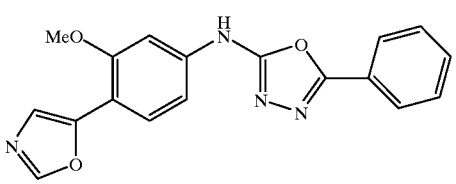

21

Example 21 Part A

Benzoic acid, 2-[[3-methoxy-4-(5-oxazolyl)phenyl]amino]carbonylhydrazide

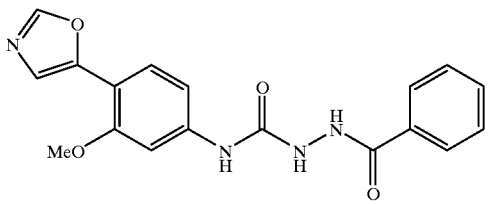

21A

An oven dry 100 mL flask was charged with 5-(4-amino-2-methoxyphenyl)oxazole (1 g, 5.26 mmol), 20 mL of anhydrous THF and carbonyldiimidazole (1.02 g, 6.31 mmol). The heterogeneous reaction mixture was stirred at room temperature for 6 hours. Benzoyl hydrazine (1.43 g, 10.52 mmol) and 4-dimethylaminopyridine (0.64 g, 5.26 mmol) were added and the reaction mixture was heated at 70° C. for 18 hours, cooled to room temperature, and the solid was filtered and washed with ethyl acetate. (Yield: 0.5 g, 27%) m.p. 231–233° C. Concentration of the filtrate and washing the resulting solid with ethyl acetate gives another batch (0.48 g, 26%) of the title compound 21A. $^1$H NMR (DMSO-$d_6$) δ10.31 (1H), 9.1 (1H), 8.35 (s, 1H), 8.30(s, 1H), 7.94 (d, 2H), 7.59–7.1 (m, 7H), 3.89 (s, 3H).

Example 21 Part B

N-[3-Methoxy-4-(5-oxazolyl)phenyl]-5-phenyl-1,3,4-oxadiazol-2-amine

A solution of 21A (0.15 g, 0.42 mmol) in acetonitrile (7 mL) was cooled to 0° C. and to it is sequentially added 1,2-dibromotetrachloroethane (0.15 g, 0.46 mmol), triphenylphosphine (0.245 g, 0.92 mmol) and triethyl amine (0.26 mL, 1.84 mmol). The reaction mixture was stirred for 18 hours at room temperature, refluxed for 2 hours, cooled to room temperature and purified by silica gel column chromatography using hexane-acetone (6:4, 500 mL) to yield the title compound 21 (0.09 g, 64%). m.p. 223–226° C. (LC/MS retention time=4.09 min.; M=335.20. Column: YMC S5 ODS 4.6×5.0 mm Ballistic. Solvent A=10% MeOH, 90% H$_2$O, 0.1% TFA; Solvent B=90% MeOH, 10% H$_2$O, 0.1% TFA).

EXAMPLE 22

Preparation of N-[3-Methoxy-4-(5-oxazolyl)phenyl]-5-phenyl-1,2,4-oxadiazol-3-amine

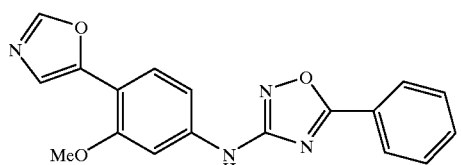

22

Example 22 Part A

Preparation of N-[[[3-Methoxy-4-(5-oxazolyl)phenyl]amino](methylthio)methylene]benzamide

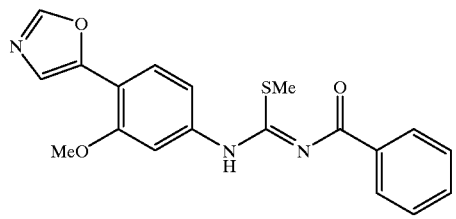

22A

To 0.1N NaOH (21.2 mL, 2.11 mmol) was sequentially added 18A (0.5 g, 1.41 mmol) and methyl iodide (0.1 mL, 1.7 mmol). The reaction mixture was stoppered and stirred for 18 hours at room temperature. The solid was filtered and dried to give 22A (0.51 g, 98%) which was carried over to the next step without further purification.

Example 22 Part B

Preparation of N-[[[3-Methoxy-4-(5-oxazolyl)phenyl]amino](methylthio)methylene]benzamide To a solution of 22A (0.3 g, 0.817 mmol) in 6 mL of EtOH was added hydroxylamine (50% solution in water, 76 μl, 1.22 mmol) and the reaction mixture was gradually warmed to 90° C. and held at that temperature for 1 hour. The reaction was cooled to room temperature and filtered to give the title compound 22 (0.2 g, 72%). m.p. 229–232. (LC/MS retention time=4.76 min.; M$^+$=335.23. Column: YMC S5 ODS 4.6×5.0 mm Ballistic. Solvent A=10% MeOH, 90% H$_2$O, 0.1% TFA; Solvent B=90% MeOH, 10% H$_2$O, 0.1% TFA).

EXAMPLE 23

Preparation of N-[3-Methoxy-4-(5-oxazolyl)phenyl]-5-phenyl-1,3,4-thiadiazol-2-amine

Example 23 Part A

Benzoic acid, 2-[[3-methoxy-4-(5-oxazolyl)phenyl]amino]thiocarbonylhydrazide

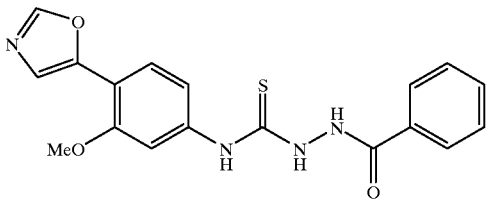

23A

To a solution of 1E in ethanol was added benzoylhydrazine at room temperature. The reaction mixture was refluxed for 2 h, cooled to room temperature and filtered to yield 23A as a solid (0.761 g, 96%). m.p. 204–205. $^1$H NMR (DMSO-$d_6$) δ10.57 (1H), 10.0 (brs, 2H), 8.4 (1H), 7.98 (s, 2H), 7.35–7.65 (m, 7H), 3.89 (s, 3H).

Example 23 Part B

N-[3-Methoxy-4-(5-oxazolyl)phenyl]-5-phenyl-1,3,4-thiadiazol-2-amine

To a solution of 23A in 5 mL of anhydrous toluene was added 78 μL of methanesulfonic acid and the contents were heated under reflux for 6 h. The reaction mixture was cooled to room temperature and 10 mL of water was added. The solid that was thrown out was filtered off and washed with water (10 mL). The filtrate was made basic using aq. ammonia. The resulting solid was filtered, washed with water and dried to yield the title compound 23 (0.02 g, 14%). (LC/MS retention time=4.40 min.; M$^+$=351.17. Column: YMC S5 ODS 4.6×5.0 mm Ballistic. Solvent A=10% MeOH, 90% H$_2$O, 0.1% TFA; Solvent B=90% MeOH, 10% H$_2$O, 0.1% TFA).

EXAMPLE 24

N-[3-[[3-Methoxy-4-(5-oxazolyl)phenyl]amino]-1-phenyl-1H-1,2,4-triazol-5-yl]acetamide

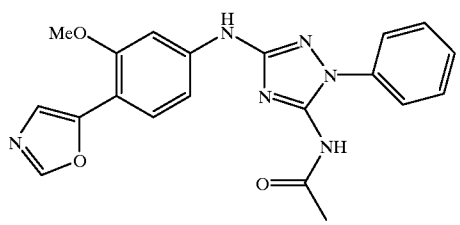

24

To a solution of 1 (50.0 mg, 0.144 mmol) in Dry THF (10 mL) was introduced a 1.0 M solution of lithium bis(trimethylsilyl)amide in THF (0.32 mL, 0.32 mmol) at −78° C. The solution was stirred for 20 min before acetyl chloride (12.3 μL, 0.173 mmol) was added. The mixture was stirred at −78° C. for one hour and then at RT for another hour. The reaction was quenched with water (10 mL), and the resulting solution was diluted with AcOEt (50 mL), washed with brine, and dried over anhydrous MgSO$_4$. Evaporation of solvent, followed by washing the residue with diethyl ether, provided the desired product (40.0 mg, 72% yield) as a pale yellow solid. (LC/MS; retention time=3.54 min.; M$^+$=350.17. Column: SHIMADZU 4.6×5.0 mm Ballistic. Solvent A=10% MeOH, 90% H$_2$O, 0.1% TFA; Solvent B=90% MeOH, 10% H$_2$O, 0.1%.

EXAMPLE 25

N$^3$-[3-Methoxy-4-(5-oxazolyl)phenyl]-1-(3-pyridinyl)-1H-1,2,4-triazol-3,5-diamine

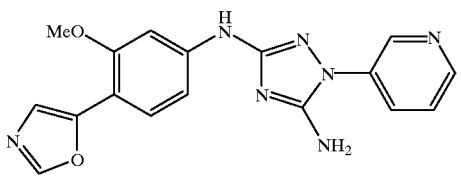

25

Example 25 Part A

3-Pyridinohydrazine

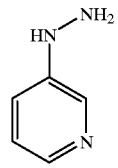

25A

To a solution of 3-aminopyridine (4.00 g, 42.5 mmol) in concentrated hydrochloric acid (25 mL) was added a solution of sodium nitrite (3.30 g, 46.4 mmol) in water (8 mL) at −5° C. over 10 min. The solution was stirred at 0° C. for 45 min and then to this solution was added a solution of Tin (II) chloride dihydrate in concentrated hydrochloric acid (12 mL) at −5° C. The resulting mixture was stirred at 0° C. for another hour. The solid that formed was collected by suction filtration and then placed in a beaker containing ice (20 g). To this mixture was added 50% KOH solution until it became basic (pH>10). The mixture was then extracted with AcOEt. The combined extract was dried over anhydrous MgSO$_4$. Evaporation of solvent under vacuum provided product 25A (1.34 g, 29% yield) as a yellow solid.

Example 25 Part B

N$^3$-[3-Methoxy-4-(5-oxazolyl)phenyl]-1-(3-pyridinyl)-1H-1,2,4-triazol-3,5-diamine A mixture of 1G (300.0 mg, 1.01 mmol), 1-ethyl-3-(3-dimethylaminopropyl)carbodiimide hydrochloride (387.0 mg, 2.02 mmol), and 3-pyridinehydrazine 25A (220.0 mg, 2.02 mmol) in DMF (10 mL) was subjected to the same procedure used in the preparation of example 2 to afford the desired product (36.0 mg, 10% yield) as a yellow solid. (LC/MS; retention time=3.01 min.; M$^+$=350.17. Column: SHIMADZU 4.6×5.0 mm Ballistic. Solvent A=10% MeOH, 90% H$_2$O, 0.1% TFA; Solvent B=90% MeOH, 10% H$_2$O, 0.1% TFA.

EXAMPLE 26

N³-[3-Methoxy-4-(-5-oxazolyl)phenyl]-1-(4-pyridinyl)-1H-1,2,4,-triazol-3,5-diamine

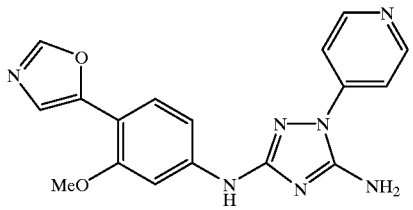

26

Example 26 Part A

4-Pyridinohydrazine

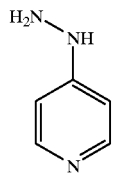

26A

A solution of 4-chloropyridine hydrochloride (500.0 mg, 3.33 mmol) and hydrazine monohydrate (1.67 g, 33.4 mmol) in ethanol (10 mL) was heated at 120° C. for 20 h. The solvent was evaporated under vacuum, and the residue was diluted with water (10 mL). To the resulting solution was added 50% NaOH solution until it became very basic. The solution was extracted with AcOEt. The combined extract was dried over anhydrous $MgSO_4$. Evaporation of solvent gave the desired product (238.0 mg, 66% yield) as a reddish solid.

Example 26

Part B, N³-[3-Methoxy-4-(-5-oxazolyl)phenyl]-1-(4-pyridinyl)-1H-1,2,4,-triazol-3,5-diamine A mixture of 1G (272.0 mg, 0.918 mmol), 1-ethyl-3-(3-dimethylaminopropyl)carbodiimide hydrochloride (352.0 mg, 1.84 mmol), and 4-pyridinehydrazine 26A (200.0 mg, 1.84 mmol) in DMF (10 mL) was heated at 60° C. for 16 h. The mixture was then diluted with AcOEt (80 mL), washed with water and brine, and concentrated under vacuum. The residue was subjected to preparative HPLC, followed by neutralization with 10% $NA_2CO_3$ solution, to afford the desired product (27.4 mg, 8% yield) as a yellow solid. (LC/MS; retention time=2.83 min.; M⁺=350.19. Column: SHIMADZU 4.6×5.0 mm Ballistic. Solvent A=10% MeOH, 90% $H_2O$, 0.1% TFA; Solvent B=90% MeOH, 10% $H_2O$, 0.1% TFA).

EXAMPLE 27

N³-[4-(1H-Imidazol-1-yl)-3-methoxyphenyl]-1-phenyl-1H-1,2,4-triazol-3,5-diamine

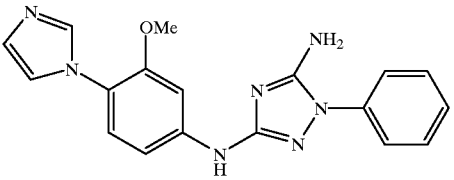

27

Example 27 Part A 1-(2-Methoxy-4-nitrophenyl)-1H-imidazole

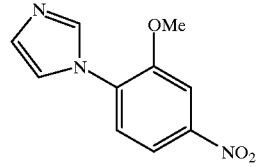

27A

A solution of 2-chloro-5-nitroanisole (1.0 g, 5.33 mmol), KOH (0.438 g, 7.81 mmol) and imidazole (1.45 g, 21.3 mmol) in DMSO (5 mL) was heated to 80° C. for three hours. The reaction mixture was poured into ice water. The precipitate was collected and washed with water to afford the title compound (0.75 g, 64%). ¹H NMR (CDCl₃): δ8.84 (1H, s), 8.07 (2H, m), 7.66 (1H, d), 7.55 (1H, s), 7.44 (1H, s), 4.09 (3H, s); LC-MS: m/z 220.07 (M+H)⁺

Example 27 Part B 1-(2-Methoxy-4-aminophenyl)-1H-imidazole

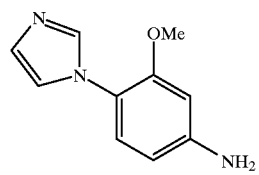

27B

A solution of 27A (0.70 g, 3.20 mmol) and $SnCl_2.H_2O$ (3.75 g, 16.6 mmol) in ethyl acetate (10 mL) and ethanol (5 mL) was stirred at 70° C. for 35 minutes. The resulting brown solution was poured into ice water and was neutralized with aqueous sodium bicarbonate. The suspension was extracted with three 30 mL portions of ethyl acetate. The combined organic phase was washed with brine (30 mL) and then dried over $MgSO_4$. Filtration and removal of solvent afforded a crude product which was purified by silica gel column chromatography to give the title compound (0.562 g, 93%). ¹H NMR (CDCl₃): δ7.23 (2H, d), 6.16 (2H, m), 6.10 (2H, s), 3.79 (3H, s); LC-MS: m/z 190.16 (M+H)⁺

Example 27 Part C

N-Cyano-N'-[4-(1H-imidazol-1-yl)-3-methoxyphenyl]carbamimidic acid phenyl ester

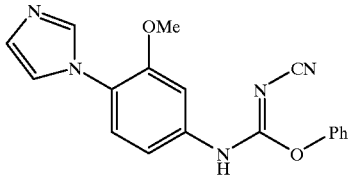

27C

A solution of 27B (0.500 g, 2.65 mmol) and diphenyl cyanocarbonimidate (0.630 g, 2.65 mmol) in N,N-dimethylacetamide (5 mL) was heated to 85° C. for 12 hrs. The reaction mixture was extracted with chloroform and washed with three 50 ml potions of water, 50 ml of brine and then dried over $Na_2SO_4$. Filtration and removal of solvent afforded a crude product which was purified by silica mgel column chromatography to give the title compound (0.375 g, 42%). $^1$H NMR ($CD_3OD$): δ7.76 (1H, s), 7.03–7.35 (9H, m), 6.95 (1H, s), 3.75 (3H, s); LC-MS: m/z 334.2 $(M+H)^+$

Example 27 Part D $N^3$-[4-(1H-Imidazol-1-yl)-3-methoxyphenyl]-1-phenyl-1H-1,2,4-triazol-3,5-diamine To a solution of 27C (150 mg 0.450 mmol) in N,N-dimethylacetamide (1 mL) was added phenylhydrazine (48 mg, 0.450 mmol). The reaction mixture was heated to 85° C. for 12 hrs. Phenylhydrazine (96 mg, 0.900 mmol) was added and the reaction mixture was heated to 100° C. for 4 hrs and cooled to RT. The reaction mixture was extracted with 100 ml of chloroform and washed with three 30 mL potions of water, 30 ml of brine and dried over $MgSO_4$. Filtration and removal of solvent afforded a crude product which was purified by silica gel column chromatography to give the title compound (29.7 mg, 19%). $^1$H NMR ($CD_3OD$): δ7.79 (1H, s), 7.12–7.64 (9H, m), 7.06 (1H, s), 3.87 (3H, s); LC-MS: m/z 348.24 $(M+H)^+$.

EXAMPLE 28

N-[3-Methoxy-4-(5-oxazolyl)phenyl]-5-(4-methylphenyl)-1H-1,2,4-triaziol-3-amine

28

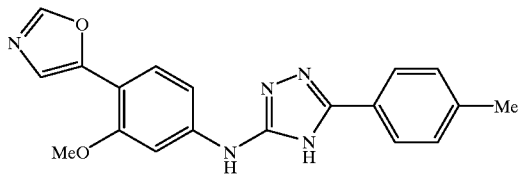

Example 28 Part A

N-(4-Methylbenzoyl)-N'-(3-methoxy-4-(5-oxazolyl)phenyl thiourea

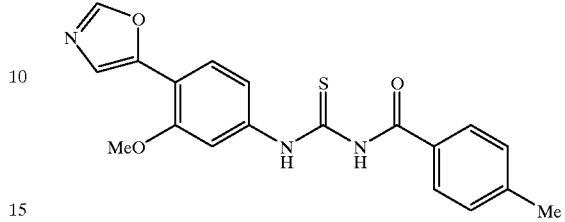

28A

To a solution of 1E (200 mg, 1.05 mmol) in dichloromethane (10 mL) was added 4-methylbenzoyl isothiocyanate (0.19 mL, 1.24 mmol), and the resulting mixture was heated at reflux for 2 h. The product was collected by suction filtration and washed with diethyl ether to give the title compound 28A 368 mg, 95% yield.

Example 28 Part B

N-[3-Methoxy-4-(5-oxazolyl)phenyl]-5-(4-methylphenyl)-1H-1,2,4-triaziol-3-amine

A mixture of 28A (100 mg, 0.272 mmol) and hydrazine monohydrate (69.5 mg, 1.36 mmol) in 3:2 methanol/THF (25 mL) was subjected to the same procedure used in the preparation of 18 to give the desired product (27.6 mg, 29% yield) as a white solid. (LC/MS; retention time=4.16 min.; $M^+$=348.25. Column: SHIMADZU 4.6×5.0 mm Ballistic. Solvent A=10% MeOH, 90% $H_2O$, 0.1% TFA; Solvent B=90% MeOH, 10% $H_2O$, 0.1% TFA).

EXAMPLE 29

N-[3-Methoxy-4-(5-oxazolyl)phenyl][1,1'-biphenyl]-3-amine

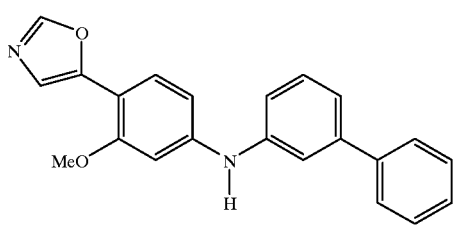

29

To an oven dry flask was sequentially added 1D (,0.978 g, 5.15 mmol), toluene (25 mL), 3-bromobiphenyl (1 g, 4.29 mmol), tris(dibenzylideneacetone)dipalladium (0.010 g, 0.010 mmol), R(+)BINAP (0.022 g, 0.032 mmol) and sodium tert-butoxide (0.577 g, 6.0 mmol) and the reaction mixture was heated at 80° C. for 5 hours. The reaction mixture was concentrated under reduced pressure and to the residue that is obtained is added 60 mL of dichloromethane and the contents are filtered over a thin pad of celite. The filtrate was concentrated under reduced pressure and purified by silica gel column chromatography using hexane-ethyl acetate (3:2, 500 mL). To the foamy solid that is obtained was added HCl in dioxane. The contents are concentrated under reduced pressure and the oil that is obtained was crystallized from acetone to yield the title compound (0.16 g, 11%). m.p. 171–173° C. (LC/MS retention time=8.87 min.; M+=343.23 Column: YMC S5 ODS 4.6×5.0 mm Ballistic. Solvent A=10% MeOH, 90% H₂O, 0.1% TFA; Solvent B=90% MeOH, 10% H₂O, 0.1% TFA).

EXAMPLE 30

N-[3-Methoxy-4-(5-oxazolyl)phenyl]-5-phenyl-1,2,4-thiadiazol-3-amine

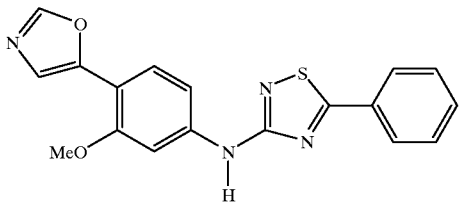

30

To a solution of benzamidoxime (0.293 g, 2.15 mmol) in 20 mL of chloroform was added 1E (1 g, 4.31 mmol) and the contents heated under reflux for 18 hours. The solid that separates out was filtered and dried to yield the title compound (0.2 g, 13%). m.p. 260–261° C. (LC/MS retention time=4.93 min.; M+=351.20 Column: YMC S5 ODS 4.6× 5.0 mm Ballistic. Solvent A=10% MeOH, 90% H₂O, 0.1% TFA; SolventB=90% MeOH, 10% H₂O, 0.1% TFA).

EXAMPLE 31

N-[3-Methoxy-4-(5-oxazolyl)phenyl]-5-phenyl-3-isoxazolamine

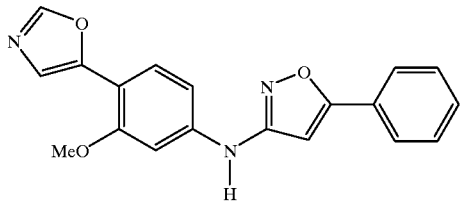

31

To an oven dry flask was added acetophenone (0.4 mL, 3.33 mmol) followed by 10 mL of anhydrous DMF. The flask was cooled to 0° C. and to it was added sodium hydride (0.084 g, 3.33 mmol) over a 10 min. The flask was stirred at RT for 10 min. 1E (0.772 g, 3.33 mmol) was added over a 10 min. period and the reaction mixture was stirred at RT for 1 hour. Iodomethane (0.2 mL, 3.33 mmol) was added and the reaction mixture was stirred at RT for an additional hour, concentrated under reduced pressure and partitioned between ethyl acetate and water. The ethyl acetate layer was dried over sodium sulfate and concentrated under reduced pressure to yield 3-[[3-Methoxy-4-(5-oxazolyl)phenyl]amino]-3-(methylthio)-1-phenyl-2-propen-1-one (1.3 g), which was used for the subsequent step without further purification. To a solution of 3-[[3-Methoxy-4-(5-oxazolyl) phenyl]amino]-3-(methylthio)-1-phenyl-2-propen-1-one (1.2 g, 3.32 mmol) in 10 mL of ethanol was added hydroxylamine (50% solution in water, 0.3 mL, 4.98 mmol) and the contents refluxed for 4 hours. The reaction mixture was partitioned between ethyl acetate and water. The ethyl acetate layer was left at RT overnight and the solid that separates out (700 mgs) was filtered. 100 mgs of this solid was purified using preparative HPLC (YMC S5 ODS 30×250 mm Ballistic. Solvent A=10% MeOH, 90% H₂O, 0.1% TFA; Solvent B=90% MeOH, 10% H₂O, 0.1% TFA). The fraction having a retention time of 4.61 min. was collected, concentrated under reduced pressure, neutralized with 10% aqueous sodium carbonate and extracted into ethyl acetate. The ethyl acetate layer was concentrated to yield 0.015 mgs of the title compound. m.p. 173–175° C. (LC/MS retention time=4.61 min.; M+=334.22 Column: YMC S5 ODS 4.6×5.0 mm Ballistic. Solvent A=10% MeOH, 90% H₂O, 0.1% TFA; Solvent B=90% MeOH, 10% H₂O, 0.1% TFA).

EXAMPLE 32

N-[3-Methoxy-4-(5-oxazolyl)phenyl]-2-phenyl-5-thiazolamine

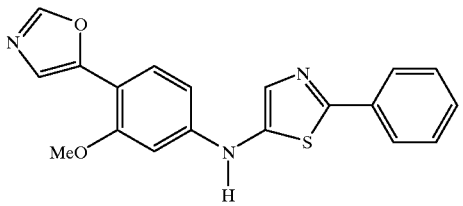

32

Example 32 Part A

N-[2-[[3-Methoxy-4-(5-oxazolyl)phenyl]amino]-2-oxoethyl]benzamide

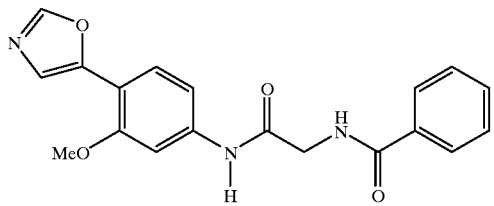

32A

To a solution of hippuric acid (0.942 g, 5.26 mmol) in 25 mL of anhydrous THF was added 1,1'-carbonyldiimidazole (0.938 g, 5.78 mmol). The reaction mixture was stirred at RT for 20 min. 1D (1.0 g, 5.26 mmol) was added and the reaction mixture was stirred at RT for 1 hour. The solid that separates out was filtered to yield the title compound (1.1 g). m.p. 243–245° C.

Example 32 Part B

N-[3-Methoxy-4-(5-oxazolyl)phenyl]-2-phenyl-5-thiazolamine

To a solution of N-[2-[[3-Methoxy-4-(5-oxazolyl)phenyl] amino]-2-oxoethyl]benzamide (0.630 g, 1.79 mmol) in 15 mL of pyridine was added Lawesson's reagent (0.798 g, 1.96 mmol) and the contents heated at 100° C. for 18 hours. The reaction mixture was cooled to RT and partitioned between ethyl acetate and saturated aqueous sodium bicarbonate. The ethyl acetate layer was dried over sodium sulfate, concentrated under reduced pressure and purified using silica gel column chromatography (hexane:acetone, 3:2, 400 mL) to yield 32 (0.380 g). m.p. 142–144° C. (LC/MS retention time=4.7 min.; M+=350.22 Column: YMC S5 ODS 4.6×5.0 mm Ballistic. Solvent A=10% MeOH, 90% H₂O, 0.1% TFA; Solvent B=90% MeOH, 10% H₂O, 0.1% TFA).

EXAMPLE 33

N-[3-Methoxy-4-(5-oxazolyl)phenyl]-4-phenyl-2-thiazolamine

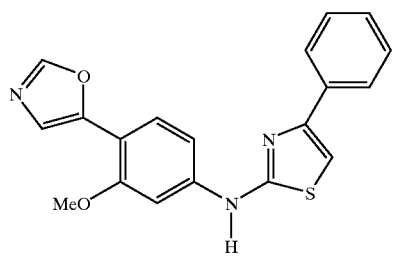

Example 33 Part A

[3-Methoxy-4-(5-oxazolyl)phenyl]thiourea

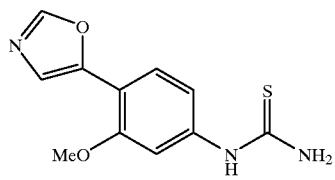

To a solution of 1E (0.27 g, 1.16 mmol) in 5 mL of dioxane was added ammonia (0.5 molar solution in dioxane, 4.6 mL, 2.32 mmol) and the contents stirred at RT for 30 min. The reaction mixture was concentrated under reduced pressure to yield 0.3 g of the title compound. (LC/MS retention time=2.52 min.; M+=250.11 Column: YMC S5 ODS 4.6×5.0 mm Ballistic. Solvent A=10% MeOH, 90% H₂O, 0.1% TFA; Solvent B=90% MeOH, 10% H₂O, 0.1% TFA).

Example 33 Part B

N-[3-Methoxy-4-(5-oxazolyl)phenyl]-4-phenyl-2-thiazolamine

To a solution of 33A (0.3 g, 1.2 mmol) in 10 mL of ethanol was added phenacyl bromide (0.24 g, 1.2 mmol) and the contents refluxed for 18 hours. The solid that separates out was filtered, transferred into a test-tube and washed with 10 mL of aqueous ammonia, filtered and dried to yield 0.080 g of the title compound. m.p. 193–195° C. (LC/MS retention time=4.82 min.; M+=350.17 Column: YMC S5 ODS 4.6× 5.0 mm Ballistic. Solvent A 10% MeOH, 90% H₂O, 0.1% TFA; Solvent B=90% MeOH, 10% H₂O, 0.1% TFA).

EXAMPLE 34

N-[3-Methoxy-4-(5-oxazolyl)phenyl]-5-phenyl-2-oxazolamine

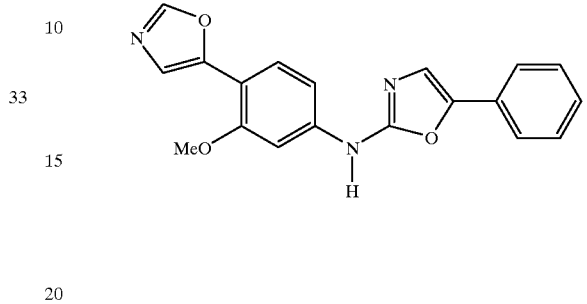

To a solution of 1E (1.0 g, 4.34 mmol) in 20 mL of dichloromethane was added phenacyl azide (0.7 g, 4.34 mmol) followed by triphenylphosphine (1.14 g, 4.34 mmol). The reaction mixture was stirred overnight at RT and the solid that separates out is filtered and washed with dichloromethane to yield the 1.0 g of the title compound. m.p. 212–215° C. (LC/MS retention time=4.61 min.; M+=334.22 Column: YMC S5 ODS 4.6×5.0 mm Ballistic. Solvent A=10% MeOH, 90% H₂O, 0.1% TFA; Solvent B=90% MeOH, 10% H₂O, 0.1% TFA).

EXAMPLES 35 TO 78

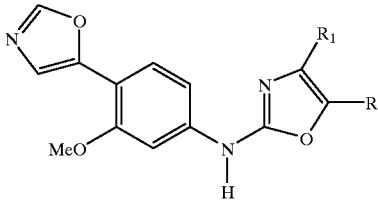

Compounds 35 to 78 were prepared from 1E by a route analogous to that used in example 34, by replacing phenacyl azide with an appropriately substituted azide. The isothiocyanate 1E and the appropriately substituted azide and a phosphine such as triphenylphosphine, are dissolved in a solvent such as 1,4-dioxane, 1,2-dimethoxyethane, tetrahydrofuran, 1,2 dichloroethane or toluene and stirred at a temperature from room temperature to 120° C. for a period of 15 minutes to 24 h. It has been observed that the reaction generally proceeds in higher yield when the reaction is conducted at a temperature between 65 and 110° C. which is conveniently maintained by the boiling point of the chosen solvent. When the reaction is conducted at a temperature between 65 and 110° C. the time for completion of the reaction is usually reduced to between 15 min and 1 h. Azides can be made by one of the many methods outlined in scheme 15. The compounds of these examples have structures outlined in Table 2 below.

TABLE 2*

| Example | R | R₁ | Name | HPLC time (min) | M⁺ |
|---|---|---|---|---|---|
| 35 | phenyl | Me | N-[3-Methoxy-4-(5-oxazolyl)phenyl]-4-methyl-5-phenyl-2-oxazolamine | 4.73 | 348.26 |
| 36 | 3-methoxyphenyl | H | N-[3-Methoxy-4-(5-oxazolyl)phenyl]-5-(3-methoxyphenyl)-2-oxazolamine | 4.30 | 364.25 |
| 37 | 2-pyridinyl | H | N-[3-Methoxy-4-(5-oxazolyl)phenyl]-5-(2-pyridinyl)-2-oxazolamine | 3.3 | 335.20 |
| 38 | tetrahydro-2-furanyl | H | N-[3-Methoxy-4-(5-oxazolyl)phenyl]-5-(tetrahydro-2-furanyl)-2-oxazolamine | 3.39 | 328.21 |
| 39 | 2-methoxyphenyl | H | N-[3-Methoxy-4-(5-oxazolyl)phenyl]-5-(2-methoxyphenyl)-2-oxazolamine | 4.63 | 364.28 |
| 40 | 4-methoxyphenyl | H | N-[3-Methoxy-4-(5-oxazolyl)phenyl]-5-(4-methoxyphenyl)-2-oxazolamine | 4.48 | 364.29 |
| 41 | 4-methylphenyl | H | N-[3-Methoxy-4-(5-oxazolyl)phenyl]-5-(4-methylphenyl)-2-oxazolamine | 4.87 | 348.47 |
| 42 | 3-methylphenyl | H | N-[3-Methoxy-4-(5-oxazolyl)phenyl]-5-(3-methylphenyl)-2-oxazolamine | 4.71 | 348.26 |
| 43 | 2-methylphenyl | H | N-[3-Methoxy-4-(5-oxazolyl)phenyl]-5-(2-methylphenyl)-2-oxazolamine | 4.90 | 348.24 |
| 44 | 2,3-dihydro-1,4-benzodioxin-6-yl | H | 5-(2,3-Dihydro-1,4-benzodioxin-6-yl)-N-[3-methoxy-4-(5-oxazolyl)phenyl]-2-oxazolamine | 4.20 | 392.22 |
| 45 | 4-(diethylamino)phenyl | H | 5-[4-(Diethylamino)phenyl]-N-[3-methoxy-4-(5-oxazolyl)phenyl]-2-oxazolamine | 3.43 | 405.22 |

TABLE 2*-continued

| Example | R | R₁ | Name | HPLC time (min) | M⁺ |
|---|---|---|---|---|---|
| 46 | 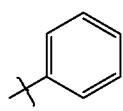 | Et | 4-Ethyl-N-[3-methoxy-4-(5-oxazolyl)phenyl]-5-phenyl-2-oxazolamine | 4.50 | 362.15 |
| 47 | 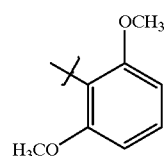 | H | 5-(2,6-Dimethoxyphenyl)-N-[3-methoxy-4-(5-oxazolyl)phenyl]-2-oxazolamine | 3.86 | 394.19 |
| 48 | 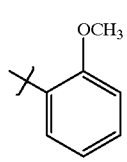 | Me | N-[3-Methoxy-4-(5-oxazolyl)phenyl]-5-(2-methoxyphenyl)-4-methyl-2-oxazolamine | 4.20 | 378.26 |
| 49 | 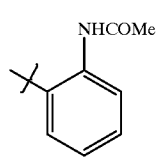 | H | N-[2-[2-[[3-Methoxy-4-(5-oxazolyl)phenyl]amino]-5-oxazolyl]phenyl]-N-acetamide | 3.65 | 391.24 |
| 50 | 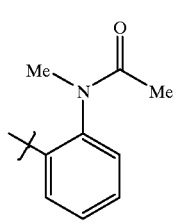 | H | N-[2-[2-[[3-Methoxy-4-(5-oxazolyl)phenyl]amino]-5-oxazolyl]phenyl]-N-methylacetamide | 4.28 | 405.25 |
| 51 | 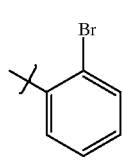 | H | 5-(2-Bromophenyl)-N-[3-methoxy-4-(5-oxazolyl)phenyl]-2-oxazolamine | 4.56 | 412.13 |
| 52 | Me |  | N-[3-Methoxy-4-(5-oxazolyl)phenyl]-5-methyl-4-phenyl-2-oxazolamine | 4.77 | 348.25 |
| 53 | 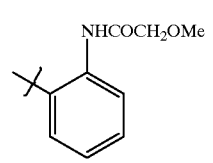 | H | 2-Methoxy-N-[2-[2-[[3-methoxy-4-(5-oxazolyl)phenyl]amino]-5-oxazolyl]phenyl]acetamide | 3.80 | 421.20 |

TABLE 2*-continued

| Example | R | R₁ | Name | HPLC time (min) | M⁺ |
|---|---|---|---|---|---|
| 54 | (morpholinomethyl-C(O)NH- on phenyl) | H | N-[2-[2-[[3-Methoxy-4-(5-oxazolyl)phenyl]amino]-5-oxazolyl)phenyl]-4-morpholineacetamide | 3.33 | 476.22 |
| 55 | (MeN(Me)-C(O)-CH₂-OMe on phenyl) | H | 2-Methoxy-N-[2-[2-[[3-methoxy-4-(5-oxazolyl)phenyl]amino]-5-oxazolyl]phenyl]-N-methylacetamide | 3.37 | 435.24 |
| 56 | (OBn on phenyl) | H | N-[3-Methoxy-4-(5-oxazolyl)phenyl]-5-[2-(phenylmethoxy)phenyl]-2-oxazolamine | 4.62 | 440.18 |
| 57 | (CO₂Et on phenyl) | H | 2-[2-[[3-Methoxy-4-(5-oxazolyl)phenyl]amino]-5-oxazolyl]benzoic acid ethyl ester | 4.12 | 406.16 |
| 58 | (tetrahydrofuran-3-yl-O-C(O)-NH- on phenyl) | H | [2-[2-[[3-Methoxy-4-(5-oxazolyl)phenyl]amino]-5-oxazolyl]phenyl]carbamic acid tetrahydro-3-furanyl ester | 3.76 | 463.21 |
| 59 | (tetrahydrofuran-3-yl-O-C(O)-N(Me)- on phenyl) | H | [2-[2-[[3-Methoxy-4-(5-oxazolyl)phenyl]amino]-5-oxazolyl]phenyl]methylcarbamic acid tetrahydro-3-furanyl ester | 3.93 | 477.29 |

TABLE 2*-continued

| Example | R | R₁ | Name | HPLC time (min) | M⁺ |
|---|---|---|---|---|---|
| 60 | (1-(2-substituted-phenyl)-oxazolidin-2-one) | H | 3-[2-[2-[[3-Methoxy-4-(5-oxazolyl)phenyl]amino]-5-oxazolyl]phenyl]-2-oxazolidinone | 3.46 | 419.20 |
| 61 | (tetrahydrofuran-3-yl N-methyl-N-(2-substituted-phenyl)carbamate) | H | [2-[2-[[3-Methoxy-4-(5-oxazolyl)phenyl]amino]-5-oxazolyl]phenyl]methyl-carbamic acid phenylmethyl ester | 4.34 | 497.28 |
| 62 | (N,N-dimethyl-2-substituted-benzamide) | H | 2-[2-[[3-Methoxy-4-(5-oxazolyl)phenyl]amino]-5-oxazolyl]-N,N-dimethylbenzamide | 3.02 | 405.22 |
| 63 | (2-furanyl) | H | 5-(2-Furanyl)-N-[3-methoxy-4-(5-oxazolyl)phenyl]-2-oxazolamine | 4.05 | 324.18 |
| 64 | (1-(benzyloxycarbonyl)pyrrolidin-2-yl) | H | 2-[2-[[3-Methoxy-4-(5-oxazolyl)phenyl]amino]-5-oxazolyl]-1-pyrrolidinecarboxylic acid phenylmethyl ester | 3.40 | 461.26 |
| 65 | (N-ethyl-N-(2-substituted-phenyl)-2-morpholinoacetamide) | H | N-[2-[2-[[3-Methoxy-4-(5-oxazolyl)phenyl]amino]-5-oxazolyl]phenyl]-N-ethyl-4-morpholineacetamide | 3.00 | 504.31 |

TABLE 2*-continued

| Example | R | R₁ | Name | HPLC time (min) | M⁺ |
|---|---|---|---|---|---|
| 66 | 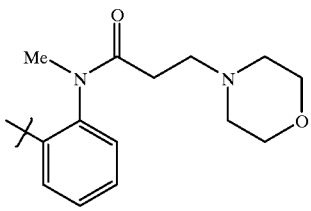 | H | N-[2-[2-[[3-Methoxy-4-(5-oxazolyl)phenyl]amino]-5-oxazolyl]phenyl]-N-methyl-4-morpholinepropanamide | 1.60*ᵃ | 504.27 |
| 67 | 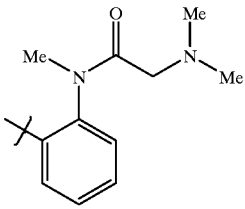 | H | N-[2-[2-[[3-Methoxy-4-(5-oxazolyl)phenyl]amino]-5-oxazolyl]phenyl]-N,N2,N2-trimethylglycinamide | 1.56*ᵃ | 448.27 |
| 68 | 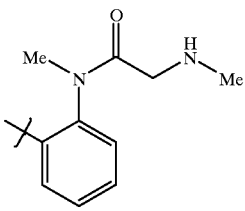 | H | N-[2-[2-[[3-Methoxy-4-(5-oxazolyl)phenyl]amino]-5-oxazolyl]phenyl]-N,N2-dimethylglycinamide | 1.57*ᵃ | 434.27 |
| 69 | 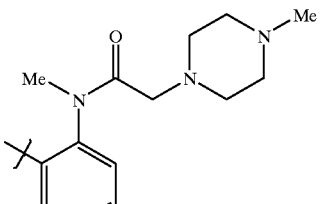 | H | N-[2-[2-[[3-Methoxy-4-(5-oxazolyl)phenyl]amino]-5-oxazolyl]phenyl]-N,4-dimethyl-1-piperazineacetamide | 1.61*ᵃ | 503.27 |
| 70 | 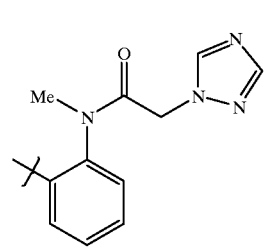 | H | N-[2-[2-[[3-Methoxy-4-(5-oxazolyl)phenyl]amino]-5-oxazolyl]phenyl]-N-methyl-1H-1,2,4-triazole-1-acetamide | 1.71*ᵃ | 427.26 |
| 71 | 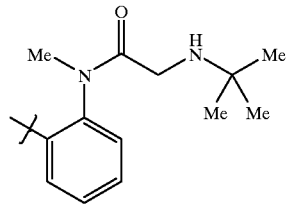 | H | N2-(1,1-Dimethylethyl)-N-[2-[2-[[3-methoxy-4-(5-oxazolyl)phenyl]amino]-5-oxazolyl]phenyl]-N-methylglycinamide | 3.47 | 476.29 |

TABLE 2*-continued

| Example | R | R₁ | Name | HPLC time (min) | M⁺ |
|---|---|---|---|---|---|
| 72 | (structure) | H | N-[2-[2-[[3-Methoxy-4-(5-oxazolyl)phenyl]amino]-5-oxazolyl]phenyl]-N-methyl-N2-(1-methylethyl)glycinamide. | 3.47 | 462.25 |
| 73 | (structure) | H | N-[2-[2-[[3-Methoxy-4-(5-oxazolyl)phenyl]amino]-5-oxazolyl]phenyl]-N-methyl-1H-imidazole-1-acetamide | 1.57*ᵃ | 471.32 |
| 74 | (structure) | H | N-[2-[2-[[3-Methoxy-4-(5-oxazolyl)phenyl]amino]-5-oxazolyl]phenyl]-N-methyl-1H-pyrazole-1-acetamide | 3.94 | 471.31 |
| 75 | (structure) | H | N-[2-[2-[[3-Methoxy-4-(5-oxazolyl)phenyl]amino]-5-oxazolyl]phenyl]-N-methyl-2H-1,2,3-triazole-2-acetamide | 3.41 | 472.24 |
| 76 | (structure) | H | N-[2-[2-[[3-Methoxy-4-(5-oxazolyl)phenyl]amino]-5-oxazolyl]phenyl]-N-methyl-1H-1,2,3-triazole-1-acetamide | 3.25 | 472.25 |
| 77 | (structure) | H | N-[2-[2-[[3-Methoxy-4-(5-oxazolyl)phenyl]amino]-5-oxazolyl]phenyl]-N,α-dimethyl-4-morpholineacetamide | 1.47*ᵃ | 504.50 |

TABLE 2*-continued

| Example | R | R₁ | Name | HPLC time (min) | M⁺ |
|---|---|---|---|---|---|
| 78 | 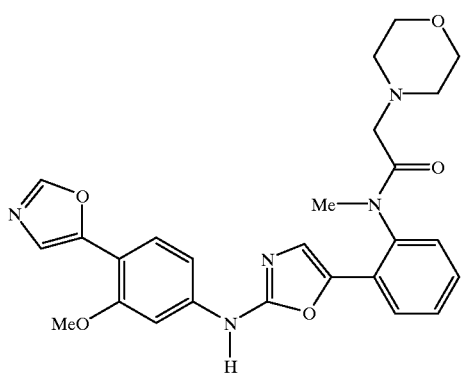 | H | N-[2-[2-[[3-Methoxy-4-(5-oxazolyl)phenyl]amino]-5-oxazolyl]phenyl]-N-methyl-2-pyrrolidinecarboxamide | 1.60*a | 460.35 |

*The HPLC conditions for the examples listed above is as follows: Column: YMC S5 ODS 4.6 × 5.0 mm Ballistic. Solvent A = 10% MeOH, 90% H₂O, 0.1% TFA; Solvent B = 90% MeOH, 10% H₂O, 0.1% TFA. Flow rate: 4 mL/min. Gradient: 4 min.
*aColumn: YMC S50 Turbopac Pro 4.6 × 5.0 mm Ballistic. Solvent A = 10% MeOH, 90% H₂O, 0.1% TFA; Solvent B = 90% MeOH, 10% H₂O, 0.1% TFA. Flow rate: 4 mL/min. Gradient: 2 min.

EXAMPLE 79

N-[2-[2-[[3-Methoxy-4-(5-oxazolyl)phenyl]amino]-5-oxazolyl]phenyl]-N-methyl-4-morpholineacetamide

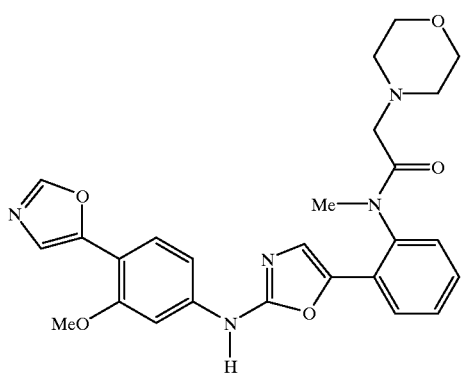

Example 79 Part A

2-Bromo-N-(2-bromophenyl)acetamide

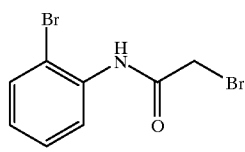

To a solution of 2-bromoaniline (2.0 g, 11.63 mmol) in 25 mL of dichloromethane was added pyridine (1.13 mL, 13.95 mmol). The solution was cooled to 0° C. and bromoacetyl chloride (1.01 mL, 12.79 mmol) was added over a 5 min. period. The cooling bath was removed and the reaction mixture was stirred at RT for 90 min and partitioned between 1N HCl and dichloromethane. The dichloromethane layer was successively washed with saturated aqueous sodium carbonate, brine, dried over sodium sulfate and concentrated to yield 2.9 g of the title compound, which was used as such for the subsequent step without further purification.

Example 79 Part B

N-(2-Bromophenyl)-4-morpholineacetamide

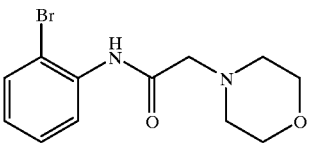

To a solution of 79A (2.9 g, 9.8 mmol) in 10 mL of anhydrous DMF was added triethylamine (2.1 mL, 14.7 mmol) and morpholine (1.3 mL, 14.7 mmol). The reaction mixture was stirred at RT for 18 hours, concentrated under reduced pressure and partitioned between ethyl acetate and water. The ethyl acetate layer was dried over sodium sulfate and concentrated under reduced pressure to yield 3.1 g of the title compound, which was used as such for the subsequent step without further purification.

Example 79 Part C

N-(2-Bromophenyl)-N-methyl-4-morpholineacetamide

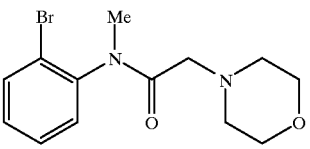

To a solution of 79B (1.5 g, 4.70 mmol) in 10 mL of anhydrous DMF was added sodium hydride (95%, 0.154 g, 6.11 mmol) over a 5 min. period at RT. After 10 min. iodomethane (0.4 mL, 6.11 mmol) was added. After 30 min. at RT the reaction mixture was concentrated under reduced pressure, partitioned between ethyl acetate and 1N HCl. The HCl layer was made basic using 1N NaOH and extracted into ethyl acetate. The ethyl acetate layer was washed with water, dried over sodium sulfate and concentrated under reduced pressure to yield 1.1 g of the title compound, which was used as such for the subsequent step without further purification.

Example 79 Part D

N-[2-(1-Ethoxy-1-ethenyl)phenyl]-N-methyl-4-morpholineacetamide

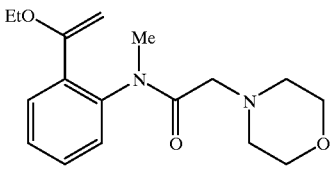

79D

To a solution of 79C (1.18 g, 3.75 mmol) in 10 mL of dioxane was added tributyl(1-ethoxyvinyl)tin (1.33 mL, 3.93 mmol) and dichlorobis(triphenylphosphine)palladium (II) (0.138 g, 0.18 mmol). The reaction mixture was heated at 100° C. in a sealed tube for 18 hours, cooled to RT and filtered over a thin pad of celite®. The filtrate was concentrated under reduced pressure and purified by silica gel column chromatography to yield the title compound as an oil (0.928 g, 81%) (LC/MS retention time=2.63 min.; M$^+$=305.22 Column: YMC S5 ODS 4.6×5.0 mm Ballistic. Solvent A=10% MeOH, 90% H$_2$O, 0.1% TFA; Solvent B=90% MeOH, 10% H$_2$O, 0.1% TFA).

Example 79 Part E

N-[2-(Azidoacetyl)phenyl]-N-methyl-4-morpholineacetamide

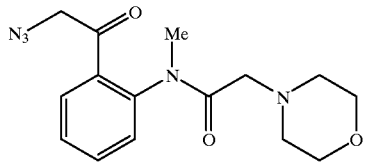

79E

To a solution of 79D (0.928 g, 3.05 mmol) in THF (10 mL) and water (2 mL) was added N-bromosuccinimide, (0.543 g, 3.05 mmol) and the contents stirred at RT for 5 to 10 min to yield N-[2-(Bromoacetyl)phenyl]-N-methyl-4-morpholineacetamide. Sodium azide (0.198 g, 3.05 mmol) was added and the reaction mixture stirred at RT for 5 to 10 min., concentrated under reduced pressure and partitioned between dichloromethane and water. The dichloromethane layer was dried over sodium sulfate, concentrated under reduced pressure to yield the title compound (0.673 g) which was used as such for the subsequent step without further purification.

Example 79

Part F, N-[2-[2-[[3-Methoxy-4-(5-oxazolyl)phenyl]amino]-5-oxazolyl]phenyl]-N-methyl-4-morpholineacetamide To a solution of 1E (0.250 g, 1.07 mmol) in 10 mL of dioxane was added 79E (0.673 g, 2.1 mmol) followed by triphenylphosphine (0.556 g, 2.1 mmol). The reaction mixture was placed in an oil bath preheated to 80° C. stirred at RT for 0.5 hour cooled to room temperature the solvent evaporated and the residue partitioned between 1N HCl and dichloromethane. The HCl layer was cooled to 0° C. and made basic using 20% aqueous potassium hydroxide and extracted into ethyl acetate. The ethyl acetate layer was dried over sodium sulfate, concentrated under reduced pressure and purified by silica gel column chromatography to yield 0.110 g, of the title compound as a solid melting at 179–181° C. (LC/MS retention time=2.83 min.; M$^+$=490.22 Column: YMC S5 ODS 4.6×5.0 mm Ballistic. Solvent A=10% MeOH, 90% H$_2$O, 0.1% TFA; Solvent B=90% MeOH, 10% H$_2$O, 0.1% TFA).

EXAMPLE 80

2-[2-[[3-Methoxy-4-(5-oxazolyl)phenyl]amino]-5-oxazolyl]benzoic acid

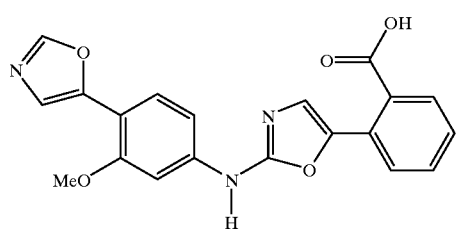

80

To a solution of 57 (0.15 g, 0.37 mmol) in 3 mL of DMSO was added lithium hydroxide (0.018 g, 0.77 mmol) and the contents heated at 100° C. for 1 hour. The reaction mixture was cooled to RT and partitioned between water and ethyl acetate. The aqueous layer was bought to pH 6 using 1N HCl. The solid that separates out was filtered and dried to yield the title compound (0.65 g). m.p. 271–274° C. (LC/MS retention time=3.75 min.; M$^+$=378.23 Column: YMC S5 ODS 4.6×5.0 mm Ballistic. Solvent A=10% MeOH, 90% H$_2$O, 0.1% TFA; Solvent B=90% MeOH, 10% H$_2$O, 0.1% TFA).

EXAMPLE 81

N-[3-Methoxy-4-(5-oxazolyl)phenyl]-5-(3-nitrophenyl)-2-oxazolamine

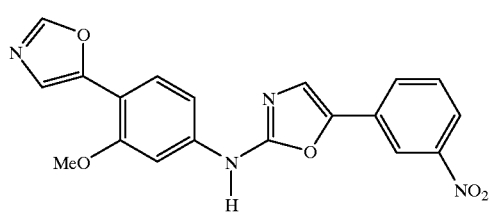

81

Example 81 Part A

N-[3-Methoxy-4-(5-oxazolyl)phenyl]-N'-[2-(3-nitrophenyl)-2-oxoethyl]thiourea

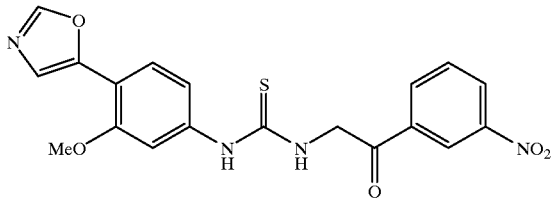

81A

To a solution of 1E (0.2 g, 0.86 mmol) in 5 mL of anhydrous dioxane was sequentially added 3-nitrophenacylamine hydrochloride (0.205 g, 0.94 mmol) and triethylamine (0.13 mL, 0.94 mmol). The reaction mixture was refluxed for 2 hours, concentrated under reduced pressure and partitioned between ethyl acetate and water. The ethyl acetate layer was dried over sodium sulfate and concentrated under reduced pressure to yield 0.35 g of a foamy solid, which was used as such for the subsequent step without further purification.

Example 81 Part B

N-[3-Methoxy-4-(5-oxazolyl)phenyl]-5-(3-nitrophenyl)-2-oxazolamine

To a solution of 81A (0.167 g, 0.4 mmol) in 10 mL of anhydrous dioxane was added dicyclohexylcarbodiimide (0.125 g, 0.6 mmol) and the contents refluxed for 5 hours. The reaction mixture was concentrated and 20 mL of ethyl acetate was added. The solid that precipitated was filtered and dried to yield 0.055 g of the title compound melting at 279–281° C. (LC/MS retention time=4.67 min.; $M^+$=379.33 Column: YMC S5 ODS 4.6×5.0 mm Ballistic. Solvent A=10% MeOH, 90% $H_2O$, 0.1% TFA; Solvent B=90% MeOH, 10% $H_2O$, 0.1% TFA).

EXAMPLE 82

2-[2-[[3-Methoxy-4-(5-oxazolyl)phenyl]amino]-5-oxazolyl]-N,N-dimethylbenzamide

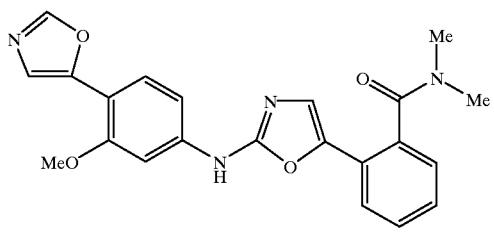

82

Example 82 Part A 2-(1-Ethoxyethenyl)-N,N-dimethylbenzamide

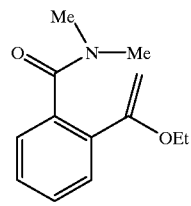

82A

To a solution of 2-bromobenzoyl chloride (1.02 g, 4.51 mmol) in anhydrous dioxane was added trimethyl(1-ethoxylvinyl)tin (1.61 ml, 4.73 mmol) and palladium bistriphenyl-phosphine chloride (159 mg, 0.23 mmol). The mixture was stirred in a sealed pressure tube at 100° C. for overnight. After cooling at RT, this mixture was diluted with EtOAc (60 ml), then filtered through a thin celite pad, which was washed with EtOAc (3×30 ml). The organic solution was concentrated in vacuo. The residue was purified by chromatography with silica gel (40%AcOEt/hexane) to afford 82A (850 mg, 86%).

hu 1H NMR ($CDCl_3$)m (7.63–7.20 Hz, 4H), s (4.50 Hz, 1H), s (4.25 Hz, 1H), q (3.85 Hz, 2H), s (3.10 Hz, 3H), s (2.81 Hz, 3H), t (1.31 Hz, 3H).

Example 82 Part B 2-(Bromoacetyl)-N,N-dimethylbenzamide

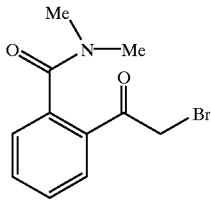

82B

To a solution of 82A (850 mg, 3.88 mmol) in THF (10 ml)/$H_2O$ (2 ml) was added N-bromosuccinimide (621 mg, 3.49 mmol). The mixture was stirred at RT for 15 min, then partitioned with AcOEt (80 ml) and $H_2O$ (15 ml). The organic layer was dried over $Na_2 SO_4$ and concentrated in vacuo to afford 82B (907 mg, 87%) as a yellow oil.

Example 82 Part C 2-(Azidoacetyl)-N,N-dimethylbenzamide

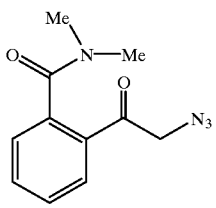

82C

To a solution of 82B (987 mg, 3.37 mmol) in acetone (7 ml)/ $H_2O$ (3 ml) was added $NaN_3$ (219 mg, 3.37 mmol) and the resulting mixture was stirred at 50° C. for 15 min. Added CH₂Cl₂ (40 ml) and H₂O (20 ml). The organic later was dried over Na₂SO₄ and concentrated in vacuo to afford 82C (777 mg, 92%) as a yellow oil.

Example 82 Part D

2-[2-[[3-Methoxy-4-(5-oxazolyl)phenyl]amino]-5-oxazolyl]-N,N-dimethylbenzamide

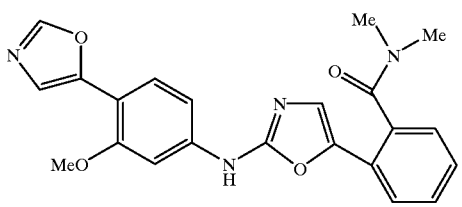

82D

To a mixture of 82C (100 mg, 0.43 mmol) and 4-(2-oxozol)-3-methoxy phenyl thioisocyanate (199 mg, 0.86 mmol) in CH₂Cl₂ (2 ml) was added PPh₃ (225 mg, 0.86 mmol) in one portion. Stirred at RT for overnight. The reaction solution was partitioned with 6 N HCl (12 ml) and CH₂C₂ (15 ml). The HCl layer was cooled at 0° C. and made basic by slow addition of 30% KOH solution. The aqueous layer was extracted with EtOAc (3×20 ml). The organic solution was washed with H₂O, sat. NaCl, dried over Na₂SO₄ and concentrated in vacuo. The residue was purified with chromatography on silica gel AcOEt to afford 82 (97 mg, 56%) as a yellow oil. ¹H NMR (DMSO) 10.62 (s, 1H), 8.37 (s, 1H), 7.66–7.27 (m, 8H), 7.06 (s, 1H), 3,94 (s, 3H), 3.30 (s, 3H), 2.66 (s, 3H)

EXAMPLE 83

2-[2-[[3-Methoxy-4-(5-oxazolyl)phenyl]amino]-5-oxazolyl]-N-methylbenzamide

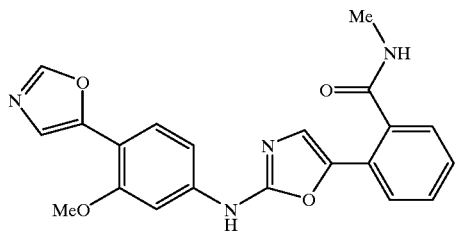

83

Example 83 Part A 2-(1-Ethoxyethenyl)benzoic acid phenylmethyl ester

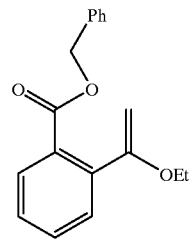

83A

To a solution of Benzyl 2-bromobenzoate (4.0 g, 13.8 mmol) in dioxane (70 ml) was added tributyl(1-ethoxyvinyl)tin (4.89 ml, 14.5 mmol) and dichlorobis (triphenylphosphine)palladium(II) (484 mg, 0.69 mmol). The mixture was stirred at 100° C. for 4 hr, diluted with EtOAc (150 ml), and filtered through a thin pad of celite®. The filtrate was concentrated under reduced pressure and purified by silica gel column chromatography to afford 83A (3.9 g, 99%) as light yellow oil which had a HPLC retention time of 4.26 min (Column: YMC S5 ODS 4.6×50 mm Ballistic; Solvent A=10% MeOH, 90% H₂O, 0.2% H₃PO₄; Solvent B=90% MeOH, 10% H₂O, 0.2% H₃PO₄)

Example 83 Part B

2-Bromoacetyl)benzoic acid phenylmethyl ester

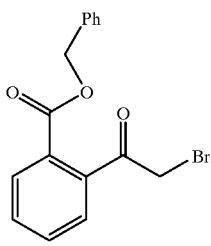

83B

To a solution of 83A (3.1 g, 10.95 mmol) in THF (36 ml) and water (8.0 ml) was added N-bromosuccinimide (2.04 g, 11.5 mmol). The reaction mixture was stirred at RT for 10 min, concentrated in vacuo, and partitioned with AcOEt (150 ml) and water (40 ml). The AcOEt layer was dried over sodium sulfate and concentrated in vacuo to afford 83B (2.89 g, 98%) as an oil which had a HPLC retention time of 3.89 min (Column: YMC S5 ODS 4.6×50 mm Ballistic; Solvent A=10% MeOH, 90% H₂O, 0.2% H₃PO₄; Solvent B=90% MeOH, 10% H₂O, 0.2% H₃PO₄).

Example 83 Part C 2-(Azidoacetyl)benzoic acid phenylmethyl ester

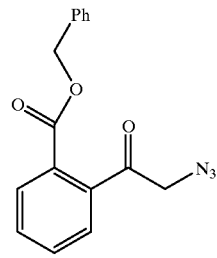

83C

To a solution of 83B (2.89 g, 8.68 mmol) in acetone (20 ml) and water (7 ml) was added sodium azide (592 mg, 9.11 mmol) in one portion. Resulting mixture was stirred at 50° C. for 15 min. The reaction mixture was concentrated under reduced pressure and the residue was redissolved in dichloromethane (125 ml) and washed with water (50 ml). The dichloromethane layer was concentrated under reduced pressure to afford 83C (2.48 g, 97%) as a yellow oil which had a HPLC retention time of 3.90 min (Column: YMC S5 ODS 4.6×50 mm Ballistic; Solvent A=10% MeOH, 90% $H_2O$, 0.2% $H_3PO_4$; Solvent B=90% MeOH, 10% $H_2O$, 0.2% $H_3PO_4$).

Example 83 Part D

2-[2-[[3-Methoxy-4-(5-oxazolyl)phenyl]amino]-5-oxazolyl]benzoic acid phenylmethyl ester

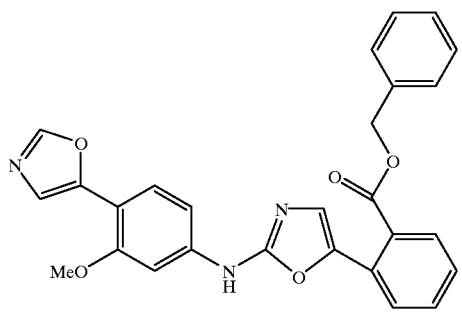

83D

To a mixture of 83C (2.48 g, 8.40 mmol) and 1E (1.72 g, 7.39 mmol) in dichloromethane (40 ml) was added triphenylphosphine (2.2 g, 8.40 mmol) in one portion and the reaction mixture was stirred at RT for 3.5 hours. The reaction mixture was partitioned between 6 N HCl (70 ml) and dichloromethane (60 ml). The HCl layer was cooled at 0° C. and basified by the slow addition of 30% KOH solution and extracted into EtOAc (4×50 ml). The EtOAc layer was washed with water, brine, dried over sodium sulfate and concentrated in vacuo to afford 83D (1.92 g crude) as foamy solid.

Example 83 Part E

2-[2-[[(1,1-Dimethylethoxy)carbonyl][3-methoxy-4-(5-oxazolyl)phenyl]amino]-5-oxazolyl]benzoic acid phenylmethyl ester

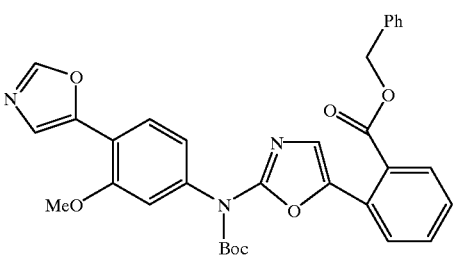

83E

To a mixture of 83D (1.92 g, 4.11 mmol), di-tert-butyldicarbonate (1.34 g, 6.16 mmol), 4-Dimethylaminopyridine (100 mg, 0.82 mmol) in DMSO (10 ml) was added triethylamine (1.72 ml, 12.3 mmol). The reaction mixture was stirred at 60° C. for 3.5 hours and partitioned between AcOEt (80 ml) and $H_2O$ (40 ml). The EtOAc layer was successively washed with 1 N HCl (50 ml), $H_2O$ (40 ml), Sat. $Na_2CO_3$ (50 ml), $H_2O$ (50 ml), dried over $Na_2SO4$, concentrated in vacuo and purified using silica gel column chromatography (20% AcOEt/hexane) to afford the title compound (1.21 g, 70%) as a foamy solid. $^1H$ NMR (CDCl$_3$): δ7.92 (t, 1H), 7.83 (d, 1H), 7.77 (d, 1H), 7.63–7.52 (m, 4H), 7.45 (t, 1H), 7.39–7.23 (m, 7H), 5.20 (s, 2H) 3.95 (s, 3H), 151 (s, 9H).

Example 83 Part F

2-[2-[[(1,1-Dimethylethoxy)carbonyl][3-methoxy-4-(5-oxazolyl)phenyl]amino]-5-oxazolyl]benzoic acid

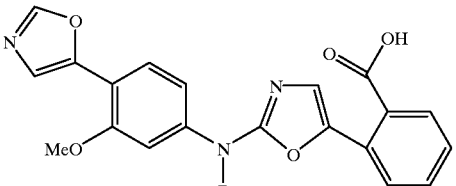

83F

To a suspension of Pd/C (600 mg) in MeOH (10 ml) was added 83E (847 mg, 1.49 mmol), followed by addition of ammonium formate (1.34 g, 223 mmol). The reaction mixture was stirred overnight at RT, diluted with AcOEt (150 ml) and filtered. The EtOAc layer was concentrated in vacuo to afford 83F (572 mg, 86%) as a yellow solid. $^1H$ NMR (DMSO): δ8.45 (s, 1H), 7.71 –7.56 (m, 7H), 7.15 (s, 1H), 6.98 (d, 1H), 3.94 (s, 3H), 1.43 (s, 9H).

Example 83 Part G

[3-Methoxy-4-(5-oxazolyl)phenyl][5-[2-[(methylamino)carbonyl]phenyl]-2-oxazolyl]carbamic acid 1,1-dimethylethyl ester

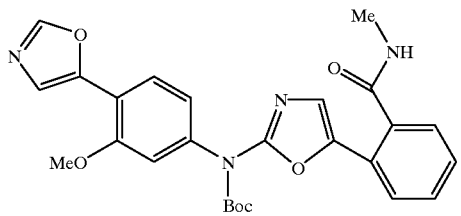

83G

To a mixture of 83F (50 mg, 0.105 mmol) methylamine (2M in THF, 65 µl, 1.3 mmol)1-hydroxyy-7-azabenzotriaole (18.5 mg, 0.136 mmol) and 1-[3-(dimethylamino) propyl]-3-ethylcarbodiimide hydrochloride (26 mg, 0.136 mmol) in THF (1 ml) was added N,N-diisopropylethylamine (55 µl, 0.315 mmol). The mixture was stirred at 50° C. for 18 hours diluted with dichloromethane (4 ml) and successively washed with 1N HCl (2 ml), 10% NaOH (2 ml)and brine. The dichloromethane layer was dried over sodium sulfate and concentrated in vacuo to afford 83G (51 mg, 97%) as a yellow solid. (LC/MS retention time=3.70 min.; $M^+$=491.30 Column: YMC S5 ODS 4.6×5.0 mm Ballistic. Solvent A=10% MeOH, 90% $H_2O$, 0.1% TFA; Solvent B=90% MeOH, 10% $H_2O$, 0.1% TFA).

Example 83 Part H

2-[2-[[3-Methoxy-4-(5-oxazolyl)phenyl]amino]-5-oxazolyl]-N-methylbenzamide

A solution of 83G (50 mg, 0.102 mmol) in trifluoroacetic acid (2 ml) was stirred at RT for 20 min. Excess TFA was removed in vacuo and the residue was dissolved with AcOEt (50 ml), washed with sat. aqueous sodium bicarbonate (20 ml), dried over sodium sulfate and concentrated in vacuo to afford 83 (31 mg, 79%) as an off white solid which had a HPLC retention time of 3.36 min (Column: YMC S5 ODS 4.6×50 mm Ballistic; Solvent A=10% MeOH, 90% $H_2O$, 0.2% $H_3PO_4$; Solvent B=90% MeOH, 10% $H_2O$, 0.2% $H_3PO_4$).

EXAMPLES 84 TO 87

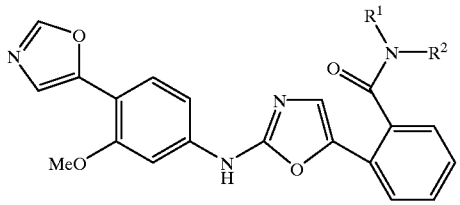

Compounds 84 to 87 were prepared from 83F by a route analogues to that used in example 83 replacing methyl amine with the required $R_1R_2NH$. The compounds of these examples have structures outlined in Table 3 below.

TABLE 3*

| Example | R | Name | HPLC time (min) | $M^+$ |
|---|---|---|---|---|
| 84 | NH₂-tetrahydrofuran-3-yl | (S)-2-[2-[[3-Methoxy-4-(5-oxazolyl)phenyl]amino]-5-oxazolyl]-N-(tetrahydro-3-furanyl)benzamide | 3.37 | 447.31 |
| 85 | NH-CH₂-tetrahydrofuran-3-yl | (S)-2-[2-[[3-Methoxy-4-(5-oxazolyl)phenyl]amino]-5-oxazolyl]-N-(tetrahydro-3-furanyl)benzamide | 3.49 | 461.32 |
| 86 | 4-methylpiperazinyl | 1-[[2-[2-[[3-Methoxy-4-(5-oxazolyl)phenyl]amino]-5-oxazolyl]phenyl]carbonyl]-4-methylpyrazine | 2.50 | 460.27 |
| 87 | NH-CH₂CH₂-morpholinyl | 2-[2-[[3-Methoxy-4-(5-oxazolyl)phenyl]amino]-5-oxazolyl]-N-[2-(4-morpholinyl)ethyl]benzamide | 2.53 | 490.25 |

*The HPLC conditions for the examples listed above is as follows: Column: YMC S5 ODS 4.6 × 5.0 mm Ballistic. Solvent A = 10% MeOH, 90% $H_2O$, 0.1% TFA; Solvent B = 90% MeOH, 10% $H_2O$, 0.1% TFA. Flow rate: 4 mL/min. Gradient: 4 min.

EXAMPLE 88

N-[3-Methoxy-4-(5-oxazolyl)phenyl]-N-methyl-5-phenyl-2-oxazolamine

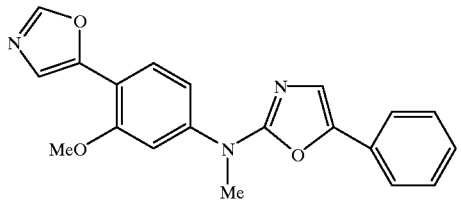

To a solution of 34 (0.2 g, 0.6 mmol) in 5 mL of anhydrous DMF was added sodium hydride (95%, 0.030 g, 1.2 mmol) and the contents stirred at RT for 15 min. Iodomethane (37 μL, 1.2 mmol) is added, the reaction mixture stirred at RT for 15 min and partitioned between ethyl acetate and water. The ethyl acetate layer was dried over sodium sulfate and concentrated to yield 0.210 g of the title compound as a solid. (LC/MS retention time=4.28 min.; $M^+$=348.21 Column: YMC S5 ODS 4.6×5.0 mm Ballistic. Solvent A=10% MeOH, 90% $H_2O$, 0.1% TFA; Solvent B=90% MeOH, 10% $H_2O$, 0.1% TFA).

EXAMPLE 89

4,5-Dihydro-N-[3-methoxy-4-(5-oxazolyl)phenyl]-5-phenyl-2-oxazolamine

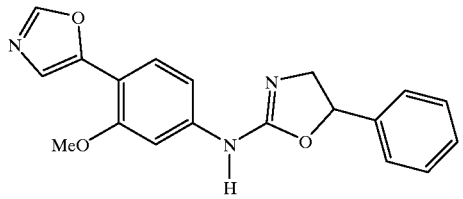

Example 89 Part A

N-(2-Hydroxy-2-phenylethyl)-N'-[3-methoxy-4-(5-oxazolyl)phenyl]thiourea

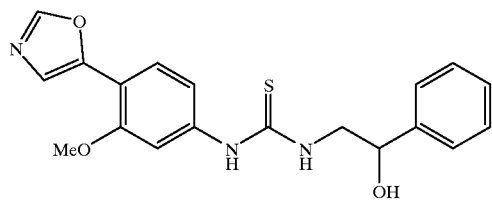

To a solution of 1E (0.1 g, 0.43 mmol) in 5 mL of dioxane was added (±) 2-amino-1-phenylethanol (0.059 g, 0.43 mmol) and the contents refluxed for 18 hours. The reaction mixture was concentrated under pressure and the solid that was obtained is crystallized from ether/ethyl acetate to yield 0.089 g of the title compound. $^1H$ NMR (DMSO-$d_6$) δ9.95 (s, 1H), 8.4 (s, 1H), 7.95(m,1H), 7.6 (m, 2H), 7.25–7.4 (m, 6H), 7.1 (d, 1H), 5.7 (s, 1H), 4.9 (m, 1H), 3.9 (brs, 4H), 3.4 (m, 1H).

Example 89 Part B 4,5-Dihydro-N-[3-methoxy-4-(5-oxazolyl)phenyl]-5-phenyl-2-oxazolamine To a solution of 89A (0.089 g, 0.24 mmol) in 3 mL of acetonitrile at 0° C. was added 2-chloro-3-ethylbenzoxazolium tetrafluoroborate (0.108 g, 0.39 mmol). The reaction mixture was stirred at 0° C. for 1 hour and triethylamine (0.107 mL, 0.768 mmol) was added. After stirring at RT for 5 hours the reaction mixture was concentrated under reduced pressure and partitioned between 3N HCl and ethyl acetate. The HCl layer was cooled to 0° C., made basic with 20% aqueous potassium hydroxide and extracted into ethyl acetate. The ethyl acetate layer was concentrated under reduced pressure and purified by silica gel column chromatography to yield 0.020 g of the title compound as a solid melting at 130–132° C. (LC/MS retention time=3.06 min.; $M^+$= 336.19 Column: YMC S5 ODS 4.6×5.0 mm Ballistic. Solvent A=10% MeOH, 90% $H_2O$, 0.1% TFA; Solvent B=90% MeOH, 10% $H_2O$, 0.1% TFA).

EXAMPLE 90

N-[3-Methoxy-4-(5-oxazolyl)phenyl]-5-(2-pyrrolidinyl)-2-oxazolamine

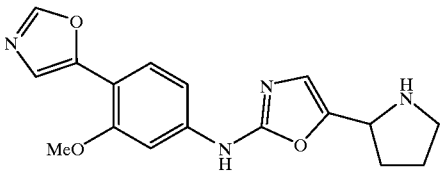

To a suspension of Pd/C (30 mg) in MeOH (2 ml) was added 64 (55 mg, 0.119 mmol) and Ammonium formate (150 mg, 2.39 mmol). The mixture was stirred at RT for 3 hr and then diluted with AcOEt (60 ml). The solution was filtered and concentrated in vacuo to give the title compound as an oil (28 mg, 74%). (LC/MS retention time=2.60 min.; $M^+$=327.22 Column: YMC S5 ODS 4.6×5.0 mm Ballistic. Solvent A=10% MeOH, 90% $H_2O$, 0.1% TFA; Solvent B=90% MeOH, 10% $H_2O$, 0.1% TFA).

EXAMPLE 91

2-[2-[[3-Methoxy-4-(5oxazolyl)phenyl]amino]-5-oxazolyl]-1-pyrrolidinecarboxylic acid methyl ester

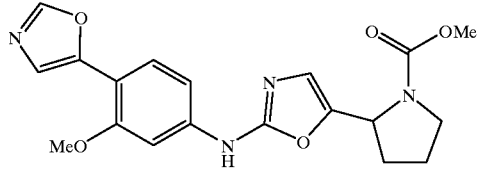

To a solution of 90 (86 mg 0.264 mmol) in THF (3 ml) and H₂O (3 ml) was added K₂CO₃ (47 mg, 0.342 mmol) followed by addition of methylchloroformate (265 μl, 0.343 mmol). The mixture was stirred at RT overnight and partitioned between AcOEt (50 ml) and H₂O (30 ml). The AcOEt layer was dried over Na₂SO₄ and concentrated in vacuo. The residue that was obtained was triturated with ether to afford 91 (13 mg) as an off-white solid. (LC/MS retention time= 3.46 min.; M⁺=385.22 Column: YMC S5 ODS 4.6×5.0 mm Ballistic. Solvent A=10% MeOH, 90% H₂O, 0.1% TFA; Solvent B=90% MeOH, 10% H₂O, 0.1% TFA).

EXAMPLES 92 TO 96

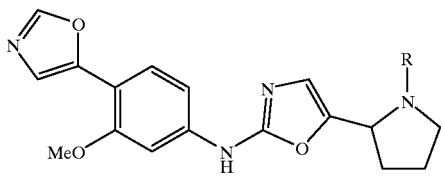

Compounds 92 to 96 were prepared from 90 by a route analogues to that used in example 91 replacing methylchloroformate with the required reagents. The compounds of these examples have structures outlined in Table 4 below.

TABLE 4*

| Example | R | Name | HPLC time (min) | M⁺ |
|---|---|---|---|---|
| 92 | (CH₂-C(=O)-CH₂-OMe) | 2-[2-[[3-Methoxy-4-(5-oxazolyl)phenyl]amino]-5-oxazolyl]-N-methoxymethylcarbonyl pyrrolidine | 3.12 | 399.22 |
| 93 | (CH₂-C(=O)-CH₂-morpholino) | 2-[2-[[3-Methyoxy-4-(5-5-oxazolyl]-N-[4-morpholinomethylcarbonyl] pyrrolidine | 2.86 | 454.36 |
| 94 | (C(=O)-OEt) | 2-[2-[[3-Methoxy-4-(5-oxazolyl)phenyl]amino]-5-oxazolyl]-1-pyrrolidinecarboxylic acid ethyl ester | 3.01 | 399.22 |
| 95 | (C(=O)-O-CH₂CH₂-SO₂CH₃) | 2-[2-[[3-Methoxy-4-(5-oxazolyl)phenyl]amino]-5-oxazolyl]-1-pyrrolidinecarboxylic acid 2-(methylsulfonyl)ethyl ester | 3.23 | 477.26 |
| 96 | (C(=O)-O-3-tetrahydrofuranyl) | 2-[2-[[3-Methoxy-4-(5-oxazolyl)phenyl]amino]-5-oxazolyl]-1-pyrrolidinecarboxylic acid 3-tetrahydrofuranyl ester | 3.53 | 441.32 |

*The HPLC conditions for the examples listed above is as follows: Column: YMC S5 ODS 4.6 × 5.0 mm Ballistic. Solvent A = 10% MeOH, 90% H₂O, 0.1% TFA; Solvent B = 90% MeOH, 10% H₂O, 0.1% TFA. Flow rate: 4 mL/min. Gradient: 4 min.

EXAMPLE 97

N-[3-Hydroxy-4-(5-oxazolyl)phenyl]-5-phenyl-2-oxazolamine

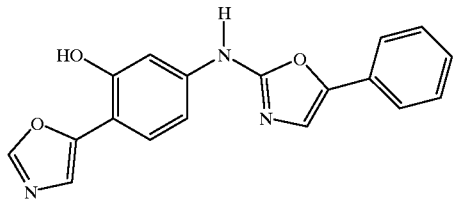

97

Example 97 Part A

N-[[(1,1-Dimethylethoxy)carbonyl]-N-[3-methoxy-4-(5-oxazolyl)phenyl]-5-phenyl-2-oxazolamine

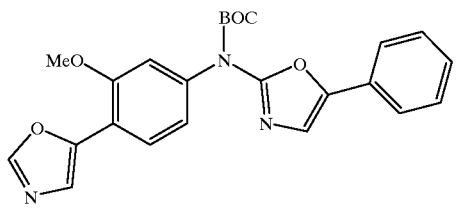

97A

A mixture of 34 (300 mg, 0.90 mmol), Dimethylaminopyridine (22 mg, 0.18 mmol), triethylamine (0.38 mL, 2.70 mmol), and di-tert-butyl dicarbonate (295 mg, 1.35 mmol) in 5 mL of dimethylsulfoxide was heated at 60° C. for 3 h. The reaction mixture was cooled to room temperature and partitioned between ethyl acetate and water. The organic layer was washed with 5% aqueous HCl, saturated aqueous sodium bicarbonate, brine, and dried over anhydrous sodium sulfate. Concentration under reduced pressure afforded 0.372 g (95%) of 97A as a tan solid with a retention time of 4.34 min.(Column: YMC S5 ODS 4.6×50 mm Ballistic; Solvent A=10% MeOH, 90% $H_2O$, 0.2% $H_3PO_4$; Solvent B=90% MeOH, 10% $H_2O$, 0.2% $H_3PO_4$) and a LC/MS of 434.21 ($M^{+1}$).

Example 97 Part B

N-[3-Hydroxy-4-(5-oxazolyl)phenyl]-5-phenyl-2-oxazolamine

To 97A (184 mg, 0.424 mmol) in 30 mL of dry dichloromethane at 0° C. was added 3.4 mL (3.39 mmol) of a 1.0 M solution of boron tribromide in dichloromethane. The ice bath was removed, and the reaction mixture was stirred for approximately 70 h at room temperature. The excess boron tribromide was quenched with water, and the resulting mixture was extracted with a mixture of dichloromethane and acetone. The organic layer was washed with water, brine, and dried over anhydrous sodium sulfate. Concentration under reduced pressure afforded a crude product which was washed with ether to give 0.125 g (93%) of the title compound as a pale yellow solid. The product had a HPLC retention time of 3.85 min (Column: YMC S5 ODS 4.6×50 mm Ballistic; Solvent A=10% MeOH, 90% $H_2O$, 0.2% $H_3PO_4$; Solvent B=90% MeOH, 10% $H_2O$, 0.2% $H_3PO_4$) and a LC/MS $M^{+1}$=320.12.

EXAMPLE 98

N-[3-[(1,1-Dimethylethoxy)carbonylmethoxy](-4-(5-oxazolyl)phenyl]-5-phenyl-2-oxazolamine

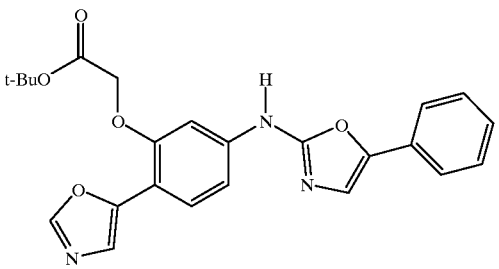

98

A 2 dram vial containing 97 (30 mg, 0.094 mmol), tert-butyl bromoacetate (15.2 μL, 0.094 mmol), and potassium carbonate (39 mg, 0.282 mmol) in 1.5 mL of anhydrous DMF was shaken at 216 rpm at approximately 60° C. in an Innova 2000 Platform Shaker equipped with a standard heat block for 48 h. The reaction mixture was diluted with ethyl acetate, washed with water, brine, and dried over anhydrous sodium sulfate. Concentration under reduced pressure afforded 62 mg (91%) of the title compound as a light brown solid The product had a HPLC retention time of 4.52 min. (Column: YMC S5 ODS 4.6×50 mm Ballistic; Solvent A=10% MeOH, 90% $H_2O$, 0.2% $H_3PO_4$; Solvent B=90% MeOH, 10% $H_2O$, 0.2% $H_3PO_4$) and a LC/MS $M^{+1}$=434.26.

EXAMPLE 99

N-[3-Methoxycarbonylmethoxy-4-(5-oxazolyl)phenyl]-5-phenyl-2-oxazolamine

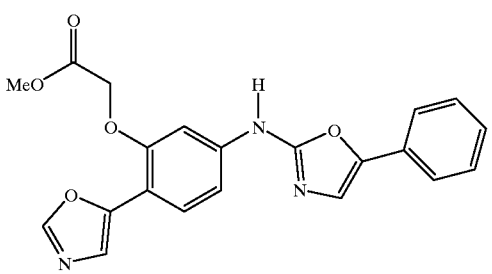

99

A mixture of 97 (33 mg, 0.103 mmol), methyl bromoacetate (9.8 μL, 0.103 mmol), and potassium carbonate (43 mg, 0.309 mmol) in 1.5 mL of andhydrous N,N-dimethylformamide was subjected to the procedure used in the preparation of 98 (reaction time=16 h) to give a brown solid. Subsequent washing with ether afforded 16.6 mg of the title compound as a light brown solid which had a HPLC retention time of 4.19 min.; (Column: YMC S5 ODS 4.6×50 mm Ballistic; Solvent A=10% MeOH, 90% $H_2O$, 0.2% $H_3PO_4$; Solvent B=90% MeOH, 10% $H_2O$, 0.2% $H_3PO_4$) and a LC/MS $M^{+1}$=392.17.

EXAMPLE 100

N-[3-Ethoxy-4-(5-oxazolyl)phenyl]-5-phenyl-2-oxazolamine

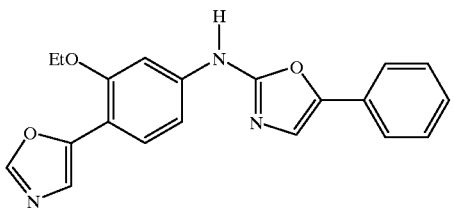

100

A mixture of 97 (32 mg, 0.100 mmol), iodoethane (8.2 µL, 0.100 mmol), and potassium carbonate (41 mg, 0.300 mmol) in 1.5 mL of anhydrous N,N-dimethylformamide was subjected to the procedure used in the preparation of 98 (reaction time=16 h). The mixture was purified by preparative HPLC to provide 6.0 mg of BMS-344787 as a light tan solid which had a HPLC retention time of 4.39 min.; (Column: YMC S5 ODS 4.6×50 mm Ballistic; Solvent A=10% MeOH, 90% $H_2O$, 0.2% $H_3PO_4$; Solvent B=90% MeOH, 10% $H_2O$, 0.2% $H_3PO_4$) and a LC/MS $M^{+1}$=348.19.

EXAMPLE 101

N-[3-(Cyanomethoxy)-4-(5-oxazolyl)phenyl]-5-phenyl-2-oxazolamine

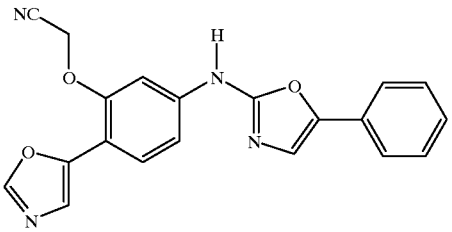

101

A mixture of 97 (30 mg, 0.094 mmol), bromoacetonitrile (6.5 µL, 0.094 mmol), and potassium carbonate (39 mg, 0.282 mmol) in 1.5 mL of anhydrous N,N-dimethylformamide was subjected to the procedure used in the preparation of 98 (reaction time=16 h). The mixture was purified by preparative HPLC to provide 9.0 mg of the title compound as a tan solid which had a HPLC retention time of 3.96 min.; (Column: YMC S5 ODS 4.6×50 mm Ballistic; Solvent A=10% MeOH, 90% $H_2O$, 0.2% $H_3PO_4$; Solvent B=90% MeOH, 10% $H_2O$, 0.2% $H_3PO_4$) with a LC/MS $M^{+1}$=359.15.

EXAMPLE 102

5-(2-Bromophenyl)N-[3-methoxycarbonylmethoxy-4-(5-oxazolyl)phenyl]-2-oxazolamine

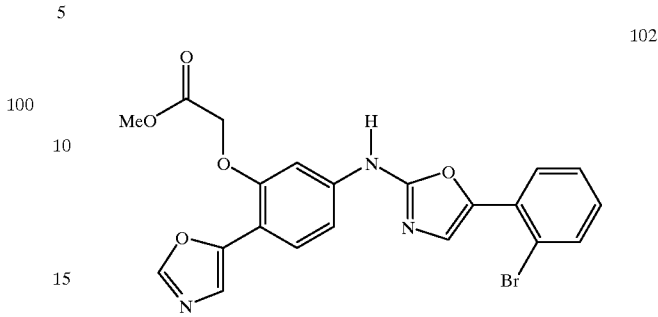

102

Example 102 Part A 5-(2-Bromophenyl)-N-[3-hydroxy-4-(5-oxazolyl)phenyl]-2-oxazolamine

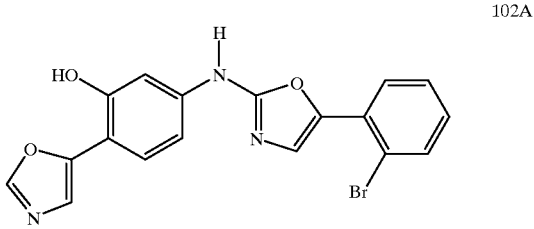

102A

To 51 (12 mg, 0.023 mmol) in 2 mL of dry dichloromethane at room temperature was added 0.23 mL (0.187 mmol) of a 1.0 M solution of boron tribromide in dichloromethane. The reaction mixture was stirred for approximately 40 h, and the excess boron tribromide was quenched with water. The organic layer was collected and washed with water, brine, and dried over anhydrous sodium sulfate. Concentration under reduced pressure afforded 8.7 mg (93%) of the title compound as a white solid. The product had a HPLC retention time of 4.24; (Column: YMC S5 ODS 4.6×a50 mm Ballistic; Solvent A=10% MeOH, 90% $H_2O$, 0.2% $H_3PO_4$; Solvent B=90% MeOH, 10% $H_2O$, 0.2% $H_3PO_4$) and a LC/MS $M^{+1}$=398.03.

Example 102 Part B 5-(2-Bromophenyl)-N-[3-methoxycarbonylmethoxy-4-(5-oxazolyl)phenyl]-2-oxazolamine A mixture of 102A (8.7 mg, 0.022 mmol), methyl bromoacetate (4.3 µL, 0.029 mmol), and potassium carbonate (9 mg, 0.065 mmol) in 1.0 mL of andhydrous N,N-dimethylformamide was subjected to the procedure used in the preparation of 98 (reaction time=16 h). The mixture was purified by preparative HPLC to provide 1.0 mg of the title compound as a white solid, which had a HPLC retention time of 4.45 min.; (Column: YMC S5 ODS 4.6×50 mm Ballistic; Solvent A=10% MeOH, 90% $H_2O$, 0.2% $H_3PO_4$; Solvent B=90% MeOH, 10% $H_2O$, 0.2% $H_3PO_4$) and a LC/MS $M^{+1}$=470.16 and 472.16).

The following HPLC Conditions are reported for Examples 103 to 235.

Solvent A=10% Methanol—90% water13 0.1% TFA

Solvent B=90% Methanol—10% water—0.1% TFA
Column=Shimadzu S5 C18 4.6×50 mm Ballistic
Condition A: Initial % B=40%, Final % B=100%, flow=4 ml/min gradient=4 min
Condition B: Initial % B=50%, Final % B=100%, flow=4 ml/min gradient=4 min
Condition C: Initial % B=60%, Final % B=100%, flow=4 ml/min gradient=4 min
Condition D: Initial % B=0%, Final % B=100%, flow=4 ml/min gradient=4 min
Condition E: Initial % B=90%, Final % B=100%, flow=4 ml/min gradient=4 min
Condition F: Initial % B=70%, Final % B=100%, flow=4 ml/min gradient=4 min
Condition G: Initial % B=80%, Final % B=100%, flow=4 ml/min gradient=4 min
Condition H: Initial % B=0%, Final % B=100%, flow=4 ml/min gradient=8 min
Condition J: Initial % B=30%, Final % B=100%, flow=4 ml/min gradient=4 min
Condition K: Initial % B=20%, Final % B=100%, flow=4 ml/min gradient=4 min

EXAMPLE 103

4-Chloro-N-[3-methoxy-4-(5-oxazolyl)phenyl]-6-phenyl-1,3,5-triazin-2-amine (A1)

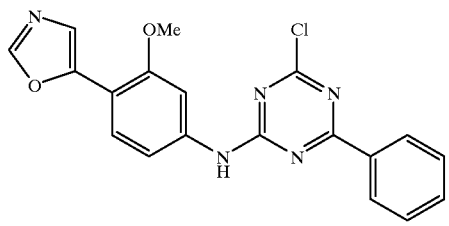

103

Example 103 Part A 2,4-Dichloro-6-phenyltriazine

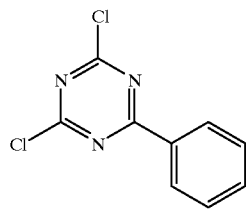

103A

Cyanuric chloride (18.5 g, 0.1 mol) was dissolved in 200 mL of toluene and cooled to 0° C. in an ice-salt bath. Phenyl magnesium bromide 3M solution in ether (33 mL, 0.1 mol) was added dropwise. The ice bath was removed and the reaction mixture was stirred for 1 h at room temperature. The solvent was evaporated and the residue extracted three times with 100 mL of hexane. The solvent was evaporated to approximately one-third to one-quarter of the initial volume and the solid collected. The product was recrystallized from hexane to yield 13.6 g (60%) of 103A as yellow crystals mp. 120–122° C.

Example 103 Part B

4-Chloro-N-[3-methoxy-4-(5-oxazolyl)phenyl]-6-phenyl-1,3,5-triazin-2-amine 2,4-Dichloro-6-phenyltriazine (5.0 g, 22.2 mmol) was dissolved in 50 mL of anhydrous THF and cooled in an ice water bath. 5-(4-Amino-2-methoxyphenyl)oxazole (4.43 g, 23.3 mmol) was dissolved in 50 mL of anhydrous TNF, and added dropwise to the triazine. The reaction mixture was stirred at room temperature for 4 h, and filtered. The solid was washed with 150 mL of water, 50 mL of ethanol, and 100 mL of ether, and dried to yield 8.4 g (99%) of 103. LCMS (Ret Time=4.61 min, BPLC condition B) M+H$^+$=380.18 (100%).

EXAMPLE 104

N-[3-Methoxy-4-(5-oxazolyl)phenyl]-N'-methyl-6-phenyl-1,3,5-triazine-2,4-diamine

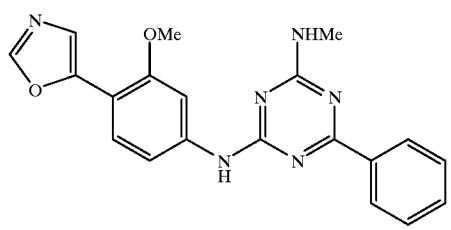

104

4-Chloro-N-[3-methoxy-4-(5-oxazolyl)phenyl]-6-phenyl-1,3,5-triazin-2-amine, 103, (27 mg, 0.07 mmol) was suspended in 2M methylamine in THF (1 mL, 2 mmol) was added and the reaction mixture heated in a sealed tube at 80° C. overnight. The product was filtered and purified by flash column chromatography (2% methanol in methylene chloride) to yield 22 mg (83%) of the title compound LCMS (Ret Time=3.15 min, HPLC condition B) M+H$^+$=375.23 (100%).

EXAMPLE 105

N-[3-Methoxy-4-(5-oxazolyl)phenyl]-N'-methyl-6-(2-methylphenyl)-1,3,5-triazine-2,4-diamine

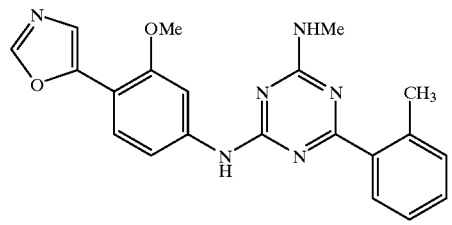

Example 105 Part A 2,4-Dichloro-6-(2-methylphenyl)triazine

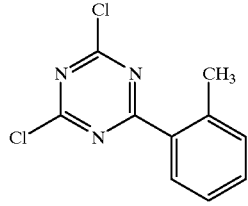

105A

Cyanuric chloride (4.61 g, 25 mmol) was dissolved in 50 mL of toluene and cooled to 0° C. in an ice-salt bath. 2-Methylphenyl magnesium bromide 2M solution in ether (12.5 mL, 25 mmol) was added dropwise. The ice bath was removed and the reaction mixture was stirred for 1 h at room temperature. The solvent was evaporated and the residue extracted three times with 50 mL of hexane. The solvent was evaporated to approximately one-third to one-quarter of the initial volume and the solid collected. The product was recrystallized from hexane to yield 105A, 2.0 g (34%) of light yellow solid.

Example 105 Part B

N-[3-Methoxy-4-(5-oxazolyl)phenyl]-N'-methyl-6-(4-methylphenyl)-1,3,5-triazine-2,4-diamine 2,4-Dichloro-6-(2-methylphenyl)triazine, 105A (232 mg, 1 mmol) was dissolved in anhydrous THF (2 mL) and cooled in an ice bath. 5-(4-Amino-2-methoxyphenyl)oxazole (190 mg, 1 mmol) was added and the reaction mixture stirred at room temperature overnight. The crude product was filtered and dried to yield 130 mg of 4-Chloro-N-[3-methoxy-4-(5-oxazolyl)phenyl]-6-(2-methylphenyl)-1,3,5-triazin-2-amine.

The product was suspended in 5 mL of 2M methylamine in THF and heated in a sealed tube at 80° C. overnight. The solvent was evaporated and the crude product purified by reverse phase HPLC to yield 6 mg (5%) of 105. LCMS (Ret Time=2.01 min, HPLC condition B) M+H$^+$=389.27 (100%).

EXAMPLE 106

4-Chloro-N-[3-methoxy-4-(5-oxazolyl)phenyl]-6-(4-methylphenyl)-1,3,5-triazin-2-amine

106

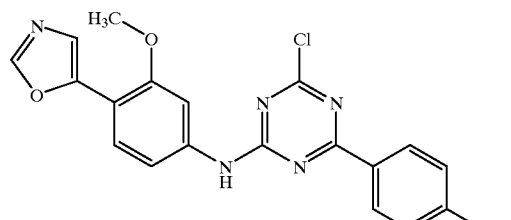

Example 106 Part A 2,4-Dichloro-6-(4-methylphenyl)triazine

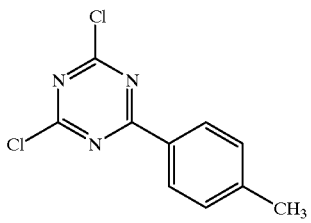

106A

Cyanuric chloride (4.61 g, 25 mmol) was dissolved in 50 mL of toluene and cooled to 0° C. in an ice-salt bath. 4-Methylphenyl magnesium bromide 2M solution in ether (12.5 mL, 25 mmol) was added dropwise. The ice bath was removed and the reaction mixture was stirred for 1 h at room temperature. The solvent was evaporated and the residue extracted three times with 50 mL of hexane. The solvent was evaporated to approximately one-third to one-quarter of the initial volume and the solid collected. The product was recrystallized from hexane to yield 1.2 g (21%) of light yellow solid.

Example 106 Part B

4-Chloro-N-[3-methoxy-4-(5-oxazolyl)phenyl]-6-(4-methylphenyl)-1,3,5-triazin-2-amine 2,4-Dichloro-6-(4-methylphenyl)triazine (232 mg, 1 mmol) was dissolved in anhydrous THF (2 mL) and cooled in an ice bath. 5-(4-Amino-2-methoxyphenyl)oxazole (190 mg, 1 mmol) was added and the reaction mixture stirred at room temperature overnight. The crude product was filtered and dried to yield 80 mg of 106. LCMS (Ret Time=4.63 min, BPLC condition A) M+H$^+$=394.14 (100%).

EXAMPLE 107

N-[3-Methoxy-4-(5-oxazolyl)phenyl]-N'-methyl-6-(4-methylphenyl)-1,3,5-triazine-2,4-diamine

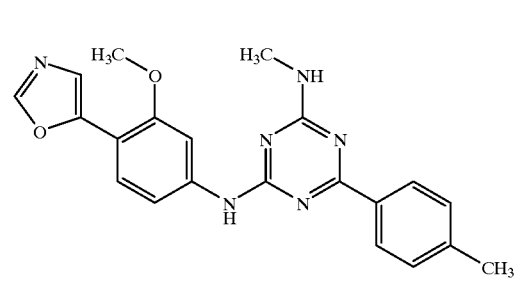

107

Example 106 (80 mg, 0.20 mmol) was suspended in 5 mL of 2M methylamine in THF and heated in a sealed tube at 80° C. for 3 h. The solvent was evaporated and the crude product purified by reverse phase HPLC to yield 12 mg (15%) of the title compound. LCMS (Ret Time=2.01 min, HPLC condition B) M+H$^+$=389.27 (100%).

EXAMPLES 108 TO 204

The compounds in table 5 below were prepared in a manner similar to that described for N-3-Methoxy-4-(5- oxazolyl)phenyl]-N'-methyl-6-phenyl-1,3,5-triazine-2,4-diamine, Example 104, from the intermediate 4-Chloro-N-[3-methoxy-4-(5-oxazolyl)phenyl]-6-phenyl-1,3,5-triazin-2-amine, Example 103 or a similar intermediate useful for this invention. The chlorotriazine intermediate was generally heated for 4–24 h in a solvent such as dimethoxyethane or THF in the presence of 5 to 10 equivalents of a desired amine. The product was generally purified by reverse phase HPLC to yield the products in table 5 below. The above method does not constitute a limitation on this invention.

TABLE 5

| EX. No | R | CompoundName | HPLC time/ Conditions | M + H$^+$ |
|---|---|---|---|---|
| 108 | —NHCH$_2$CH$_2$Ph | N-[3-Methoxy-4-(5-oxazolyl)phenyl]-6-phenyl-N-(2-phenylethyl)-1,3,5-triazine-2,4-diamine | 3.96/B | 465.35 |
| 109 | —OCH$_3$ | 4-Methoxy-N-[3-methoxy-4-(5-oxazolyl)phenyl]-6-phenyl-1,3,5-triazin-2-amine | 3.87/B | 376.23 |
| 110 | 4-Ph-piperazin1-yl | N-[3-Methoxy-4-(5-oxazolyl)phenyl]-4-(4-phenyl-1-piperazinyl)-6-phenyl-1,3,5-triazin-2-amine | 4.71/C | 506.28 |
| 111 | —NHCH$_2$CH$_2$CO$_2$C(CH$_3$)$_3$ | 3-[[4-[[3-Methoxy-4-(5 oxazolyl)phenyl]amino]-6-phenyl-1,3,5-triazin-2-yl)amino]propanoic acid 1,1-dimethylethyl ester | 4.00/B | 489.28 |
| 112 | —NHCH$_2$CO$_2$C$_2$H$_5$ | N-[4-[[3-Methoxy-4-(5-oxazolyl)phenyl]amino]-6-phenyl-1,3,5-triazin-2-yl]glycine ethyl ester | 3.34/B | 447.29 |
| 113 | morpholin-4-yl | N-[3-Methoxy-4-(5-oxazolyl)phenyl]-4-(4-morpholinyl)-6-phenyl-1,3,5-triazin-2-amine | 4.03/B | 431.22 |
| 114 | —NHCH$_2$Ph | N-[3-Methoxy-4-(5-oxazolyl)phenyl]-6-phenyl-N'-(phenylmethyl)-1,3,5-triazine-2,4-diamine | 4.00B | 451.29 |
| 115 | —NHCH$_2$CH$_2$OH | 2-[[4-[[3-Methoxy-4-(5-oxazolyl)phenyl]amino]-6-phenyl-1,3,5-triazin-2-yl]amino]ethanol | 3.98/D | 405.24 |
| 116 | —NH(CH$_2$)$_3$CO$_2$CH$_3$ | 4-[[4-[[3-Methoxy-4-(5-oxazolyl)phenyl]amino]-6-phenyl-1,3,5-triazin-2-yl]amino]butanoic acid methyl ester | 3.30/B | 461.33 |
| 117 | —NH(CH$_2$)$_3$OH | 3-[[4-[[3-Methoxy-4-(5-oxazolyl)phenyl]amino]-6-phenyl-1,3,5-triazin-2-yl]amino]-1-propanol | 2.57/B | 419.28 |
| 118 | 4-Me-piperazin-1-yl | N-[3-Methoxy-4-(5-oxazolyl)phenyl]-4-(4-methyl-1-piperazinyl)-6-phenyl-1,3,5-triazin-2-amine | 3.67/D | 444.33 |
| 119 | —NH(CH$_2$)$_2$CO$_2$H | 3-[[4-[[3-Methoxy-4-(5-oxazolyl)phenyl]amino]-6-phenyl-1,3,5-triazin-2-yl]amino]propanoic acid | 2.77/D | 433.27 |
| 120 | —NHCH$_2$ pyridin-3-yl | N-[3-Methoxy-4-(5-oxazolyl)phenyl]-6-phenyl-N'-(3-pyridinylmethyl)-1,3,5-triazine-2,4-diamine | 1.94/B | 452.23 |

TABLE 5-continued

| EX. No | R | Compound Name | HPLC time/ Conditions | M + H⁺ |
|---|---|---|---|---|
| 121 | —NHCH$_2$(5-methylfuran-2-yl) | N-[3-Methoxy-4-(5-oxazolyl)phenyl]-N'-[(5-methyl-2-furanyl)methyl]-6-phenyl-1,3,5-triazine-2,4-diamine | 3.97/B | 455.38 |
| 122 | —NHCH(CH$_2$OH)(CH$_2$Ph) | (S)-□-[[4-[[3-Methoxy-4-(5-oxazolyl)phenyl]amino]-6-phenyl-1,3,5-triazin-2-yl]amino]benzenepropanol | 3.60/B | 495.34 |
| 123 | —NH(CH$_2$)$_2$pyridin-3-yl | N-[3-Methoxy-4-(5-oxazolyl)phenyl]-6-phenyl-N'-[2-(3-pyridinyl)ethyl]-1,3,5-triazine-2,4-diamine | 1.89/B | 466.33 |
| 124 | —NHCH$_2$tetrahydrofuran-2-yl | N-[3-Methoxy-4-(5-oxazolyl)phenyl]-6-phenyl-N'-[(tetrahydro-2-furanyl)methyl]-1,3,5-triazine-2,4-diamine | 3.39/B | 445.34 |
| 125 | —NH(CH$_2$)$_3$imidazol-1-yl | N-[3-(1H-Imidazol-1-yl)propyl]-N'-[3-methoxy-4-(5-oxazolyl)phenyl]-6-phenyl-1,3,5-triazine-2,4-diamine | 1.63/B | 469.39 |
| 126 | —NH(1-ethoxycarbonyl-piperazin-4-yl) | 4-[[4-[[3-Methoxy-4-(5 oxazolyl)phenyl]amino]-6-phenyl-1,3,5-triazin-2-yl]amino]-1-piperidinecarboxylic acid ethyl ester | 3.92/B | 516.34 |
| 127 | —NH(CH$_2$)$_6$N(CH$_3$)$_2$ | N-[6-(Dimethylamino)hexyl]-N'-[3-methoxy-4-(5-oxazolyl)phenyl]-6-phenyl-1,3,5-triazine-2,4-diamine | 1.97/B | 488.65 |
| 128 | —NH(CH$_2$)$_2$pyridin-4-yl | N-[3-Methoxy-4-(5-oxazolyl)phenyl]-6-phenyl-N'-[2-(4-pyridinyl)ethyl]-1,3,5-triazine-2,4-diamine | 1.81/B | 466.19 |
| 129 | —NH(CH$_2$)$_4$OH | 4-[[4-[[3-Methoxy-4-(5-oxazolyl)phenyl]amino]-6-phenyl-1,3,5-triazin-2-yl]amino]-1-butanol | 2.69/B | 433.39 |
| 130 | —NHCH$_2$pyridin-2-yl | N-[3-Methoxy-4-(5-oxazolyl)phenyl]-6-phenyl-N'-(2-pyridinylmethyl)-1,3,5-triazine-2,4-diamine | 2.11/B | 452.28 |
| 131 | —NHCH$_2$(1-ethylpyrrolidin-2-yl) | N-[(1-Ethyl-2-pyrrolidinyl)methyl]-N'-[3-methoxy-4-(5-oxazolyl)phenyl]-6-phenyl-1,3,5-triazine-2,4-diamine | 1.77/B | 472.35 |
| 132 | —NH(CH$_2$)$_2$NHCOCH$_3$ | N-[2-[[4-[[3-Methoxy-4-(5-oxazolyl)phenyl]amino]-6-phenyl-1,3,5-triazin-2-yl]amino]ethyl]acetamide | 2.56/B | 446.26 |
| 133 | —NH(CH$_2$)$_3$O(CH$_2$)$_3$CH$_3$ | N-(3-Butoxypropyl)-N'-[3-methoxy-4-(5-oxazolyl)phenyl]-6-phenyl-1,3,5-triazine-2,4-diamine | 4.21/B | 475.31 |

TABLE 5-continued

| EX. No | R | CompoundName | HPLC time/ Conditions | M + H+ |
|---|---|---|---|---|
| 134 | —NH(CH$_2$)$_3$morpholin-4-yl | N-[3-Methoxy-4-(5-oxazolyl)phenyl]-N'-[3-(4-morpholinyl)propyl]-6-phenyl-1,3,5-triazine-2,4-diamine | 1.56/B | 488.30 |
| 135 | —NHCH(CH$_2$OH)(CH$_2$Ph$_{4\text{-OH}}$) | (S)-4-Hydroxy-□-[[4-[[3-methoxy-4-(5-oxazolyl)phenyl]amino]-6-phenyl-1,3,5-triazin-2-yl]amino]benzenepropanol | 2.68/B | 511.24 |
| 136 | —NH(CH$_2$)$_2$CH(CH$_3$)$_2$ | N-[3-Methoxy-4-(5-oxazolyl)phenyl]-N'-(3-methylbutyl)-6-phenyl-1,3,5-triazine-2,4-diamine | 4.18/B | 431.34 |
| 137 | —NH(CH$_2$)$_2$pyrrolidin-1-yl | N-[3-Methoxy-4-(5-oxazolyl)phenyl]-6-phenyl-N'-[2-(1-pyrrolidinyl)ethyl]-1,3,5-triazine-2,4-diamine | 1.66/B | 458.26 |
| 138 | —NH$_2$ | N-[3-Methoxy-4-(5-oxazolyl)phenyl]-6-phenyl-1,3,5-triazine-2,4-diamine | 2.46/A | 361.29 |
| 139 | —N(CH$_3$)(OCH$_3$) | N-Methoxy-N'-[3-methoxy-4-(5-oxazolyl)phenyl]-N-methyl-6-phenyl-1,3,5-triazine-2,4-diamine | 4.39/A | 405.30 |
| 140 | —NH(OCH$_3$) | N-Methoxy-N'-[3-methoxy-4-(5-oxazolyl)phenyl]-6-phenyl-1,3,5-triazine-2,4-diamine | 3.58/A | 391.29 |
| 141 | —NHCH$_2$cyclopropyl | N-(Cyclopropylmethyl)-N'-[3-methoxy-4-(5-oxazolyl)phenyl]-6-phenyl-1,3,5-triazine-2,4-diamine | 3.73/B | 415.23 |
| 142 | —NH(CH$_2$)$_3$CH$_3$ | N-Butyl-N'-[3-methoxy-4-(5-oxazolyl)phenyl]-6-phenyl-1,3,5-triazine-2,4-diamine | 4.01/B | 417.26 |
| 143 | —NH(CH$_2$)$_3$O(CH$_2$)$_2$CH$_3$ | N-[3-Methoxy-4-(5-oxazolyl)phenyl]-6-phenyl-N'-(3-propoxypropyl)-1,3,5-triazine-2,4-diamine | 4.04 | 461.31 |
| 144 | —NH(CH$_2$)$_3$OCH$_3$ | N-[3-Methoxy-4-(5-oxazolyl)phenyl]-6-phenyl-N'-(3-propoxypropyl)-1,3,5-triazine-2,4-diamine | 3.32/B | 433.27 |
| 145 | —NHCH2(cyclohexane-1-yl-1-ol) | 1-[[[4-[[3-Methoxy-4-(5-oxazolyl)phenyl]amino]-6-phenyl-1,3,5-triazin-2-yl]amino]methyl]cyclohexanol | 3.88/B | 473.32 |
| 146 | —NH(CH$_2$)$_3$N(C$_2$H$_5$)$_2$ | N-[3-(Diethylamino)propyl]-N'-[3-methoxy-4-(5-oxazolyl)phenyl]-6-phenyl-1,3,5-triazine-2,4-diamine | 1.86/B | 474.36 |
| 147 | —NHCH$_2$CH(CH$_3$)$_2$ | N-[3-Methoxy-4-(5-oxazolyl)phenyl]-N'-(2-methylpropyl)-6-phenyl-1,3,5-triazine-2,4-diamine | 3.98/B | 417.15 |

TABLE 5-continued

| EX. No | R | CompoundName | HPLC time/ Conditions | M + H+ |
|---|---|---|---|---|
| 148 | —NH(CH$_2$)$_2$imidazol-4-yl | N-[2-(1H-Imidazol-4-yl)ethyl]-N'-[3-methoxy-4-(5-oxazolyl)phenyl]-6-phenyl-1,3,5-triazine-2,4-diamine | 1.72/B | 455.30 |
| 149 | —NHCH$_2$CH(OH)(CH$_2$OH) | 3-[[4-[[3-Methoxy-4-(5-oxazolyl)phenyl]amino]-6-phenyl-1,3,5-triazin-2-yl]amino]-1,2-propanediol | 2.33/B | 435.37 |
| 150 | —NH(CH$_2$)$_3$(4-Me-piperazine) | N-[3-Methoxy-4-(5-oxazolyl)phenyl]-N'-[3-(4-methyl-1-piperazinyl)propyl]-6-phenyl-1,3,5-triazine-2,4-diamine | 1.33/B | 501.41 |
| 151 | —NHCH$_2$benzimidazol-2-yl | N-[3-Methoxy-4-(5-oxazolyl)phenyl]-N'-[3-(4-methyl-1-piperazinyl)propyl]-6-phenyl-1,3,5-triazine-2,4-diamine | 2.23/B | 491.41 |
| 152 | —NHCH(CH$_2$OH)(n-C$_3$H$_7$) | 2-[[4-[[3-Methoxy-4-(5-oxazolyl)phenyl]amino]-6-phenyl-1,3,5-triazin-2-yl]amino]-1-pentanol | 3.47/B | 447.36 |
| 153 | —NHCH$_2$furan-2-yl | N-(2-Furanylmethyl)-N'-[3-methoxy-4-(5-oxazolyl)phenyl]-6-phenyl-1,3,5-triazine-2,4-diamine | 3.77/B | 441.36 |
| 154 | —NH(CH$_2$)$_2$OPh | N-[3-Methoxy-4-(5-oxazolyl)phenyl]-N'-(2-phenoxyethyl)-6-phenyl-1,3,5-triazine-2,4-diamine | 4.28/B | 481.28 |
| 155 | —NH(CH$_2$)$_2$piperidin-1-yl | N-[3-Methoxy-4-(5-oxazolyl)phenyl]-6-phenyl-N'-[2-(1-piperidinyl)ethyl]-1,3,5-triazine-2,4-diamine | 1.85/B | 472.37 |
| 156 | —N[CH$_2$CH(OH)(CH$_3$)]$_2$ | S,S-1,1'-[[4-[[3-Methoxy-4-(5-oxazolyl)phenyl]amino]-6-phenyl-1,3,5-triazin-2-yl]imino]bis[2-propanol] | 3.37 | 477.57 |
| 157 | —N(n-C$_3$H$_7$)(CH$_2$cyclopropyl) | N-(Cyclopropylmethyl)-N'-[3-methoxy-4-(5-oxazolyl)phenyl]-6-phenyl-N-propyl-1,3,5-triazine-2,4-diamine | 2.75/E | 457.70 |
| 158 | —N(CH$_2$CH$_2$OH)[(CH$_2$)$_2$CH$_3$] | 2-[[4-[[3-Methoxy-4-(5-oxazolyl)phenyl]amino]-6-phenyl-1,3,5-triazin-2-yl]propylamino]ethanol | 3.98/B | 447.46 |
| 159 | —NHOH | 2-[[4-[[3-Methoxy-4-(5-oxazolyl)phenyl]amino]-6-phenyl-1,3,5-triazin-2-yl]propylamino]ethanol | 2.63/A | 376.23 |
| 160 | —NHCH$_2$ pyridin-4-yl | N-[3-Methoxy-4-(5-oxazolyl)phenyl]-6-phenyl-N'-(4-pyridinylmethyl)-1,3,5-triazine-2,4-diamine | 1.93 | 452.25 |
| 161 | 2-(CH$_2$OH)pyrrolidin-1-yl | (S)-1-[4-[[3-Methoxy-4-(5-oxazolyl)phenyl]amino]-6-phenyl-1,3,5-triazin-2-yl]-2-pyrrolidinemethanol | 3.75 | 445.27 |

TABLE 5-continued

| EX. No | R | CompoundName | HPLC time/ Conditions | M + H$^+$ |
|---|---|---|---|---|
| 162 | -4-formylpiperazin- | 4-[4-[[3-Methoxy-4-(5-oxazolyl)phenyl]amino]-6-phenyl-1,3,5-triazin-2-yl]-1-piperazinecarboxaldehyde | 3.57/B | 458.37 |
| 163 | 4-(CH$_2$CH$_2$OH)piperidin-1-yl | 1-[4-[[3-Methoxy-4-(5-oxazolyl)phenyl]amino]-6-phenyl-1,3,5-triazin-2-yl]-4-piperidineethanol | 4.09/B | 473.60 |
| 164 | —N(CH$_3$)(n-C$_3$H$_7$) | N'-[3-Methoxy-4-(5-oxazolyl)phenyl]-N-methyl-6-phenyl-N-propyl-1,3,5-triazine-2,4-diamine | 4.73/B | 417.31 |
| 165 | —N(CH$_3$)[CH$_2$CH$_2$N(CH$_3$)$_2$] | N-[2-(Diethylamino)ethyl]-N'-[3-methoxy-4-(5-oxazolyl)phenyl]-N-methyl-6-phenyl-1,3,5-triazine-2,4-diamine | 2.32/B | 460.33 |
| 166 | —N(C$_2$H$_5$)[CH$_2$CH$_2$N(C$_2$H$_5$)$_2$] | N-[2-(Dimethylamino)ethyl]-N-ethyl-N'-[3-methoxy-4-(5-oxazolyl)phenyl]-6-phenyl-1,3,5-triazine-2-4-diamine | 2.09/B | 474.64 |
| 167 | —N(I—C$_3$H$_7$)(CH$_2$CH$_2$OH) | 2-[[4-[[3-Methoxy-4-(5-oxazolyl)phenyl]amino]-6-phenyl-1,3,5-triazin-2-yl](1-methylethyl)amino]ethanol | 3.96/B | 447.31 |
| 168 | —N(C$_2$H$_5$)CH$_2$-pyridin-4-yl) | N-Ethyl-N'-[3-methoxy-4-(5-oxazolyl)phenyl]-6-phenyl-N-(4-pyridinylmethyl)-1,3,5-triazine-2,4-diamine | 2.77/B | 480.50 |
| 169 | 4-(CH$_2$CH$_2$OH)piperazin-1-yl | '1-[4-[[3-Methoxy-4-(5-oxazolyl)phenyl]amino]-6-phenyl-1,3,5-triazin-2-yl]-1-piperazineethanol | 2.02/B | 474.29 |
| 170 | -4-(OH) piperidi-1-yl | 1-[4-[[3-Methoxy-4-(5-oxazolyl)phenyl]amino]-6-phenyl-1,3,5-triazin-2-yl]-4-piperidinol | 3.60/B | 445.33 |
| 171 | 3(NHCOCH$_3$)pyrrolidin-1-yl) | N-[1-[4-[[3-Methoxy-4-(5-oxazolyl)phenyl]amino]-6-phenyl-1,3,5-triazin-2-yl]3-pyrrolidinyl]acetamide | 3.29/B | 472.47 |
| 172 | —N(CH$_2$CH$_2$OH)(CH$_2$Ph) | 2-[[4-[[3-Methoxy-4-(5-oxazolyl)phenyl]amino]-6-phenyl-1,3,5-triazin-2-yl](phenylmethyl)amino]-ethanol | 4.25/B | 495.36 |
| 173 | 4-CH$_3$ diazepin-1-yl | 4-[4-(Hexahydro-4-methyl-1H-1,4-diazepin-1-yl)-N-[3-methoxy-4-(5-oxazolyl)phenyl]-6-phenyl-1,3,5-triazin-2-amine | 2.06/B | 458.32 |
| 174 | —N(CH$_2$CH$_2$OH)(cyclohexyl) | 2-[Cyclohexyl[4-[[3-methoxy-4-(5-oxazolyl)phenyl]amino]-6-phenyl-1,3,5-triazin-2-yl]amino]ethanol | 4.53/B | 487.31 |
| 175 | 4-(CO$_2$C$_2$H$_5$)piperidin-1-yl | 1-[4-[[3-Methoxy-4-(5-oxazolyl)phenyl]amino]-6-phenyl-1,3,5-triazin-2-yl]-4-piperidinecarboxylic acid ethyl ester | 4.63/B | 501.29 |

TABLE 5-continued

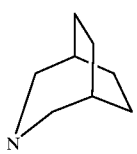

| EX. No | R | Compound Name | HPLC time/ Conditions | M + H⁺ |
|---|---|---|---|---|
| 176 | 4-(CH₂CO₂C₂H₅)piperizin-1-yl | 4-[4-[[3-Methoxy-4-(5-oxazolyl)phenyl]amino]-6-phenyl-1,3,5-triazin-2-yl]-1-piperazineacetic acid ethyl ester | 2.47/B | 516.47 |
| 177 | —N(CH₃)[(CH₂)₃N(C₂H₅)₂] | N-[3-(Diethylamino)propyl]-N'-[3-methoxy-4-(5-oxazolyl)phenyl]-N-methyl-6-phenyl-1,3,5-triazine-2,4-diamine | 2.23/B | 488.62 |
| 178 | —N(n-C₃H₇)(CH₂CH₂OCH₃) | N-[3-(Diethylamino)propyl]-N'-[3-methoxy-4-(5-oxazolyl)phenyl]-N-methyl-6-phenyl-1,3,5-triazine-2,4-diamine | 4.71/B | 461.57 |
| 179 | 2-(CONH₂pyrrolidin-1-yl | 1-[4-[[3-Methoxy-4-(5-oxazolyl)phenyl]amino]-6-phenyl-1,3,5-triazin-2-yl]-L-prolinamide | 3.06/B | 458.40 |
| 180 | 3-(OH)pyrrolidin-1-yl | 1-[4-[[3-Methoxy-4-(5-oxazolyl)phenyl]amino]-6-phenyl-1,3,5-triazin-2-yl]-3-pyrrolidinol | 3.26/B | 431.26 |
| 181 | thiomorpholin-4-yl | N-[3-Methoxy-4-(5-oxazolyl)phenyl]-6-phenyl-4-(4-thiomorpholinyl)-1,3,5-triazin-2-amine | 4.00/F | 447.40 |
| 182 | —N(CH₃)(n-C₄H₉) | N-[3-Methoxy-4-(5-oxazolyl)phenyl]-6-phenyl-4-(4-thiomorpholinyl)1,3,5-triazin-2-amine | 3.59/G | 431.30 |
| 183 | —N(CH₃)(CH₂Ph) | N'-[3-Methoxy-4-(5-oxazolyl)phenyl]-N-methyl-6-phenyl-N-(phenylmethyl)-1,3,5-triazine-2,4-diamine | 3.58/G | 465.32 |
| 184 | 2-(CH₂OCH₃)pyrrolidin-1-yl | (S)-4-[2-(Methoxymethyl)-1-pyrrolidinyl]-N-[3-methoxy-4-(5-oxazolyl)phenyl]-6-phenyl-1,3,5-triazin-2-amine | 3.67/F | 459.34 |
| 185 | | 4-(3-Azabicyclo[3.2.2]nonan-3-yl)-N-[3-methoxy-4-(5-oxazolyl)phenyl]-6-phenyl-1,3,5-triazin-2-amine | 4.44/G | 469.34 |
| 186 | —N(C₂H₅)(CH₂CH₂OCH₃) | N-Ethyl-N-(2-methoxyethyl)-N'-[3-methoxy-4-(5-oxazolyl)phenyl]-6-phenyl-1,3,5-triazine-2,4-diamine | 3.49/F | 447.31 |
| 187 | 4-(CH₂OH)piperidin-1-yl | 1-[4-[[3-Methoxy-4-(5-oxazolyl)phenyl]amino]-6-phenyl-1,3,5-triazin-2-yl]-4-piperidinemethanol | 3.78/B | 459.42 |

TABLE 5-continued

| EX. No | R | CompoundName | HPLC time/ Conditions | M + H+ |
|---|---|---|---|---|
| 188 | —N(CH₂CH₂OH)(n-C₄H₉) | 2-[Butyl[4-[[3-methoxy-4-(5-oxazolyl)phenyl]amino]-6-phenyl-1,3,5-triazin-2-yl]amino]ethanol | 3.21/F | 461.45 |
| 189 | imidazol-1-yl | 4-(1H-Imidazol-1-yl)-N-[3-methoxy-4-(5-oxazolyl)phenyl]-6-phenyl-1,3,5-triazin-2-amine | 3.17/B | 412.26 |
| 190 | —NH(CH₂CO₂t-bu) | N-[4-[[3-Methoxy-4-(5-oxazolyl)phenyl]amino]-6-phenyl-1,3,5-triazin-2-yl]glycine 1,1-dimethylethyl ester | 3.77/B | 475.59 |
| 191 | —NH(CH₂CO₂H) | N-[4-[[3-Methoxy-4-(5-oxazolyl)phenyl]amino]-6-phenyl-1,3,5-triazin-2-yl]glycine | 2.72/B | 419.26 |
| 192 | —NH(CH₂)CO₂H | 4-[[4-[[3-Methoxy-4-(5-oxazolyl)phenyl]amino]-6-phenyl-1,3,5-triazin-2-yl]amino]butanoic acid | 2.82/B | 447.38 |
| 193 | —NH(CH₂)₃pyrrolidin-1-yl | N-[3-Methoxy-4-(5-oxazolyl)phenyl]-N'-[3-(1-pyrrolidinyl)propyl]-6-phenyl-1,3,5-triazine-2,4-diamine | 1.60/B | 472.56 |
| 194 | —NH(CH₂)₃pyrrolid-2-on-1-yl | N-[3-Methoxy-4-(5-oxazolyl)phenyl]-N'-[3-(1-pyrrolidinyl)propyl]-6-phenyl-1,3,5-triazine-2,4-diamine | 2.83/B | 486.56 |
| 195 | —NHCH[CH₂OCH₃][CH(OH)(Ph)] | [S-(R*,R*)]-∀-[2-Methoxy-1-[[4-[[3-methoxy-4-(5-oxazolyl)phenyl]amino]-6-phenyl-1,3,5-triazin-2-yl]amino]ethyl]benzenemethanol | 3.52/B | 525.49 |
| 196 | 2-(CH₂OH)pyrrolidin-1-yl | (R)-1-[4-[[3-Methoxy-4-(5-oxazolyl)phenyl]amino]-6-phenyl-1,3,5-triazin-2-yl]-2-pyrrolidinemethanol | 3.65/B | 445.37 |
| 197 | —NHCH(CH₂OH)(CO₂CH₃) | N-[4-[[3-Methoxy-4-(5-oxazolyl)phenyl]amino]-6-phenyl-1,3,5-triazin-2-yl]-DL-serine methyl ester | 2.93/B | 463.15 |
| 198 | pyrrolidin-1yl | N-[3-Methoxy-4-(5-oxazolyl)phenyl]-4-phenyl-6-(1-pyrrolidinyl)-1,3,5-triazin-2-amine | 4.04/C | 415.28 |
| 199 | —OCH₂CH(CH₃)₂ | N-[3-Methoxy-4-(5-oxazolyl)phenyl]-4-(2-methylpropoxy)-6-phenyl-1,3,5-triazin-2-amine | 4.62/B | 418.38 |
| 200 | —OCH₂Ph | N-[3-Methoxy-4-(5-oxazolyl)phenyl]-4-phenyl-6-(phenylmethoxy)-1,3,5-triazin-2-amine | 4.24/B | 452.26 |
| 201 | —OCH₂pyridin-3-yl | N-[3-Methoxy-4-(5-oxazolyl)phenyl]-4-phenyl-6-(3-pyridinylmethoxy)-1,3,5-triazin-2-amine | 2.53/B | 453.26 |

TABLE 5-continued

| EX. No | R | CompoundName | HPLC time/ Conditions | M + H+ |
|---|---|---|---|---|
| 202 | —OCH₂CH₂OH | 2-[[4-[[3-Methoxy-4-(5-oxazolyl)phenyl]amino]-6-phenyl-1,3,5-triazin-2-yl]oxy]ethanol | 3.09/B | 406.23 |
| 203 | —O(tetrahydrofuran-3-yl) | N-[3-Methoxy-4-(5-oxazolyl)phenyl]-4-phenyl-6-[(tetrahydro-3-furanyl)oxy]-1,3,5-triazin-2-amine | 3.64/B | 432.23 |
| 204 | —OCH(CH₃)₂ | N-[3-Methoxy-4-(5-oxazolyl)phenyl]-4-(1-methylethoxy)-6-phenyl-1,3,5-triazin-2-amine | 4.21/B | 404.26 |
| 205 | —OCH₂CH₂OCH3 | N-[3-Methoxy-4-(5-oxazolyl)phenyl]-4-(1-methylethoxy)-6-phenyl-1,3,5-triazin-2-amine | 8.53/H | 420.23 |
| 206 | —OPh | N-[3-Methoxy-4-(5-oxazolyl)phenyl]-4-(1-methylethoxy)-6-phenyl-1,3,5-triazin-2-amine | 4.36/B | 438.25 |
| 207 | —SPh | N-[3-Methoxy-4-(5-oxazolyl)phenyl]-4-phenyl-6-phenylthio)-1,3,5-triazin-2-amine | 4.71/B | 454.25 |
| 208 | —OCH₂CH(OH)(CH₃) | 1-[[4-[[3-Methoxy-4-(5-oxazolyl)phenyl]amino]-6-phenyl-1,3,5-triazin-2-yl]oxy]-2-propanol | 3.42/B | 420.23 |
| 209 | —NHCH(CH₂OH)₂ | 2-[[4-[[3-Methoxy-4-(5 oxazolyl)phenyl]amino]-6-phenyl-1,3,5-triazin-2-yl]amino]-1,3-propanediol | 2.10/B | 435.33 |
| 210 | —NHC(CH₂OH)₃ | 2-[[4-[[3-Methoxy-4-(5-oxazolyl)phenyl]amino]-6-phenyl-1,3,5-triazin-2-yl]amino]-1,3-propanediol | 2.15/B | 465.37 |
| 211 | —NHC(CH₃)(CH₂OH)₂ | 2-[[4-[[3-Methoxy-4-(5 oxazolyl)phenyl]amino]-6-phenyl-1,3,5-triazin-2-yl]amino]-1,3-propanediol | 2.46/B | 449.36 |
| 212 | NHCH(CH₂OH)[CH(OH)(Ph)] | [S-(R*,S*)]-2-[[4-[[3-Methoxy-4-(5-oxazolyl)phenyl]amino]-6-phenyl-1,3,5-triazin-2-yl]amino]-1-phenyl-1,3-propanediol | 2.93/B | 511.32 |
| 213 | OH | 2-[[3-Methoxy-4-(5-oxazolyl)phenyl]amino]-6-phenyl-4(3H)-triazinone | 2.09/B | 362.30 |

EXAMPLE 214

N-[3-Methoxy-4-(5-oxazolyl)phenyl]-N'-methyl-6-(1-pyrrolidinyl)-1,3,5-triazine-2,4-diamine (A201)

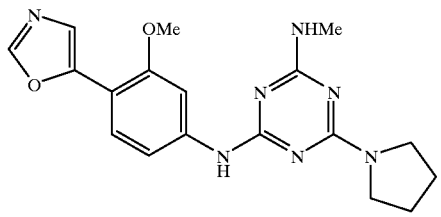

Example 214 Part A 2,4-Dichloro-6-(4-oxazol-5-yl-3-methoxyphenylamino)triazine

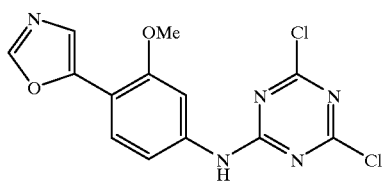

Cyanuric chloride (1.84 g, 10 mmol) and pulverized potassium carbonate (4.14 g, 30 mmol) were suspended in acetone (50 mL) and cooled in an ice salt bath. 4-Oxazol-5-yl-3-methoxyaniline (1.90 g, 10 mmol) was added dropwise and stirred for 2 h. The crude product was filtered and resuspended in 100 mL of 0.1N NaOH and 200 mL of ethyl acetate, and filtered. The product was dried to yield 2.12 g, 63% of the title compound. LCMS condition B retention time=3.47 min (100%) M+H+=338, 340 (100%, 70%).

Example 214 Part B
2-Chloro-4-methylamino-6-(4-oxazol-5-yl-3-methoxyphenylamino)triazine

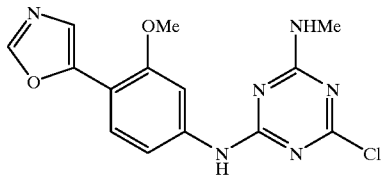

2,4-Dichloro-6-(4-oxazol-5-yl-3-methoxyphenylamino)triazine 214A (1.8 g, 5.4 mmol) was suspended in dimethoxyethane (50 mL). 2 M Methylamine in THF (27 mL, 54 mmol) was added dropwise and the reaction mixture stirred for 3 h. The crude product was filtered and triturated with ethanol (20 mL) and dried to yield 1.37 g (77%) of the title compound. LCMS Condition A retention time=2.61 min (>95%), M+H$^+$=333.16 (100%).

Example 214 Part C
N-[3-Methoxy-4-(5-oxazolyl)phenyl]-N'-methyl-6-(1-pyrrolidinyl)-1,3,5-triazine-2,4-diamine 2-Chloro-4-methylamino-6-(4-oxazol-5-yl-3-methoxyphenylamino)triazine, 214B, (41 mg, 0.12 mmol) was suspended in dimethoxyethane (5 mL) and dimethylformamide (0.5 ml). Pyrrolidine (88 mg, 1.2 mmol) was added and the reaction mixture heated overnight at 50° C. The product was filtered and triturated with ether (5 mL) to yield 22.6 mg (50%) of the title compound. LCMS condition D retention time=3.47 min (100%) M+H$^+$=368.31 (100%).

EXAMPLES 215 TO 241

The compounds in Table 6 below were prepared in a manner similar to that described for N-[3-Methoxy-4-(5-oxazolyl)phenyl]-N'-methyl-6-(1-pyrrolidinyl)-1,3,5-triazine-2,4-diamine, (Example 214) from the intermediate 2-chloro-4-methylamino-6-(4-oxazol-5-yl-3-methoxyphenylamino)triazine (Example 214 Part B), or a similar intermediate useful for this invention. The chlorotriazine intermediate was generally heated for 4–24 h in a solvent such as dimethoxyethane or THF in the presence of 5 to 10 equivalents of a desired amine. The product was generally purified by reverse phase HPLC to yield the products in the table below. The above method does not constitute a limitation on this invention.

TABLE 6

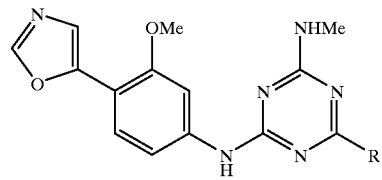

| EX. No | R | Compound Name | HPLC time/ Conditions | M + H$^+$ |
|---|---|---|---|---|
| 215 | 4-methylpiperazin-1-yl | N-[3-Methoxy-4-(5-oxazolyl)phenyl]-N'-methyl-6-(4-methyl-1-piperazinyl)-1,3,5-triazine-2,4-diamine | 0.69/J | 397.36 |

TABLE 6-continued

| EX. No | R | Compound Name | HPLC time/ Conditions | M + H⁺ |
|---|---|---|---|---|
| 216 | 4-formylpiperazin-1-yl | 4-[4-[[3-Methoxy-4-(5-oxazolyl)phenyl]amino]-6-(methylamino)-1,3,5-triazin-2-yl]-1-piperazinecarboxaldehyde | 2.85/A | 411.28 |
| 217 | morpholin-4-yl | N-[3-Methoxy-4-(5-oxazolyl)phenyl]-N'-methyl-6-(4-morpholinyl)-1,3,5-triazine-2,4-diamine | 1.51/A | 383.29 |
| 218 | 2-(CH₂OH)piperidin-1-yl | 1-[4-[[3-Methoxy-4-(5-oxazolyl)phenyl]amino]-6-(methylamino)-1,3,5-triazin-2-yl]-2-piperidinemethanol | 1.93/A | 412.27 |
| 219 | 3-[CON(C₂H₅)₂]piperidin-1-yl | N,N-Diethyl-1-[4-[[3-methoxy-4-(5-oxazolyl)phenyl]amino]-6-(methylamino)-1,3,5-triazin-2-yl]-3-piperidinecarboxamide | 2.01/A | 481.40 |
| 220 | 4-OH piperidin-1-yl | 1-[4-[[3-Methoxy-4-(5-oxazolyl)phenyl]amino]-6-(methylamino)-1,3,5-triazin-2-yl]-4-piperidinol | 2.41/K | 398.30 |
| 221 | 3-OH piperidin-1-yl | (R)-1-[4-[[3-Methoxy-4-(5-oxazolyl)phenyl]amino]-6-(methylamino)-1,3,5-triazin-2-yl]-3-piperidinol | 2.53/K | 398.30 |
| 222 | 2-C₂H₅ piperidin-1-yl | 6-(2-Ethyl-1-piperidinyl)-N-[3-methoxy-4-(5-oxazolyl)phenyl]-N'-methyl-1,3,5-triazine-2,4-diamine | 2.97/A | 410.30 |
| 223 | 2-(CONH₂)pyrrolidin-1-yl | 1-[4-[[3-Methoxy-4-(5-oxazolyl)phenyl]amino]-6-(methylamino)-1,3,5-triazin-2-yl]-L-prolinamide | 2.03/K | 411.28 |
| 224 | 2-(CH₂OCH₃)pyrrolidin-1-yl | (S)-6-[2-(Methoxymethyl)-1-pyrrolidinyl]-N-[3-methoxy-4-(5-oxazolyl)phenyl]-N'-methyl-1,3,5-triazine-2,4-diamine | 2.04/A | 412.34 |
| 225 | 2-(CO2t-bu) pyrrolidin-1-yl | 1-[4-[[3-Methoxy-4-(5-oxazolyl)phenyl]amino]-6-(methylamino)-1,3,5-triazin-2-yl]-L-proline 1,1-dimethylethyl ester | 2.45/A | 468.43 |
| 226 | 2-(CH₂OH) pyrrolidin-1-yl | (R)-1-[4-[[3-Methoxy-4-(5-oxazolyl)phenyl]amino]-6-(methylamino)-1,3,5-triazin-2-yl]-2-pyrrolidinemethanol | 1.47/A | 398.32 |
| 227 | 3-(N(CH₃)COCH₃) pyrrolidin-1-yl | N-[1-[4-[[3-Methoxy-4-(5-oxazolyl)phenyl]amino]-6-(methylamino)-1,3,5-triazin-2-yl]-3-pyrrolidinyl]-N-methylacetamide | 1.09/A | 439.38 |
| 228 | 2-(CH₂OCH₃) pyrrolidin-1-yl | (R)-6-[2-(Methoxymethyl)-1-pyrrolidinyl]-N-[3-methoxy-4-(5-oxazolyl)phenyl]-N'-methyl-1,3,5-triazine-2,4-diamine | 2.03/A | 412.27 |

TABLE 6-continued

| EX. No | R | Compound Name | HPLC time/ Conditions | M + H⁺ |
|---|---|---|---|---|
| 229 | 3-(CH₂OH) piperidin-1-yl | 1-[4-[[3-Methoxy-4-(5-oxazolyl)phenyl]amino]-6-(methylamino)-1,3,5-triazin-2-yl]-3-piperidinemethanol | 1.68/A | 412.23 |
| 230 | 4-(CONH₂) piperidin-1-yl | 1-[4-[[3-Methoxy-4-(5-oxazolyl)phenyl]amino]-6-(methylamino)-1,3,5-triazin-2-yl]-4-piperidinecarboxamide | 0.80/A | 425.26 |
| 231 | 2-(CH₂CO₂C₂H₅)-3-oxopiperazin-1-yl | 1-[4-[[3-Methoxy-4-(5-oxazolyl)phenyl]amino]-6-(methylamino)-1,3,5-triazin-2-yl]-3-oxo-2-piperazineacetic acid ethyl ester | 2.51/K | 483.26 |
| 232 | 2,5-dimethylpyrrolidin-1-yl | 6-(2,5-Dimethyl-1-pyrrolidinyl)-N-[3-methoxy-4-(5-oxazolyl)phenyl]-N'-methyl-1,3,5-triazin-2,4-diamine | 2.60/A | 396.29 |
| 233 | 3-OH pyrrolidin-1-yl | 1-[4-[[3-Methoxy-4-(5-oxazolyl)phenyl]amino]-6-(methylamino)-1,3,5-triazin-2-yl]-3-pyrrolidinol | 0.99/A | 384.25 |
| 234 | 3-N(CH₃)₂ pyrrolidin-1-yl | (S)-6-[3-(Dimethylamino)-1-pyrrolidinyl]-N-[3-methoxy-4-(5-oxazolyl)phenyl]-N'-methyl-1,3,5-triazine-2,4-diamine | 2.09/D | 411.28 |
| 235 | 3-(NCO₂t-bu) pyrrolidin-1-yl | (R)-[1-[4-[[3-Methoxy-4-(5-oxazolyl)phenyl]amino]-6-(methylamino)-1,3,5-triazin-2-yl]-3-pyrrolidinyl]carbamic acid 1,1-dimethylethyl ester | 2.39/A | 483.32 |
| 236 | 3-(CO₂CH₃)-4-oxopiperidin-1-yl | 1-[4-[[3-Methoxy-4-(5-oxazolyl)phenyl]amino]-6-(methylamino)-1,3,5-triazin-2-yl]-4-oxo-3-piperidinecarboxylic acid methyl ester | 2.65/A | 454.26 |
| 237 | 2-(CH₂OH) pyrrolidin-1-yl | (S)-1-[4-[[3-Methoxy-4-(5-oxazolyl)phenyl]amino]-6-(methylamino)-1,3,5-triazin-2-yl]-2-pyrrolidinemethanol | 3.08/D | 398.25 |
| 238 | 2-(CH₂pyrrolidin-1-yl)pyrrolidin-1-yl | (S)-1-[4-[[3-Methoxy-4-(5-oxazolyl)phenyl]amino]-6-(methylamino)-1,3,5-triazin-2-yl]-2-pyrrolidinemethanol | 2.33/D | 451.32 |
| 239 | 2-(CO₂C₂H₅) piperidin-1-yl | 1-[4-[[3-Methoxy-4-(5-oxazolyl)phenyl]amino]-6-(methylamino)-1,3,5-triazin-2-yl]-2-piperidinecarboxylic acid ethyl ester | 2.71/A | 454.28 |

TABLE 6-continued

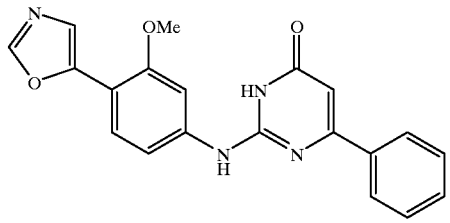

| EX. No | R | Compound Name | HPLC time/ Conditions | M + H⁺ |
|---|---|---|---|---|
| 240 | Piperazin-1-yl | 1-[4-[[3-Methoxy-4-(5-oxazolyl)phenyl]amino]-6-(methylamino)-1,3,5-triazin-2-yl]-2-piperidinecarboxylic acid ethyl ester | 2.09/D | 383 |
| 241 | 3-amino pyrrolidin-1-yl | 1-[4-[[3-Methoxy-4-(5-oxazolyl)phenyl]amino]-6-(methylamino)-1,3,5-triazin-2-yl]-2-piperidinecarboxylic acid ethyl ester | 2.20/D | 383 |

EXAMPLE 242

2-[[3-Methoxy-4(5-oxazolyl)phenyl]amino]-6-phenyl-4(3H)-pyrimidinone

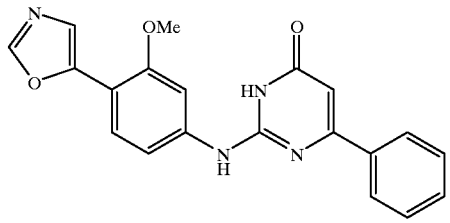

242

Example 242 Part A

4-Oxazol-5-yl-3-methoxyphenylguanidine

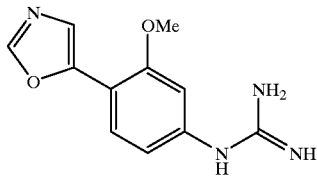

242A 5-(4-Amino-2-methoxyphenyl)oxazole, 1D, (0.30 g, 1.58 mmol) and 1,3 bis(tert-butoxycarbonyl)-2-methyl-2-thiopseudourea (428 mg, 1.66 mmol) were dissolved in N,N-dimethylformamide. Triethylamine (478 mg, 4.74 mmol) and mercury chloride (472 mg, 1.74 mmol) were added and the reaction mixture was allowed to stir at room temperature overnight. The reaction mixture was diluted with ethyl acetate (30 mL) and filtered to remove the white solid. The filtrate was washed with saturated sodium bicarbonate solution (25 mL), twice with water (25 mL) and brine (25 mL), dried over magnesium sulfate and evaporated to yield N-4-Oxazol-5-yl-3-methoxyphenyl-N',N"-bis t-butyloxycarbonylguanidine. LCMS conditions C retention time=3.20 min, (96%) M+H⁺=433.49 (100%). The product was dissolved in precooled trifluoroacetic acid (5 mL) at 0° C. and stirred at room temperature for 15 min. The solvent was evaporated to yield a red oil which was triturated with ether (20 ml) until a yellow solid precipitated. The solid was collected and dried to yield 4-oxazol-5-yl-3-methoxyphenylguanidine trifluoroacetate salt. LCMS conditions D retention time=1.51 min, (98%) M+H⁺=233.14 (100%). The salt was dissolved in methanol (50 mL) and AG1-X8 resin hydroxide (BioRad) was added and the mixture stirred for 0.5 h. The solid was filtered and the filtrate was concentrated to yield the title compound 242A, 297 mg 81% ¹NMR (400 mHz) (d-MeOH) 3.96 (s, 3H), 6.68–6.74 (m, 2H), 7.42 (s, 1H), 7.69 (d, J=8.18, 1H), 8.18 (s, 1H).

Example 242 Part B

2-[[3-Methoxy-4-(5-oxazolyl)phenyl]amino]-6-phenyl-4(3H)-pyrimidinone

The product of example 242A, (116 mg, 0.50 mmol) and ethyl benzoyl acetate (81 mg, 0.42 mmol) were added to anhydrous ethanol (1 mL) and heated to reflux. The crude product was filtered and triturated with ether, and dried to yield 50 mg 28% of the title compound. LCMS condition A retention time=3.16 min,(86%), M+H⁺=361.28 (100%).

EXAMPLE 243

N-[3-Methoxy-4-(5-oxazolyl)phenyl]-5-phenyl-1H-imidazol-2-amine

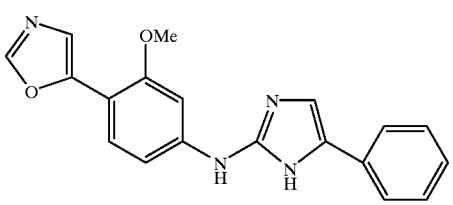

243

The product of Example 243, Part A, 4-Oxazol-5-yl-3-methoxyphenylguanidine, 243A (150 mg, 0.65 mmol) and phenacylbromide (128 mg, 0.65 mmol) were dissolved in N,N-dimethylformamide (0.25 mL) and stirred at room temperature for 3 days. The reaction mixture was evaporated and purified by prep RPHPLC to yield 5 mg (2%, a significant portion of the product was spilled during isolation) of the title compound. LCMS conditions J, retention time=1.62 min, (90%), M+H$^+$=333.17. (100%).

EXAMPLE 244

6-(2-Furanyl)-N-[3-methoxy-4-(5-oxazolyl)phenyl]-N'-methyl-1,3,5-triazine-2,4-diamine

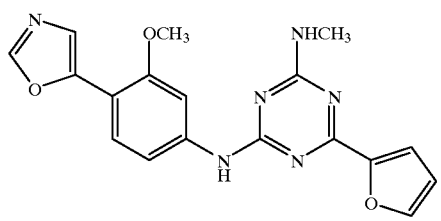

244

A mixture of 2-Chloro-4-methylamino-6-(4-oxazol-5-yl-3-methoxyphenylamino)triazine, 214B, (50 mg, 0.151 mmol), 2-(tributylstannyl)furan (170 mg, 0.462 mmol), tetrakis(triphenylphosphine)palladium(0) (18 mg, 0.015 mmol) and triphenylphosphine (8.1 mg, 0.03 mmol) in N-methyl-2-pyrrolidinone (2 mL) was heated to 100° C. for 28 hours. The reaction mixture was concentrated to yield a crude product to which was added 20 mL of ethyl acetate. The solid was removed with filtration and then the solution was concentrated to give a crude product which was purified with prep TLC plate with CH$_2$Cl$_2$. The isolated crude product was dissolved in methanol (10 mL) and stood at room temperature for 2 days. The solid was precipitated out which was collected as the title compound (5.2 mg, 9.5%). NMR (CDCl$_3$): δ8.36 (1H, s), 7.20–8.20 (6H, m), 6.90 (1H, m), 3.97 (3H, s), 2.91 (3H, s); LC-MS: m/z 365.23 (M+H)$^+$

EXAMPLES 245–256

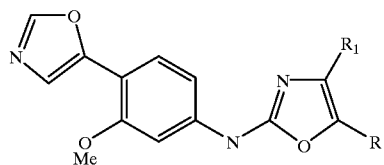

Compounds 245 to 256 were prepared from 1E by a route analogous to that used in example 34, replacing phenacyl azide with an appropriately substituted azide. The azides can be made by one of the many methods outlined in scheme 15. The compounds of these examples have structures outlined in Table 7 below.

TABLE 7*

| Example | R | R$_1$ | Name | HPLC time (min) | M$^+$ |
|---|---|---|---|---|---|
| 245 | (H$_3$C-N-CH$_2$-C(O)-N-piperidine structure) | H | N-[2-[2-[[3-Methoxy-4-(5-oxazolyl)phenyl]amino]-5-oxazolyl]phenyl]-N-methyl-1-piperidineacetamide | 1.52 | 488.5 |
| 246 | (H$_3$C-N-CH$_2$-C(O)-N-4-hydroxypiperidine structure) | H | 4-Hydroxy-N-[2-[2-[[3-methoxy-4-(5-oxazolyl)phenyl]amino]-5-oxazolyl]phenyl]-N-methyl-1-piperidineacetamide | 1.50 | 504.5 |
| 247 | (Me-N-CH$_2$-C(O)-N(Me)-cyclohexyl structure) | H | 2-(Cyclohexylmethylamino)-N-[2-[2-[[3-methoxy-4-(5-oxazolyl)phenyl]amino]-5-oxazolyl]phenyl]-N-methylacetamide | 1.58 | 517.6 |

TABLE 7*-continued

| Example | R | R₁ | Name | HPLC time (min) | M⁺ |
|---|---|---|---|---|---|
| 248 | | H | N-[2-[2-[[3-Methoxy-4-(5-oxazolyl)phenyl]amino]-5-oxazolyl]phenyl]-N,2-dimethyl-1-piperidineacetamide | 1.52 | 502.6 |
| 249 | | H | (S)-2-(Methoxymethyl)-N-[2-[2-[[3-methoxy-4-(5-oxazolyl)phenyl]amino]-5-oxazolyl]phenyl]-N-methyl-1-pyrrolidineacetamide | 1.54 | 518.4 |
| 250 | | H | 2-Amino-N-[2-[2-[[3-methoxy-4-(5-oxazolyl)phenyl]amino]-5-oxazolyl]phenyl]-N-methylacetamide | 1.45 | 420.3 |
| 251 | | H | N-[2-[2-[[3-Methoxy-4-(5-oxazolyl)phenyl]amino]-5-oxazolyl]phenyl]-N,2-dimethylpropanamide | 8.28[a] | 433. |
| 252 | | H | N-[2-[2-[[3-Methoxy-4-(5-oxazolyl)phenyl]amino]-5-oxazolyl]phenyl]-2,2-dimethylpropanamide | 7.55[a] | 433 |
| 253 | | H | [[2-[2-[[3-Methoxy-4-(5-oxazolyl)phenyl]amino]-5-oxazolyl]phenyl]methylamino]oxoacetic acid ethyl ester | 1.83 | 463 |

TABLE 7*-continued

| Example | R | R₁ | Name | HPLC time (min) | M⁺ |
|---|---|---|---|---|---|
| 254 | ![structure] | H | [[2-[2-[[3-Methoxy-4-(5-oxazolyl)phenyl]amino]-5-oxazolyl]phenyl]methylamino]oxoacetic acid | 1.83 | 435 |
| 255 | ![structure] | H | 2-[2-[[3-Methoxy-4-(5-oxazolyl)phenyl]amino]-5-oxazolyl]benzeneacetic acid phenylmethyl ester | 2.06 | 482.5 |
| 256 | ![structure] | H | N-[(1-Ethyl-3-pyrrolidinyl)methyl]-2-[2-[[3-methoxy-4-(5-oxazolyl)phenyl]amino]-5-oxazolyl]benzeneacetamide | 1.62 | 502.74 |

*Column: YMC S50 Turbopac Pro 4.6 × 5.0 mm Ballistic. Solvent A = 10% MeOH, 90% H₂O, 0.1% TFA; Solvent B = 90% MeOH, 10% H₂O, 0.1% TFA. Flow rate: 4 mL/min. Gradient: 2 min.
ªZorbax SB C18 4.6 × 75 column. Solvent A = 10% MeOH, 90% H₂O, 0.1% TFA; Solvent B = 90% MeOH, 10% H₂O, 0.1% TFA. 0% B to 100% B linear gradient over 8 min. at 2.5 ml/min.

EXAMPLE 257

2-(Acetyloxy)-N-[2-[2-[[3-bromo-4-(5-oxazolyl)phenyl]amino]-5-oxazolyl]phenyl]-N-methylacetamide

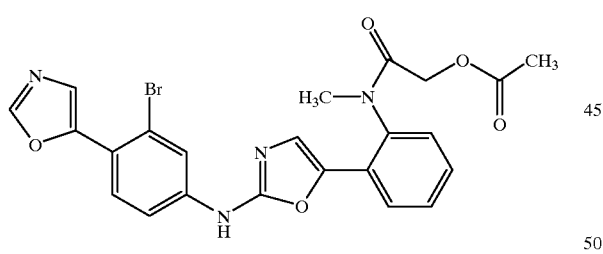

257

Example 257 Part A

N-[2-(Azidoacetyl)phenyl]-N-methyl-2-acetoxyacetamide

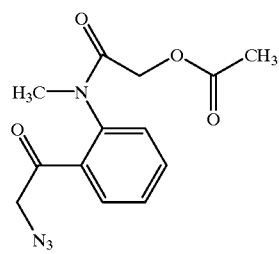

257A

The product of example 257 Part A was prepared in similar manner to the azide in example 79E. ¹H 400 MHz NMR (CD₃OD): δ7.70–7.29 (m, 5H), 4.37–4.14 (m, 4H), 3.16 (s, 3H), 2.40 (s, 3H).

Example 257 Part B 5-(4-Amino-2-bromophenyl)oxazole

257B

2-Bromo-4nitrotoluene (6.29 g, 29.1 mmol) was dissolved in a mixture of glacial acetic acid 46 mL, and acetic anhydride 46 mL, and cooled in an ice bath. Concentrated sulfuric acid (6.9 mL) was added dropwise. Chromium trioxide (8.08 g, 80.8 mmol) was added portionwise over 1 h. The reaction mixture was stirred for an additional 15 min then poured onto ice. The precipitate was isolated by filtration and dissolved in 16 mL of 1,4-dioxane. Concentrated hydrochloric acid (3 mL) was added and the solution was refluxed for 2 h. The reaction mixture was diluted with ethyl acetate (150 mL) and washed with water, saturated sodium bicarbonate and brine. The organic layer was dried over magnesium sulfate and evaporated to yield 1.09 g of 2-bromo-4-nitrobenzaldehyde. The aldehyde was dissolved in methanol (50 mL) and potassium carbonate (0.82 g, 5.96 mmol) and tosylmethyl isocyanide (1.16 g, 5.96 mmol) was added. The reaction mixture was refluxed for 3 h, cooled to room temperature and concentrated. The residue was dissolved in methylene chloride (200 mL) and the organic layer was washed with water and brine. The organic layer was dried over magnesium sulfate, filtered and concentrated to yield 1.53 g. (96%) of 5-(4-nitro-2-bromophenyl)oxazole. 5-(4-Nitro-2-bromophenyl)oxazole (500 mg, 1.86 mmol) was dissolved in a mixture of 10 mL of ethanol and 20 ml of ethyl acetate. Tin dichloride dihydrate 1.74 g (7.72 mmol) was added and the reaction mixture heated to 80° C. for 0.5 h. The reaction mixture was poured into 400 mL of ice/water and neutralized with sodium carbonate. The suspension was extracted with ethyl acetate (3×100 mL), and the combined organic layer was washed with brine, separated and dried over magnesium sulfate, filtered and the solvent removed under reduced pressure to yield 463 mg of 5-(4-amino-2-bromophenyl)oxazole. 93% pure by HPLC method A. Mass spectrum M+H$^+$=240.95, $^1$H 400 MHz NMR (CD$_3$OD): 8.09 (s, 1H), 7.40 (s, 1H), 7.34 (d, 1H J=8.5 Hz), 6.89 (d, 1H, J=8.5 Hz), 6.60 (m, 1H).

Example 257 Part C 2-(Acetyloxy)-N-[2-[2-[[3-bromo-4-(5-oxazolyl) phenyl]amino]-5-oxazolyl]phenyl]-N-methylacetamide The product 257B was converted to the isothiocyanate in a manner similar to that described in example 1 part E, and reacted with the azide 257A, in a manner similar to that described in example 79 part F to provide the title compound. HPLC: Column: YMC S5 ODS 4.6×50 mm Ballistic; Gradient time: 4 min; Flow rate=4 ml/min; Solvent A=10% MeOH 90% Water, 0.2% H$_3$PO$_4$; Solvent B=90% MeOH 10% water 0.2% H$_3$PO$_4$;Start % B=0; Final % B=100. Retention time: 4.08 min. Mass spectrum M+H$^+$=513.3.

EXAMPLE 258

N-[2-[2-[[3-Bromo-4-(5-oxazolyl)phenyl]amino]-5-oxazolyl]phenyl]-2-hydroxy-N-methylacetamide

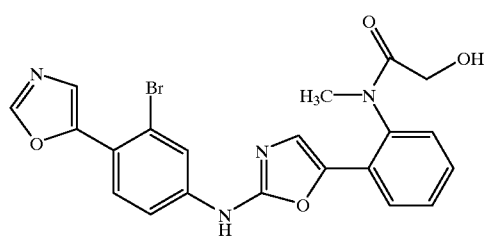

258

The product of Example 257 (531 mg, 1.04 mmol) was disolved in methanol (12 mL) and water (5 mL). Lithium hydroxide (65.4 mg, 1.56 mmol) was added and the reaction mixture stirred at room temperature for 0.5 h. The product was collected by filtration to yield 412 mg (87%) of the title compound. HPLC: Column: YMC S5 ODS 4.6×50 mm Ballistic; Gradient time: 4 min; Flow rate=4 ml/min; Solvent A 10% MeOH—90% Water—0.2% H$_3$PO$_4$; Solvent B=90% MeOH—10% water—0.2% H$_3$PO$_4$; Start % B=0; Final % B=100. Retention time: 4.89 min. Mass spectrum M+H$^+$=471.2.

EXAMPLE 259

N-[2-[2-[[3-Bromo-4-(5-oxazolyl)phenyl]amino]-5-oxazolyl]phenyl]-N-methyl-4-morpholineacetamide

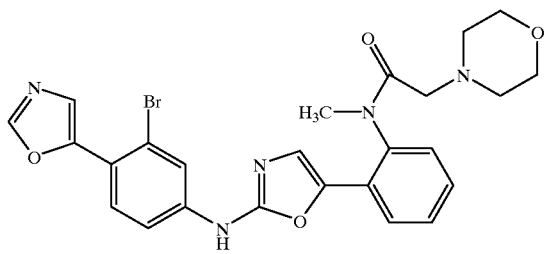

259

The isocyanate described in example 257 part C was reacted with the azide from example 79E in a manner similar to that described for example 257C to provide the title product. HPLC: Column: YMC S5 ODS 4.6×50 mm Ballistic; Gradient time: 4 min; Flow rate=4 ml/min; Solvent A=10% MeOH 90%, Water, 0.2% H$_3$PO$_4$; Solvent B=90% MeOH 10%, water, 0.2% H$_3$PO$_4$; Start % B=0; Final % B=100. Retention time: 3.36 min. Mass spectrum M+H+= 538.1

EXAMPLE 260

N-[2-[2-[[3-Chloro-4-(5-oxazolyl)phenyl]amino]-5-oxazolyl]phenyl]-2-hydroxy-N-methylacetamide

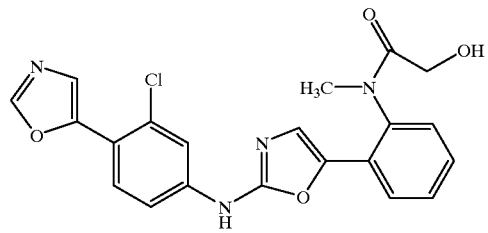

260

Example 260 Part A 5-(4-Amino-2-chlorophenyl)oxazole

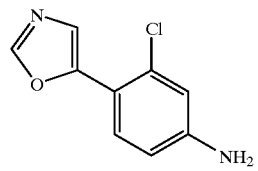

260A

The product of example 260 part A was prepared in a manner similar to that described for example 248 part B, starting with 2-chloro-4-nitrotoluene. 97% pure by HPLC method A. Mass spectrum M+H$^+$=195.05, $^1$H 400 MHz NMR (CD$_3$OD): 8.09 (s, 1H), 7.41 (d, 1H, J=8.57 Hz) 7.36 (s, 1H), 6.69 (d, 1H, J=2.18H), 6.58 (m, 1H).

Example 260 Part B

N-[2-[2-[[3-Chloro-4-(5-oxazolyl)phenyl]amino]-5-oxazolyl]phenyl]-2-hydroxy-N-methylacetamide The aniline 260A was converted to the isothiocyanate in a similar manner to that described in example 1 part E. The isothiocyanate was reacted with azide 257A in a manner similar to that described for example 79 part F. The resulting acetate was hydrolyzed in a manner similar to that described for example 258. HPLC: Column: YMC S5 ODS 4.6×50 mm Ballistic; Gradient time: 4 min; Flow rate=4 ml/min; Solvent A=10% MeOH 90%, Water, 0.2% $H_3PO_4$; Solvent B=90% MeOH, 10% water, 0.2% $H_3PO_4$; Start % B=0; Final % B=100. Retention time: 3.98 min. Mass spectrum $M+H^+=425.9$.

EXAMPLE 261

N-[2-[2-[[3-Chloro-4-(5-oxazolyl)phenyl]amino]-5-oxazolyl]phenyl]-N-methyl-4-morpholineacetamide

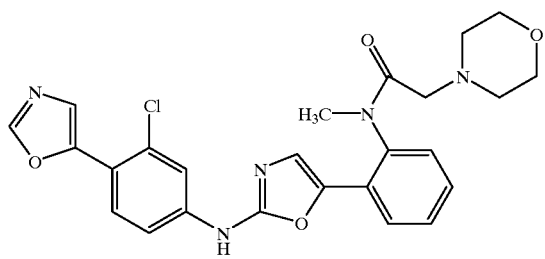

261

The aniline 260A was converted to the isothiocyanate in a similar manner to that described in example 1 part E. The isothiocyanate was reacted with the azide from example 79E in a manner similar to that described for example 257C to provide the title product. HPLC: Column: YMC S5 ODS 4.6×50 mm Ballistic; Gradient time: 4 min; Flow rate=4 ml/min; Solvent A=10% MeOH, 90% Water, 0.2% $H_3PO_4$; Solvent B=90% MeOH, 10% water, 0.2% $H_3PO_4$; Start % B=0; Final % B=100. Retention time: 3.37 min. Mass spectrum $M+H^+=494.7$.

EXAMPLE 262

2-(Acetyloxy)-N-methyl-N-[2-[2-[[3-methyl-4-(5-oxazolyl)phenyl]amino]-5-oxazolyl]phenyl]acetamide

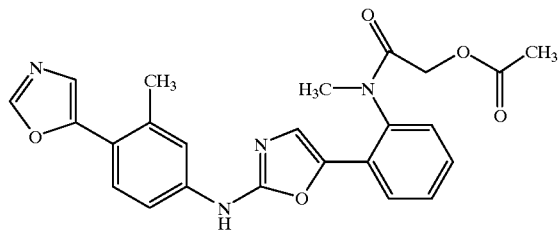

262

Example 262 Part A 5-(4-Amino-2-methylphenyl)oxazole

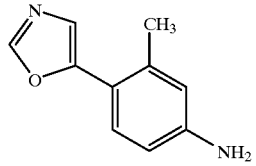

262A

2Bromo-5-nitrotoluene (1.0 g, 4.54 mmol) and vinyltributyl tin (1.59 g, 4.99 mmol) were dissolved in toluene (25 mL) under argon. Palladium dibenzylidene acetone (4.15 g, 0.455 mmol) and triphenylphosphine (488 mg, 1.86 mmol) was added and the reaction refluxed overnight. The solvent was evaporated and the residue dissolved in 200 mL of methylene chloride and washed with 10% ammonium hydroxide, water, and brine. The organic layer was dried over magnesium sulfate, filtered and concentrated. The crude product was purified by flash column chromatography heptane-methylene chlolride 1:1) to yield 726 mg of 2-methyl-4-nitrostyrene. 2-methyl-4-nitrostyrene (700 mg, 4.5 mmol) was dissolved in methylene chloride (20 mL) and cooled to −78° C., and treated with ozone until a blue color remained, after 5 minutes the excess ozone was removed by passing a stream of oxygen through the solution. Dimethyl sulfide (1 mL) was added and the reaction mixture stirred at room temperature overnight. The solvent was evaporated and the residue purified by flash column chromatography to yield 580 mg of the 2-methyl-4-nitrobenzaldehyde. 2-Methyl-4-nitrobenzaldehyde (570 mg, 3.45 mmol) and potassium carbonate (476 mg, 3.45 mmol) were suspended in methanol. Tosylmethylisocyanide (674 mg, 3.45 mmol) was added and the reaction mixture refluxed for 3 h, cooled to room temperature and concentrated. The residue was dissolved in methylene chloride (200 mL) and the organic layer was washed with water and brine. The organic layer was dried over magnesium sulfate, filtered and concentrated to yield 710 mg (94%) of 5-(4-nitro-2-methylphenyl)oxazole. 5-(4-Nitro-2-methylphenyl)oxazole was dissolved in methanol (100 mL) and 10% palladium on carbon 200 mg was wetted with water and added. The reaction mixture was hydrogenated at 45 psi overnight. The catalyst was removed by filtration and 560 mg of 5-(4-amino-2-methylphenyl)oxazole was isolated in 92% purity by HPLC method A. Mass spectrum $M+H^+=175.1$, $^1H$ 400 MHz NMR ($CDCl_3$): δ7.88 (s, 1H), 7.45 (m, 1H), 7.08 (s, 1H), 6.60 m(m, 2H), 2.38 (s, 3H).

Example 262 Part B 2-(Acetyloxy)-N-methyl-N-[2-[2-[[3-methyl-4-(5-oxazolyl)phenyl]amino]-5-oxazolyl]phenyl]acetamide The aniline 262A was converted to the isothiocyanate in a similar manner to that described in example 1 part E. The isothiocyanate was reacted with azide 257A in a manner similar to that described for example 79 part F to provide the title compound. HPLC: Column: YMC S5 ODS 4.6×50 mm Ballistic; Gradient time: 4 min; Flow rate=4 ml/min; Solvent A=10% MeOH, 90% Water, 0.2% $H_3PO_4$; Solvent B=90% MeOH, 10% water, 0.2% $H_3PO_4$; Start % B=0; Final % B=100. Retention time: 3.88 min. Mass spectrum $M+H^+=447.4$.

EXAMPLE 263

2-Hydroxy-N-[2-[2-[[3-methyl-4-(5-oxazolyl)phenyl]amino]-5-oxazolyl]phenyl]-N-methylacetamide

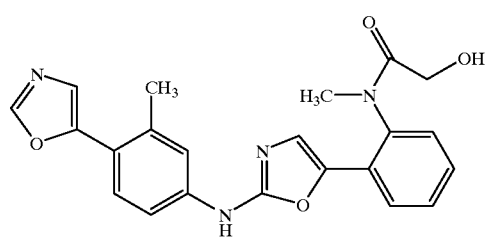

263

The product of example 262 part C was hydrolyzed with lithium hydroxide in a manner similar to that described for example 258. HPLC: Column: YMC S5 ODS 4.6×50 mm Ballistic; Gradient time: 4 min; Flow rate=4 ml/min; Solvent A=10% MeOH, 90% Water, 0.2% $H_3PO_4$; Solvent B=90% MeOH, 10% water, 0.2% $H_3PO_4$; Start % B=0; Final % B=100. Retention time: 3.07 min. Mass spectrum $M+H^+$=405.2.

EXAMPLE 264

N-Methyl-N-[2-[2-[[3-methyl-4-(5-oxazolyl)phenyl]amino]-5-oxazolyl]phenyl]-4-morpholineacetamide

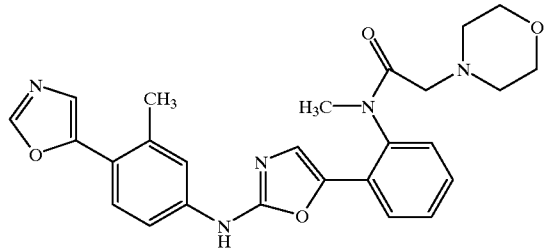

264

The aniline 262A was converted to the isothiocyanate in a similar manner to that described in example 1 part E. The isothiocyanate was reacted with the azide from example 79E in a manner similar to that described for example 257C to provide the title product. HPLC: Column: YMC S5 ODS 4.6×50 mm Ballistic; Gradient time: 4 min; Flow rate=4 ml/min; Solvent A=10% MeOH, 90% Water, 0.2% $H_3PO_4$; Solvent B=90% MeOH, 10% water, 0.2% $H_3PO_4$; Start % B=0; Final % B=100. Retention time: 3.27 min. Mass spectrum $M+H^+$=474.5.

EXAMPLE 265

N-[3-Methoxy-4-(1H-1,2,4-triazol-1-yl)phenyl]-5-phenyl-2-oxazolamine

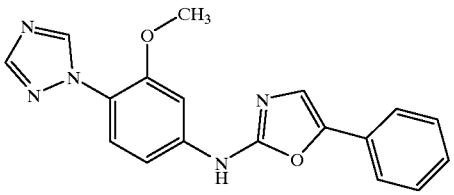

265

Example 265 Part A

3-Methoxy-4-(1H-1,2,4-triazol-1-yl)aniline

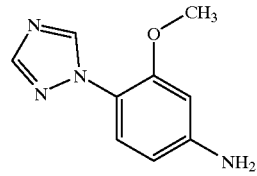

265A

2-Chloro-5-nitroanisole (0.5 g, 2.67 mmol), potassium hydroxide (219 mg, 3.92 mmol) and 1,2,4-triazole (736 mg, 10.66 mmol) were dissolved in dimethyl sulfoxide (2.5 mL), and heated at 110° C. for 24 h. The reaction mixture was poured onto ice-water (100 mL). The solid was collected by filtration and purified by flash column chromatography $CH_3Cl$ 2% methanol to yield 110 mg of 3-Methoxy-4-(1H-1,2,4-triazol-1-yl)nitrobenzene. 3-Methoxy-4-(1H-1,2,4-triazol-1-yl)nitrobenzene (105 mg, 0.48 mmol) was dissolved in methanol (10 mL) and 10% palladium on carbon (20 mg) was added. The reaction mixture was hydrogenated at 45 psi overnight. The catalyst was removed by filtration and the solvent evaporated to yield 77 mg of 265A. HPLC method A 97% pure. Mass spectrum $M+H^+$=191.1, $^1H$ 400 MHz NMR ($CH_3OD$): δ8.65 (s, 1H), 8.09 (s, 1H), 7.25 (d, 1H, J=8.56), 6.52 (d, 1H, J=2.19) 6.40–6.35 (m, 1H), 3.83 (s, 3H).

Example 265 Part B

N-[3-Methoxy-4-(1H-1,2,4-triazol-1-yl)phenyl]-5-phenyl-2-oxazolamine

The aniline 265A was converted to the isothiocyanate in a similar manner to that described in example 1 part E. The isothiocyanate was reacted with phenacyl azide in a manner similar to that described in example 34 to provide the title compound. HPLC: Column: YMC S5 ODS 4.6×50 mm Ballistic; Gradient time: 4 min; Flow rate=4 ml/min; Solvent A=10% MeOH, 90% Water, 0.2% $H_3PO_4$; Solvent B=90% MeOH, 10% water, 0.2% $H_3PO_4$; Start % B=0; Final % B=100. Retention time: 3.84 min. Mass spectrum $M+H^+$=334.2.

EXAMPLE 266

N-[4-(4-methyl-5-oxazolyl)phenyl]-5-phenyl-2-oxazolamine

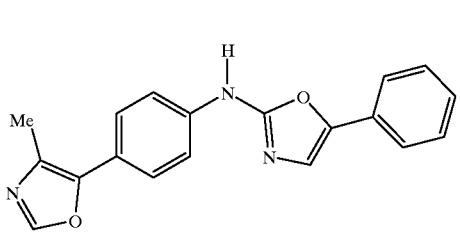

266

Example 266 Part A 4-(4-methyl-5-oxazolyl)nitrobenzene

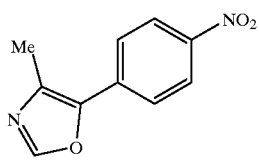

266a

A mixture of 4-nitrobenzaldehyde (0.39 g, 2.56 mmol) and 1-isocyano-1-(4-methylbenzenesulfonyl)ethane {Possel, Okko; Van Leusen, Albert M. "Chemistry of sulfonylmethyl isocyanides. 16. Tolylsulfonylmethyl isocyanide employed in a novel synthesis of ketones. A new masked formaldehyde reagent. "Tetrahedron Lett. (1977), (48), 4229–32.} (0.54 g, 2.56 mmol) in 10 mL of methanol was heated at reflux for 2 h. The solvent was removed under reduced pressure, and the resulting residue was subjected to silica gel chromatography to give 0.50 g (96%) of 266a as a white solid. The product mixture was 89% pure by analytical HPLC (retention time=3.29 min (Column: YMC S5 ODS 4.6×50 mm Ballistic; Solvent A=10% MeOH, 90% $H_2O$, 0.2% $H_3PO_4$; Solvent B=90% MeOH, 10% $H_2O$, 0.2% $H_3PO_4$). The mixture was further purified by preparative HPLC to give pure 266a (>99% by analytical HPLC). $^1$H NMR (CDCl$_3$) δ8.24 (d, 2H, J=8.1 Hz), 7.85 (s, 1H) 7.71 (d, 2H, J=8.1 Hz), 2.46 (s, 3H).

Example 266 Part B 4-(4-methyl-5-oxazolyl)aniline

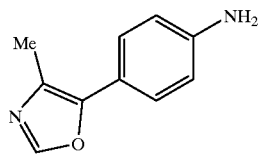

266b

A mixture of 266a (53 mg, 0.245 mmol) and catalytic palladium on carbon in 25 mL of methanol was stirred at room temperature under a hydrogen environment overnight. The mixture was filtered through a pad of Celite under reduced pressure. The filtrate was concentrated to give 43 mg (81%) of 266b as a white solid. The product was used without any further purification.

Example 266 Part C 4-(4-methyl-5-oxazolyl)phenylisothiocyanate

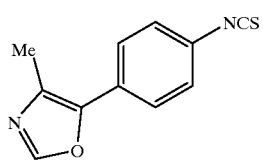

266c

A mixture of 266b and 1,1'-thiocarbonyldi-2(1H)-pyridone in 4 mL of dichloromethane was stirred at room temperature for 20 min. The solvent was removed under reduced pressure, and the residue was filtered through a pad of Celite topped with a pad of silica gel. The filtrate was concentrated to give 34 mg (64%) of 266c as a white solid.

Example 266 Part D

N-[4-(4-methyl-5-oxazolyl)phenyl]-5-phenyl-2-oxazolamine

A mixture of 266c (34 mg, 0.157 mmol), α-azidoacetophenone (38 mg, 0.236 mmol), and triphenylphosphine (62 mg, 0.236 mmol) in 2 mL of dichloromethane was stirred at room temperature for 1 h. The resulting precipitate was filtered to give 26 mg of the product as a pale yellow solid. The product was 89% pure by analytical HPLC, and was further purified by preparative HPLC to give 9.0 mg of 266 as a pale yellow solid. The product was 100% pure by analytical HPLC (retention time=4.21 min (Column: YMC S5 ODS 4.6×50 mm Ballistic; Solvent A=10% MeOH, 90% $H_2O$, 0.2% $H_3PO_4$; Solvent B=90% MeOH, 10% $H_2O$, 0.2% $H_3PO_4$) and a LC/MS $M^{+1}$=318.18.

EXAMPLE 267

N-[3-Methoxy-4-cyanophenyl]-5-phenyl-2-oxazolamine

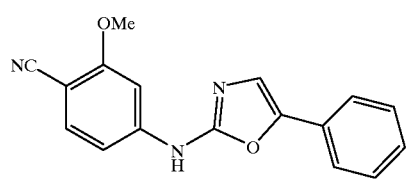

267

Example 267 Part A

2-Methoxy-4-nitrobenzonitrile

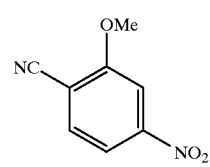

267a

Commercially available 2-Bromo-5-nitroanisole (1.0 g, 4.3 mmol), zinc cyanide (304 mg, 2.59 mmol) and palladium tetrakistriphenylphosphine (199 mg, 0.17 mmol) were added to anhydrous N,N-dimethylformamide (6 mL) and heated at 80° C. for 4h. The reaction mixture was cooled to room temperature, and diluted with 100 mL of toluene. The organic layer was washed with 2N ammonium hydroxide, water, and brine, dried over magnesium sulfate, filtered and concentrated under reduced pressure. The residue was recrystallized from ethyl acetate to yield 200 mg (26%) of the product 267a. $^1$H NMR (400 MHz) CDCl$_3$: δ8.44 (d, J=8 Hz, 1H) 7.97 (s, 1H), 7.90 (d, J=8 Hz, 1H), 4.21, (s, 3H).

Example 267 Part B

3-Methoxy-4-cyanoaniline

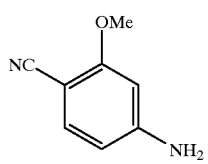

267b

Benzene derivative 267a (1.0 g, 5.62 mmol) and stannous chloride dihydrate (5.36 g, 23.7 mmol) was dissolved in a mixture of ethyl alcohol 70% (7 mL) and ethyl acetate (13 mL), and stirred at 70° C. for 0.5 h. The brown solution was poured onto ca. 100 g of crushed ice. The reaction mixture was cautiously neutralized by the portion wise addition of sodium bicarbonate. The resulting suspension was extracted with ethyl acetate, and the organic layer was washed with brine, dried over sodium sulfate, filtered and concentrated under reduced pressure. The residue was purified by flash column chromatography (methylene chloride methanol 1%) to yield 786 mg, 95% of 267b. $^1$H NMR (400 MHz) CDCl$_3$: δ7.24 (d, J=8 Hz, 1H), 6.17 (d, J=8 Hz, 1H), 6.09 (s, 1H), 3.79, (s, 3H); mass spectra m/z M+H$^+$=149.1 (100%)

N-[3-Methoxy4-cyanophenyl]-5-2-oxazolamine

The aniline 267b was converted to the isothiocyanate in a similar manner to that described in example 1 part E. The isothiocyanate was reacted with phenacyl azide in a manner similar to that described in example 34 to provide the title compound. MS+, 292. HPLC Retention Time: 4.140 min. Conditions: YMC S-5ODS-A, 4.6×50 mm column, 1%–100%B, linear gradient over 4 min at 4 ml/min; 1 min. isocratic at 100% B. Solvent A: 10% MeOH, 90%H$_2$O, 0.2% H$_3$PO$_4$; Solvent B: 90%MeOH, 10%H$_2$O, 0.2%H$_3$PO$_4$.

Although the present invention has been described in some detail by way of illustration and example for purposes of clarity and understanding, it will be apparent that certain changes and modifications may be practiced within the scope of the appended claims. All examples are illustrative of the present invention and are not to be construed as limiting the scope or embodiments of the appended claims. References cited with the specification are incorporated by reference to provide any necessary description or clarification of processes or aspects utilized in the present invention.

What is claimed is:
1. A compound having the formula,

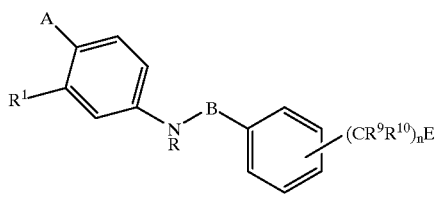

or a pharmaceutically acceptable salt thereof, wherein:

A is oxazole, thiazole, thiadiazole, oxadiazole, tetrazole, triazole, diazole, or pyrrole optionally substituted with up to three R$^5$, or cyano;

R$^1$ is hydrogen, halogen, C$_{1-4}$alkyl, C$_{1-4}$alkoxy, haloalkyl, haloalkoxy, or cyano;

R is hydrogen or C$_{1-4}$alkyl;

B is a five to six-membered unsaturated monocyclic ring selected from phenyl optionally substituted with up to four R$^{11}$ and:

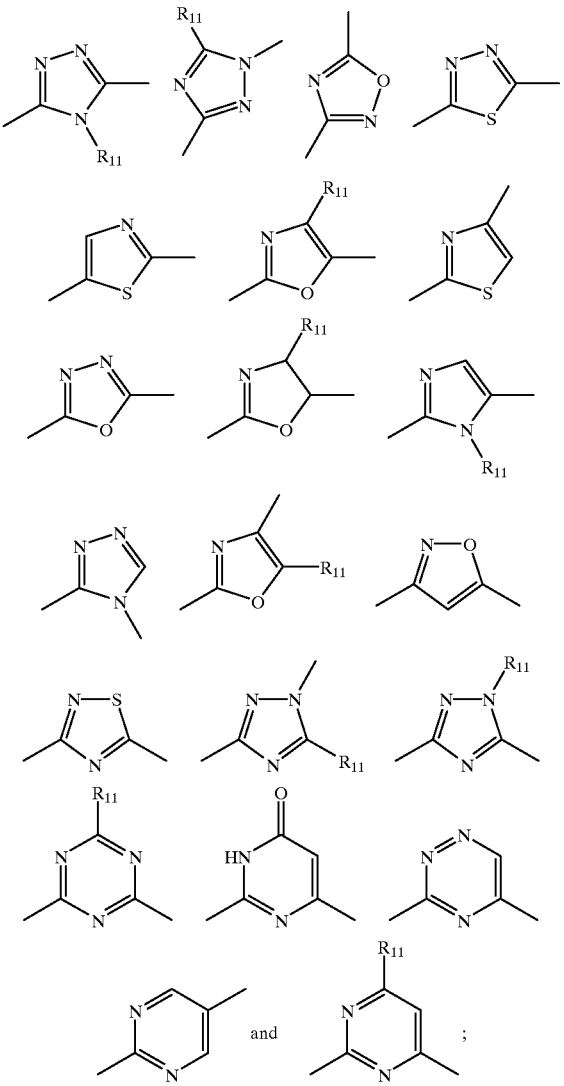

R$^9$ is hydrogen or C$_1$–C$_4$alkyl;

R$^{10}$ is hydrogen, C$_1$–C$_4$ alkyl, C$_1$–C$_4$ alkylhydroxy, C$_1$–C$_4$alkylaryl or C$_1$–C$_4$alkylheteroaryl,

137

E is selected from hydrogen, halogen, NO$^2$, C$_1$–C$_4$alkyl, C$_3$–C$_{10}$ cycloalkyl, C$_2$–C$_6$ alkenyl, C$_2$–C$_6$ alkynyl, haloalkyl, haloalkoxy, OR$^6$, CN, CO$_2$R$^6$, CONR$^6$R$^7$, OCOR$^6$, OC(=O)OR$^6$, OC(=O)NR$^6$R$^7$, OCH$_2$CO$_2$R$^6$, C(=O)R$^6$, NR$^6$R$^7$, NR$^7$C(=O)R$^6$, NR$^7$C(=O)OR$^6$, NR$^7$C(=O)C(=O)OR$^6$, NR$^7$C(=O)C(=O)NR$^6$R$^7$, NR$^7$C(=O)C(=O)(C$_1$–C$_6$alkyl), NR$^7$C(=NCN)OR$^6$, NR$^7$C(=O)NR$^6$R$^7$, NR$^7$C(=NCN)NR$^6$R$^7$, NR$^7$C(=NR$^6$)NR$^7$R$^8$, NR$^6$SO$_2$NR$^6$R$^7$, NR$^7$SO$_2$R$^6$, SR$^6$, S(=O)R$^6$, SO$_2$R$^6$, SO$_3$R$^7$, SO$_2$NR$^6$R$^7$, NHOR$^6$, NR$^6$NR$^7$NR$^8$, N(COR$^6$)OH, N(CO$_2$R$^6$)OH, CONR$^7$(CR$^9$R$^{10}$)$_r$R$^6$, CO(CR$^9$R$^{10}$)$_p$O(CHR$^9$)$_q$CO$_2$R$^6$, CO(CR$^9$CR$^{10}$)$_r$OR$^6$, CO(CR$^9$R$^{10}$)$_p$O(CR$^9$R$^{10}$)$_q$R$^6$, CO(CR$^9$CR$^{10}$)$_r$NR$^6$R$^7$, OC(O)O(CR$^9$R$^{10}$)$_m$NR$^6$R$^7$, O(CO)N(CR$^9$R$^{10}$)$_r$R$^6$, O(CR$^9$R$^{10}$)$_m$NR$^6$R$^7$, NR$^7$C(O)(CR$^9$R$^{10}$)$_r$R$^6$, NR$^7$C(O)(CR$^9$R$^{10}$)$_r$OR$^6$, NR$^7$CO(CR$^9$R$^{10}$)$_r$NR$^6$R$^7$, NR$^7$(CR$^9$R$^{10}$)$_m$OR$^6$, NR$^7$(CR$^9$R$^{10}$)$_r$CO$_2$R$^6$, NR$^7$(CR$^9$R$^{10}$)$_m$NR$^6$R$^7$, NR$^7$(CR$^9$R$^{10}$)$_n$SO$_2$(CR$^9$R$^{10}$)$_q$R$^6$, CONR$^7$(CR$^9$R$^{10}$)$_n$SO$_2$(CR$^9$R$^{10}$)$_q$R$^6$, SO$_2$NR$^7$(CR$^9$R$^{10}$)$_n$CO(CR$^9$R$^{10}$)$_q$R$^6$, SO$_2$NR$^6$(CR$^9$R$^{10}$)$_m$OR$^6$, C$_2$–C$_6$ alkenyl, C$_3$–C$_{10}$ cycloalkyl, C$_3$–C$_{10}$ cycloalkylmethyl, aryl, heterocyclic and alkylaryl;

R$^5$ independently of each other R$^5$ is selected from hydrogen and C$_{1-4}$alkyl;

R$^{11}$ is selected from hydrogen, halogen, NO$_2$, C$_1$–C$_4$alkyl, C$_3$–C$_{10}$ cycloalkyl, C$_2$–C$_6$alkenyl, C$_2$–C$_6$alkynyl, haloalkyl, haloalkoxy, OR$^6$, O(CR$^9$R$^{10}$)$_r$CO$_2$R$^6$, O(CR$^9$R$^{10}$)$_m$NR$^6$R$^7$, O(CR$^9$R$^{10}$)$_p$CN, O(CR$^9$R$^{10}$)$_r$C(=O)NR$^6$R$^7$, C$_{1-4}$alkylcarbonyl, CN, NR$^6$R$^7$, NR$^7$(CR$^9$R$^{10}$)$_r$CO$_2$R$^6$, NR$^7$OR$^6$, NR$^7$(CR$^9$R$^{10}$)$_m$OR$^6$, NR$^7$CH[(CR$^9$R$^{10}$)$_p$OR$^6$]$_2$, NR$^7$C[(CR$^9$R$^{10}$)$_p$OR$^6$]$_3$, NR$^7$C(=O)R$^6$, NR$^7$(CR$^9$R$^{10}$)$_m$OR$^6$, NR$^7$(CR$^9$R$^{10}$)$_m$NR$^6$R$^7$, NR$^7$(CR$^9$R$^{10}$)$_m$SO$_2$(CR$^9$R$^{10}$)$_q$R$^6$, SR$^7$, S(O)R$^7$, SO$_2$R$^7$, SO$_2$NR$^6$, SO$_3$R$^7$, CO$_2$R$^6$, and CONR$^6$R$^7$;

R$^6$, R$^7$ and R$^8$ are each independently selected from hydrogen, C$_1$–C$_6$alkyl, C$_3$–C$_{10}$ cycloalkyl, C$_2$–C$_6$alkenyl, C$_2$–C$_6$alkynyl, C$_1$–C$_6$ alkylcarbonyl, C$_3$–C$_7$ cycloalkyl(C$_0$–C$_5$ alkyl)carbonyl, C$_1$–C$_6$ alkoxycarbonyl, aryl(C$_0$–C$_5$ alkyl)carbonyl, aryl(C$_1$–C$_5$ alkyloxy)carbonyl, heterocyclic(C$_0$–C$_5$ alkyl)carbonyl, heterocyclic(C$_1$–C$_5$ alkoxy)carbonyl, C$_1$–C$_6$alkylsulfonyl, aryllsulfonyl, heteroarylsulfonyl, C$_0$–C$_4$alkylaryl, C$_0$–C$_4$alkylheterocyclic, wherein said cycloalkyl, aryl or heterocyclic groups are substituted with 0–2 substituents independently selected from the group consisting of C$_1$–C$_4$alkyl, hydroxy, C$_1$–C$_4$ alkoxy, F, Cl, Br, haloalkyl, NO$_2$ and CN;

or, alternatively, R$^6$ and R$^7$, or R$^6$ and R$^8$, or R$^7$ and R$^8$, when both substituents are on the same nitrogen atom [as in (—NR$^6$R$^7$) or (—NR$^7$R$^8$)], can be taken together with the nitrogen atom to which they are attached to form a heterocycle selected from 1-aziridinyl, 1-azetidinyl, 1-piperidinyl, 1-morpholinyl, 1-pyrrolidinyl, thiamorpholinyl, thiazolidinyl, 1-piperazinyl, 1-imidazolyl, 3-azabicyclo[3,2,2]nonan-3-yl, and 1-tetrazolyl, said heterocycle being optionally substituted with 0–3 groups selected from oxo, C$_0$–C$_4$alkylOH, C$_0$–C$_4$alkylOC$_1$–C$_4$alkyl, C$_0$–C$_4$alkylCONH$_2$, C$_0$–C$_4$alkylCO$_2$C$_0$–C$_4$alkyl, C$_1$–C$_6$ alkyl, C$_1$–C$_4$ alkoxy, C$_3$–C$_7$ cycloalkyl, —C$_0$–C$_6$ alkylcarbonyl, C$_3$–C$_7$ cycloalkylcarbonyl, C$_1$–C$_6$ alkoxycarbonyl, C$_3$–C$_7$ cycloalkoxycarbonyl, —NHCOalkyl, aryl, heteroaryl, aryl alkoxycarbonyl, heteroaryl alkoxycarbonyl, C$_1$–C$_6$ alkylsulfonyl, arylsulfonyl and heteroarylsulfonyl;

138 n is an integer having a value from 0–4;
m is an integer having a value from 2–6;
p is an integer having a value from 1–3;
q is an integer having a value from 0–3; and
r is an integer having a value from 0–6.

2. The compound of claim 1, or a pharmaceutically acceptable salt thereof; wherein A is cyano or

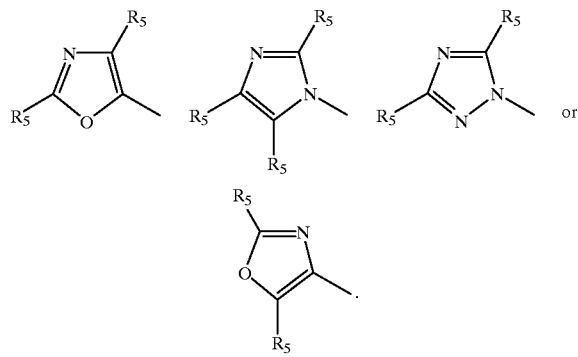

3. The compound of claim 1, or a pharmaceutically acceptable salt thereof, wherein:

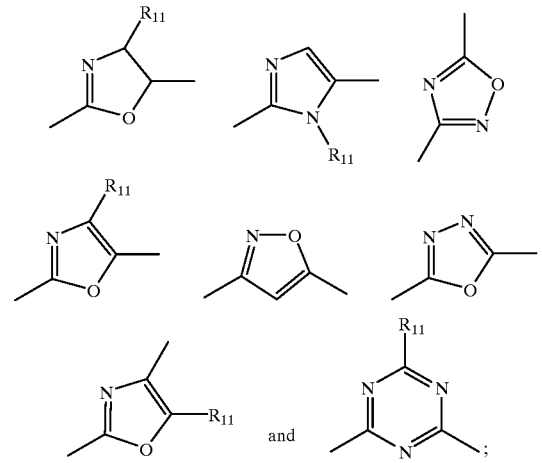

A is cyano,
R$^1$ is hydrogen, halogen, C$_1$–C$_4$alkyl, C$_1$–C$_4$alkoxy, haloalkyl, haloalkoxy, or cyano;
B is selected from phenyl and:

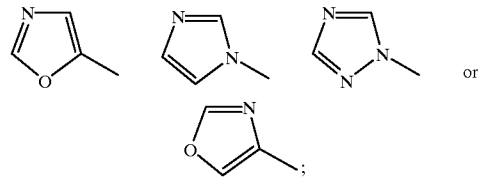

R$^9$ and R$^{10}$ are selected from hydrogen and C$_1$–C$_4$ alkyl;
E is selected from hydrogen, halogen, NO$_2$, C$_1$–C$_4$alkyl, C$_3$–C$_{10}$ cycloalkyl, C$_2$–C$_6$ alkenyl, C$_2$–C$_6$ alkynyl, haloalkyl, haloalkoxy, OR$^6$, CN, CO$_2$R$^6$, CONR$^6$R$^7$, OCH$_2$CO$_2$R$^6$, C(=O)R$^6$, NR$^6$R$^7$, NR$^7$C(=O)R$^6$, NR$^7$C(=O)C(=O)NR$^6$R$^7$, NR$^7$C(=O)C(=O)(C$_1$–C$_6$alkyl), NR$^7$C(=O)NR$^6$R$^7$, NR$^6$SO$_2$NR$^6$R$^7$, $NR^7SO_2R^6$, $NHOR^6$, $N(COR^6)OH$, $N(CO_2R^6)OH$, $NR^7C(O)(CR^9R^{10})_rR^6$, $NR^7C(O)(CR^9R^{10})_rOR^6$, $NR^7CO(CR^9R^{10})_rNR^6R^7$, $NR^7(CR^9R^{10})_mOR^6$, $NR^7(CR^9R^{10})_rCO_2R^6$, $NR^7(CR^9R^{10})_mNR^6R^7$, $C_2-C_6$ alkenyl, $C_3-C_{10}$ cycloalkyl, $C_3-C_{10}$ cycloalkylmethyl, aryl, heterocyclic and $C_1-C_4$alkylaryl;

$R^{11}$ is selected from hydrogen, halogen, $NO_2$, $C_1-C_4$alkyl, $C_3-C_{10}$ cycloalkyl, haloalkyl, haloalkoxy, $OR^6$, CN, $NR^6R^7$, $NR^7(CR^9R^{10})_rCO_2R^6$, $NR^7OR^6$, $NR^7(CR^9R^{10})_mOR^6$, $NR^7CH[(CR^9R^{10})_rOR^6]_2$, $NR^7C(=O)R^6$, $NR^7(CR^9R^{10})_mOR^6$, $NR^7(CR^9R^{10})_mNR^6R^7$, $NR^7(CR^9R^{10})_mSO_2(CR^9R^{10})_qR^6$, $CO_2R^6$, and $CONR^6R^7$; and $R^6$ and $R^7$ are each independently selected from hydrogen, $C_1-C_6$alkyl, $C_3-C_{10}$ cycloalkyl, $C_2-C_6$alkenyl, $C_2-C_6$alkynyl, $C_1-C_6$ alkylcarbonyl, $C_3-C_7$ cycloalkyl($C_0-C_5$ alkyl)carbonyl, $C_1-C_6$ alkoxycarbonyl, aryl($C_0-C_5$ alkyl)carbonyl, aryl ($C_1-C_5$ alkyloxy)carbonyl, heterocyclic($C_0-C_5$ alkyl)carbonyl, heterocyclic($C_1-C_5$ alkoxy)carbonyl, $C_1-C_6$alkylsulfonyl, arylsulfonyl, heteroarylsulfonyl, $C_0-C_4$alkylaryl, $C_0-C_4$alkylheterocyclic, wherein said cycloalkyl, aryl or heterocyclic groups are substituted with 0–2 substituents independently selected from the group consisting of $C_1-C_4$alkyl, hydroxy, $C_1-C_4$ alkoxy, F, Cl, Br, haloalkyl, $NO_2$ and CN;

or, alternatively, $R^6$ and $R^7$ can be taken together with the nitrogen atom to which they are attached to form a heterocycle selected from 1-aziridinyl, 1-azetidinyl, 1-piperidinyl, 1-morpholinyl, 1-pyrrolidinyl, thiamorpholinyl, thiazolidinyl, 1-piperazinyl, 1-imidazolyl, 3-azabicyclo[3,2,2]nonan-3-yl, and 1-tetrazolyl, said heterocycle being optionally substituted with 0–3 groups selected from $C_0-C_4$alkylOH, $C_0-C_4$alkylOC$_1-C_4$alkyl, $C_0-C_4$alkylCONH$_2$, $C_0-C_4$alkylCO$_2C_0-C_4$alkyl, and $C_1-C_6$ alkyl.

4. The compound of claim 1, or a pharmaceutically-acceptable salt thereof, in which $R^1$ is halogen, $C_1-C_4$alkyl, $C_1-C_4$alkoxy, or cyano.

5. The compound of claim 1, or a pharmaceutically-acceptable salt thereof, in which $R^9$ and $R^{10}$ are selected from hydrogen and $C_1-C_4$alkyl; and E is $NR^7CO(CR^9R^{10})_rNR^6R^7$.

6. The compound of claim 1, or a pharmaceutically-acceptable salt thereof, having the formula:

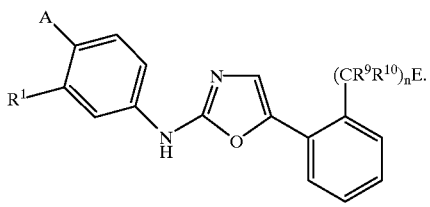

7. The compound of claim 6, or a pharmaceutically-acceptable salt thereof, in which A is cyano or

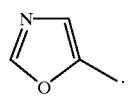

8. The compound of claim 6, or a pharmaceutically-acceptable salt thereof, in which E is $NHCO(CH_2)_rNR^6R^7$ or $N(C_1-C_4alkyl)CO(CH_2)_rNR^6R^7$; and $R^6$ and $R^7$ are each independently selected from hydrogen, $C_1-C_6$alkyl, $C_3-C_{10}$cycloalkyl, $C_1-C_6$ alkylcarbonyl, $C_1-C_6$ alkoxycarbonyl, aryl($C_0-C_5$ alkyl)carbonyl, heterocyclic($C_0-C_5$ alkyl)carbonyl, heterocyclic($C_1-C_5$ alkoxy)carbonyl, $C_0-C_4$alkylaryl, and $C_0-C_4$alkylheterocyclic, wherein said cycloalkyl, aryl or heterocyclic groups are substituted with 0–2 substituents independently selected from $C_1-C_4$alkyl, hydroxy, $C_1-C_4$ alkoxy, F, Cl, Br, haloalkyl, $NO_2$ and CN;

or, alternatively, $R^6$ and $R^7$ are taken together with the nitrogen atom to which they are attached to form a heterocycle selected from 1-aziridinyl, 1-azetidinyl, 1-piperidinyl, 1-morpholinyl, 1-pyrrolidinyl, thiamorpholinyl, thiazolidinyl, 1-piperazinyl, 1-imidazolyl, 3-azabicyclo[3,2,2]nonan-3-yl, and 1-tetrazolyl, said heterocycle being optionally substituted with 0–3 groups selected from oxo, $C_0-C_4$alkylOH, and $C_0-C_4$alkylOC$_1-C_4$alkyl.

9. The compound of claim 1, or a pharmaceutically-acceptable salt thereof, having the formula:

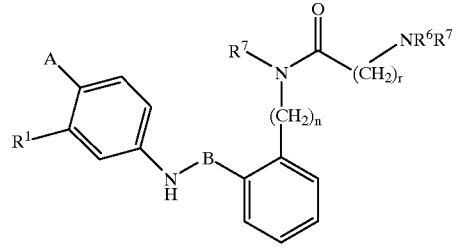

in which n and r are integers independently selected from 0 to 2.

10. A compound of claim 1 selected from (i) the group consisting of:

$N^3$-[3-Methoxy-4(5-oxazolyl)phenyl]-1-phenyl-1H-1,2,4-triazole-3,5-diamine;

$N^3$-[3-Methoxy-4(5-oxazolyl)phenyl]-1-(2-methylphenyl)-1H-1,2,4-triazole-3,5-diamine;

$N^3$-[3-Methoxy-4-(5-oxazolyl)phenyl]-1-(3-methylphenyl)-1H-1,2,4-triazole-3,5-diamine;

1-(4-Aminophenyl)-$N^3$-[3-methoxy-4-(5-oxazolyl)phenyl]-1H-1,2,4-triazole-3,5-diamine;

1-(3-Aminophenyl)-$N^3$-[3-methoxy-4-(5-axazolyl)phenyl]-1H-1,2,4-triazole-3,5-diamine;

1-(3-Fluorophenyl)-$N^3$-[3-methoxy-4-(5-oxazolyl)phenyl]-1H-1,2,4-triazole-3,5-diamine;

$N^3$-[5-Amino-3-[[3-methoxy-4-(5-oxazolyl)phenyl]amino]-1H-1,2,4-triazol-1-yl]benzonitrile;

$N^3$-[3-Methoxy-4-(5oxazolyl)phenyl]-1-(3-methoxyphenyl)-1H-1,2,4-triazole-3,5-diamine;

$N^3$-[3-Methoxy-(5axazolyl)phenyl]-1-[4-(methylsulfonyl)phenyl]-1H-1,2,4-triazole-3,5-diamine;

N-[3-Methoxy-4-(5-oxazolyl)phenyl]-5-phenyl-1H-1,2,4-triazol-3-amine;

N-[3-Methoxy-4-(5-oxazolyl)phenyl]-5-phenyl-1,3,4-oxadiazol-2-amine;

N-[3-Methoxy-4-(5-oxazolyl)phenyl]-5-phenyl-1,3,4-thiadiazol-2-amine;

N-[3-Methoxy-4-(5-oxazolyl)phenyl]-5-phenyl-2-oxazolamine;

N-[3-Methoxy-4-(5-oxazolyl)phenyl]-4-methyl-5-phenyl-2-oxazolamine;

N-[3-Methoxy-4-(5-oxazolyl)phenyl]-5-(2-methoxyphenyl)-2-oxazolamine;
N-[3-Methoxy-4-(5-oxazolyl)phenyl]-5-(4-methylphenyl)-2-oxazolamine;
N-[3-Methoxy-4-(5-oxazolyl)phenyl]-5-(3-methylphenyl)-2-oxazolamine;
N-[3-Methoxy-4-(5-oxazolyl)phenyl]-5-(2-methylphenyl)-2-oxazolamine;
4-Ethyl-N-[3-methoxy-4-(5-oxazolyl)phenyl]-5-phenyl-2-oxazolamine;
N-[2-[2-[[3-Methoxy-4-(5-oxazolyl)phenyl]amino]-5-oxazolyl]phenyl]-N-acetamide;
N-[2-[2-[[3-Methoxy-4-(5-oxazolyl)phenyl]amino]-5-oxazolyl]phenyl]-N-methylacetamide;
N-[3-Methoxy-4-(5-oxazolyl)phenyl)-5-methyl-4-phenyl-2-oxazolamine;
2-Methoxy-N-[2-[2-[[3-methoxy-4-(5-oxazolyl)phenyl]amino]-5-oxazolyl]phenyl]acetamide;
N-[2-[2-[[3-Methoxy-4-(5-oxazolyl)phenyl]amino]-5-oxazolyl]phenyl]-4-morpholineacetamide;
2-Methoxy-N-[2-[2-[[3-methoxy-4-(5-oxazolyl)phenyl]amino]-5-oxazolyl]phenyl]-N-methylacetamide;
2-Methoxy-N-[2-[2-[[3-methoxy-4-(5-oxazolyl)phenyl]amino]-5-oxazolyl]phenyl]-N-methylacetamide;
[2-[2-[[3-Methoxy-4-(5-oxazolyl)phenyl]amino]-5-oxazolyl]phenyl]carbamic acid tetrahydro-3-furanyl ester;
[2-[2-[[3-Methoxy-4-(5-oxazolyl)phenyl]amino]-5-oxazolyl]phenyl]methylcarbamic acid tetrahydro-3-furanyl ester;
[2-[2-[[3-Methoxy-4-(5-oxazolyl)phenyl]amino]-5-oxazolyl]phenyl]methylcarbamic acid phenylmethyl ester;
2-[2-[[3-Methoxy-4-(5-oxazolyl)phenyl]amino]-5-oxazolyl]-N,N-dimethylbenzamide;
N-[2-[2-[[3-Methoxy-4-(5-oxazolyl)phenyl]amino]-5-oxazolyl]phenyl]-N-methyl-4-morpholinepropanamide,
N-[2-[2-[[3-Methoxy-4-(5-oxazolyl)phenyl]amino]-5-oxazolyl]phenyl]-N,$N^2$,$N^2$-trimethylglycinamide;
N-[2-[2-[[3-Methoxy-4-(5-oxazolyl)phenyl]amino]-5-oxazolyl]phenyl]-N,N2-dimethylglycinamide;
N-[2-[2-[[3-Methoxy-4-(5-oxazolyl)phenyl]amino]-5-oxazolyl]phenyl]-N,4-dimethyl-1-piperazineacetamide;
N-[2-[2-[[3-Methoxy-4-(5-oxazolyl)phenyl]amino]-5-oxazolyl]phenyl]-N-methyl-1H-1,2,4-triazole-1-acetamide;
$N^2$-(1,1-Dimethylethyl)-N-[2-[2-[[3-methoxy-4-(5-oxazolyl)phenyl]amino]-5-oxazolyl]phenyl]-N-methylglycinamide;
N-[2-[2-[[3-Methoxy-4-(5-oxazolyl)phenyl]amino]-5-oxazolyl]phenyl]-N-methyl-N2-(1-methylethyl)glycinamide;
N-[2-[2-[[3-Methoxy-4-(5-oxazolyl)phenyl]amino]-5-oxazolyl]phenyl]-N-methyl-1H-imidazole-1-acetamide;
N-[2-[2-[[3-Methoxy-4-(5-oxazolyl)phenyl]amino]-5-oxazolyl]phenyl]-N-methyl-1H-pyrazole-1-acetamide;
N-[2-[2-[[3-Methoxy-4-(5-oxazolyl)phenyl]amino]-5-oxazolyl]phenyl]-N-methyl-2H-1,2,3-triazole-2-acetamide;
N-[2-[2-[[3-Methoxy-4-(5-oxazolyl)phenyl]amino]-5oxazolyl]phenyl]-N-methyl-1H-1,2,3-triazole-1-acetamide;
N-[2-[2-[[3-Methoxy-4-(5-oxazolyl)phenyl]amino]-5-oxazolyl]phenyl]-N,α-dimethyl-4-morpholineacetamide;
N-[2-[2-[[3-Methoxy-4-(5-oxazolyl)phenyl]amino]-5-oxazolyl]phenyl]-N-methyl-2-pyrrolidinecarboxamide;
N-[2-[2-[[3-Methoxy-4-(5-oxazolyl)phenyl]amino]-5-oxazolyl]phenyl]-N-methyl-4-morpholineacetamide;
N-[3-Methoxy-4-(5-oxazolyl)phenyl]-5-(3-nitrophenyl)-2-oxazolamine;
2-[2-[[3-Methoxy-4-(5-oxazolyl)phenyl]amino]-5-oxazolyl]-N-methylbenzamide;
(S)-2-[2-[[3-Methoxy-4-(5-oxazolyl)phenyl]amino]-5-oxazolyl]-N-(tetrahydro-3-furanyl)benzamide;
1-[[2-[2-[[3-Methoxy-4-(5-oxazolyl)phenyl]amino]-5-oxazolyl]phenyl]carbonyl]-4-methylpiperazine;
2-[2-[[3-Methoxy-4-(5-oxazolyl)phenyl]amino]-5-oxazolyl]-N-[2-(4-morpholinyl)ethyl]benzamide;
2-[2-[[3-Methoxy-4-(5-oxazolyl)phenyl]amino]-5-oxazolyl]-1-pyrrolidinecarboxylic acid ethyl ester;
4-Methoxy-N-[3-methoxy-4-(5-oxazolyl)phenyl]-6-phenyl-1,3,5-triazin-2-amine;
N-[3-Methoxy-4-(5-oxazolyl)phenyl]-4-(4-phenyl-1-piperazinyl)-6-phenyl-1,3,5-triazin-2-amine;
N-[3-Methoxy-4-(5-oxazolyl)phenyl]-4-(4-morpholinyl)-6-phenyl-1,3,5-triazin-2-amine;
N-[3-Methoxy-4-(5-oxazolyl)phenyl]-6-phenyl-N'-(phenylmethyl)-1,3,5-triazine-2,4-diamine;
N-[3-Methoxy-4-(5-oxazolyl)phenyl]-4-(4-methyl-1-piperazinyl)-6-phenyl-1,3,5-triazin-2-amine;
N-[3-Methoxy-4-(5-oxazolyl)phenyl]-6-phenyl-N'-(3-pyridylmethyl)-1,3,5-triazine-2,4-diamine;
N-[3-Methoxy-4-(5-oxazolyl)phenyl]-N'-[(5-methyl-2-furanyl)methyl]-6-phenyl-1,3,5-triazine-2,4-diamine;
N-[3-Methoxy-4-(5-oxazolyl)phenyl]-6-phenyl-N'-[2-(3-pyridinyl)ethyl]-1,3,5-triazine-2,4-diamine;
N-[3-Methoxy-4-(5-oxazolyl)phenyl]-6-phenyl-N'-[(tetrahydro-2-furanyl)methyl]-1,3,5-triazine-2,4-diamine;
N-[3-(1H-Imidazol-1-yl)propyl]-N'-[3-methoxy-4-(5-oxazolyl)phenyl]-6-phenyl-1,3,5-triazine-2,4-diamine;
N-[3-Methoxy-4-(5-oxazolyl)phenyl]-6-phenyl-N'-[2-(4-pyridinyl)ethyl]-1,3,5-triazine-2,4-diamine;
4-[[4-[[3-Methoxy-4-(5-oxazolyl)phenyl]amino]-6-phenyl-1,3,5-triazin-2-yl]amino]-1-butanol;
N-[3-Methoxy-4-(5-oxazolyl)phenyl]-6-phenyl-N'-(2-pyridinylmethyl)-1,3,5-triazine-2,4-diamine,
N-[2-[[4-[[3-Methoxy-4-(5-oxazolyl)phenyl]amino]-6-phenyl-1,3,5-triazin-2-yl]amino]ethyl]acetamide;
N-[3-Methoxy-4-(5-oxazolyl)phenyl]-N'-methylbutyl)-6-phenyl-1,3,5-triazine-2,4-diamine;
N-[3-Methoxy-4-(5-oxazolyl)phenyl]-6-phenyl-1,3,5-triazine-2,4-diamine;
N-Methoxy-N'-[3-methoxy-4-(5-oxazolyl)phenyl]-6-phenyl-1,3,5-triazine-2,4-diamine;
N-Butyl-N'-[3-methoxy-4-(5-oxazolyl)phenyl]-6-phenyl-1,3,5-triazine-2,4-diamine;
N-[2-(1H-Imidazol-4-yl)ethyl]-N'-[3-methoxy-4-(5-oxazolyl)phenyl]-6-phenyl-1,3,5-triazine-2,4-diamine;
N-(2-Furanylmethyl)-N'-[3-methoxy-4-(5-oxazolyl)phenyl]-6-phenyl-1,3,5-triazine-2,4-diamine;
2-[[4-[[3-Methoxy-4-(5-oxazolyl)phenyl]amino]-6-phenyl-1,3,5-triazin-2-yl]propylamino]ethanol;
N-[3-Methoxy-4-(5-oxazolyl)phenyl]-6-phenyl-N'-(4-pyridinylmethyl)-1,3,5-triazine-2,4-diamine;
(S)-1-[4-[[3-Methoxy-4-(5-oxazolyl)phenyl]amino]-6-phenyl-1,3,5-triazin-2-yl]-2-pyrrolidinemethanol;
4-[4-[[3-Methoxy-4-(5-oxazolyl)phenyl]amino]-6-phenyl-1,3,5-triazin-2-yl]-1-piperazinecarboxaldehyde;
1-[4-[[3-Methoxy-4-(5-oxazolyl)phenyl]amino]-6-phenyl-1,3,5-triazin-2-yl]-4-piperidineethanol;
N-[2-(Dimethylamino)ethyl]-N-ethyl-N'-[3-methoxy-4-(5-oxazolyl)phenyl]-6-phenyl-1,3,5-triazine-2,4-diamine;
'1-[4-[[3-Methoxy-4-(5-oxazolyl)phenyl]amino]-6-phenyl-1,3,5-triazin-2-yl]-1-piperidineethanol;

1-[4-[[3-Methoxy-4-(5-oxazolyl)phenyl]amino]-6-phenyl-1,3,5-triazin-2-yl]-4-piperidinol;
N-[1-[4-[[3-Methoxy-4-(5-oxazolyl)phenyl]amino]-6-phenyl-1,3,5-triazin-2-yl]-3-pyrrolidinyl]acetamide;
2-[[4-[[3-Methoxy-4-(5-oxazolyl)phenyl]amino]-6-phenyl-1,3,5-triazin-2-yl](phenylmethyl)amino]ethanol;
1-[4-[[3-Methoxy-4-(5-oxazolyl)phenyl]amino]-6-phenyl-1,3,5-triazin-2-yl]-L-prolinamide;
1-[4-[[3-Methoxy-4-(5-oxazolyl)phenyl]amino]-6-phenyl-1,3,5-triazin-2-yl]-3-pyrrolidinol;
(S)-4-[2-(Methoxymethyl)-1-pyrrolidinyl]-N-[3-methoxy-4-(5-oxazolyl)phenyl]-6-phenyl-1,3,5-triazin-2-amine;
4-[[4-[[3-Methoxy-4-(5-oxazolyl)phenyl]amino]-6-phenyl-1,3,5-triazin-2-yl]amino]butanoic acid;
N-[3-Methoxy-4-(5-oxazolyl)phenyl]-4-phenyl-6-[(tetrahydro-3-furanyl)oxy]-1,3,5-triazin-2-amine;
1-[[4-[[3-Methoxy-4-(5-oxazolyl)phenyl]amino]-6-phenyl-1,3,5-triazin-2-yl]oxy]-2-propanol;
2-[[4-[[3-Methoxy-4-(5-oxazolyl)phenyl]amino]-6-phenyl-1,3,5-triazin-2-yl]amino]-1,3-propanediol;
2-[[3-Methoxy-4-(5-oxazolyl)phenyl]amino]-6-phenyl-4(3H)-triazinone;
N-[2-[2-[[3-Methoxy-4-(5-oxazolyl)phenyl]amino]-5-oxazolyl]phenyl]-N-methyl-1-piperidineacetamide;
(S)-2-(Methoxymethyl)-N-[2-[2-[[3-methoxyl-4-(5-oxazolyl)phenyl]amino]-5-oxazolyl]phenyl]-N-methyl-1-pyrrolidineacetamide;
2-Amino-N-[2-[2-[[3-methoxy-4-(5-oxazolyl)phenyl]amino]-5-oxazolyl]phenyl]-N-methylacetamide;
N-[2-[2-[[3-Methoxy-4-(5-oxazolyl)phenyl]amino]-5-oxazolyl]phenyl]-N,2-dimethylpropanamide;
N-[2-[2-[[3-Bromo-4-(5-oxazolyl)phenyl]amino]-5-oxazolyl]phenyl]-N-methyl-4-morpholineacetamide;
N-[2-[2-[[3-Chloro-4-(5-oxazolyl)phenyl]amino]-5-oxazolyl]phenyl]-N-methyl-4-morpholineacetamide;
2-Hydroxy-N-[2-[2-[[3-methyl-4-(5-oxazolyl)phenyl]amino]-5-oxazolyl]phenyl]-N-methylacetamide;
N-Methyl-N-[2-[2-[[3-methyl-4-(5-oxazolyl)phenyl]amino]-5-oxazolyl]phenyl]-4-morpholineacetamide;
N-[3-Methoxy-4-(1H-1,2,4-triazol-1-yl)phenyl]-5-phenyl-2-oxazolamine; and
N-[3-Methoxy-4-cyanophenyl]-5-phenyl-2-oxazolamine;
and (ii) a pharmaceutically-acceptable salt thereof.

11. A compound having the formula:

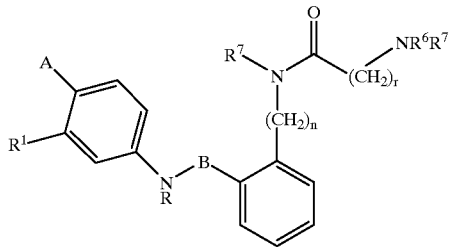

or a pharmaceutically-acceptable salt thereof, in which:
A is oxazole, thiazole, thiadiazole, oxadiazole, tetrazole, triazole, diazole, or pyrrole optionally substituted with up to three $R^5$, or cyano;
$R^1$ is hydrogen, halogen, $C_{1-4}$alkyl, $C_{1-4}$alkoxy, haloalkyl, haloalkoxy, or cyano;
R is hydrogen or $C_{1-4}$alkyl;
B is a five to six-membered unsaturated monocyclic ring selected from phenyl optionally substituted with up to four $R^{11}$ and:

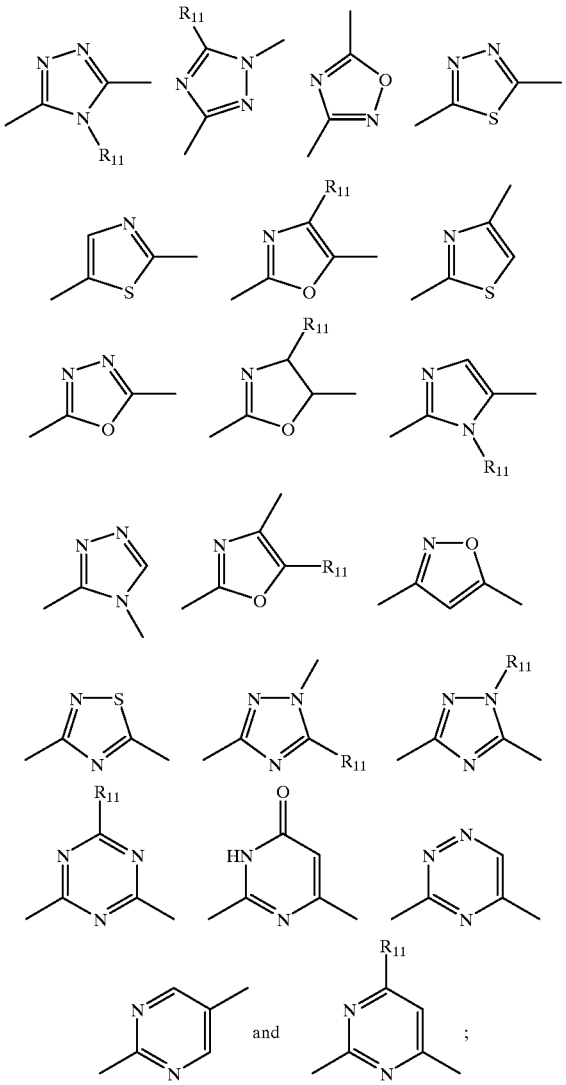

$R^5$ independently of each other $R^5$ is selected from hydrogen and $C_{1-4}$alkyl;
$R^{11}$ is selected from hydrogen, halogen, $NO_2$, $C_1$–$C_4$alkyl, $C_3$–$C_{10}$ cycloalkyl, $C_2$–$C_6$alkenyl, $C_2$–$C_6$alkynyl, haloalkyl, haloalkoxy, $OR^6$, CN, $NR^6R^7$, $SR^7$, $S(O)R^7$, $SO_2R^7$, $SO_3R^7$, $CO_2R^6$, $NR^7C(=O)R^6$ and $CONR^6R^7$;
$R^6$ and $R^7$ are each independently selected from hydrogen, $C_1$–$C_6$alkyl, $C_3$–$C_{10}$ cycloalkyl, $C_2$–$C_6$alkenyl, $C_2$–$C_6$alkynyl, $C_1$–$C_6$ alkylcarbonyl, $C_3$–$C_7$ cycloalkyl($C_0$–$C_5$ alkyl)carbonyl, $C_1$–$C_6$ alkoxycarbonyl, aryl($C_0$–$C_5$ alkyl)carbonyl, aryl ($C_1$–$C_5$ alkyloxy)carbonyl, heterocyclic($C_0$–$C_5$ alkyl) carbonyl, heterocyclic($C_1$–$C_5$ alkoxy)carbonyl, $C_1$–$C_6$alkylsulfonyl, aryllsulfonyl, heteroarylsulfonyl, $C_0$–$C_4$alkylaryl, $C_0$–$C_4$alkylheterocyclic, wherein said cycloalkyl, aryl or heterocyclic groups are substituted with 0–2 substituents independently selected from the group consisting of $C_1$–$C_4$alkyl, hydroxy, $C_1$–$C_4$ alkoxy, F, Cl, Br, haloalkyl, $NO_2$ and CN;
or, alternatively, $R^6$ and $R^7$ when both substituents are on the same nitrogen atom, can be taken together with the nitrogen atom to which they are attached to form a heterocycle selected from 1-aziridinyl, 1-azetidinyl, 1-piperidinyl, 1-morpholinyl, 1-pyrrolidinyl, thiamorpholinyl, thiazolidinyl, 1-piperazinyl, 1-imidazolyl, 3-azabicyclo[3,2,2]nonan-3-yl, and 1-tetrazolyl, said heterocycle being optionally substituted with 0–3 groups selected from oxo, $C_0$–$C_4$alkylOH, $C_0$–$C_4$alkylO$C_1$–$C_4$alkyl, $C_0$–$C_4$alkylCONH$_2$, $C_0$–$C_4$alkylCO$_2C_0$–$C_4$alkyl, $C_1$–$C_6$ alkyl, $C_1$–$C_4$ alkoxy, $C_3$–$C_7$ cycloalkyl, —$C_0$–$C_6$ alkylcarbonyl, $C_3$–$C_7$ cycloalkylcarbonyl, $C_1$–$C_6$ alkoxycarbonyl, $C_3$–$C_7$ cycloalkoxycarbonyl, —NHCOalkyl, aryl, heteroaryl, aryl alkoxycarbonyl, heteroaryl alkoxycarbonyl, $C_1$–$C_6$ alkylsulfonyl, arylsulfonyl and heteroarylsulfonyl;

n is an integer having a value from 0–4; and r is an integer having a value from 0–4.

12. The compound of claim 11, or a pharmaceutically acceptable salt thereof, in which $R^6$ and $R^7$ are each independently selected from hydrogen, $C_1$–$C_6$alkyl, $C_3$–$C_{10}$cycloalkyl, $C_1$–$C_6$ alkylcarbonyl, $C_1$–$C_6$alkoxycarbonyl, $C_0$–$C_4$alkylaryl, and $C_0$–$C_4$alkylheterocyclic, wherein said cycloalkyl, aryl or heterocyclic groups are substituted with 0–2 substituents independently selected from the group consisting of $C_1$–$C_4$alkyl, hydroxy, $C_1$–$C_4$ alkoxy, F, Cl, Br, haloalkyl, NO$_2$ and CN;

or, alternatively, $R^6$ and $R^7$ when both substituents are on the same nitrogen atom, can be taken together with the nitrogen atom to which they are attached to form a heterocycle selected from 1-aziridinyl, 1-azetidinyl, 1-piperidinyl, 1-morpholinyl, 1-pyrrolidinyl, thiamorpholinyl, thiazolidinyl, 1-piperazinyl, 1-imidazolyl, 3-azabicyclo[3,2,2]nonan-3-yl, and 1-tetrazolyl, said heterocycle being optionally substituted with 0–3 groups selected from oxo, $C_0$–$C_4$alkylOH, and $C_0$–$C_4$alkylO$C_1$–$C_4$alkyl;

n is an integer having a value from 0–2; and r is an integer having a value from 0–2.

13. The compound of claim 12, having the formula,

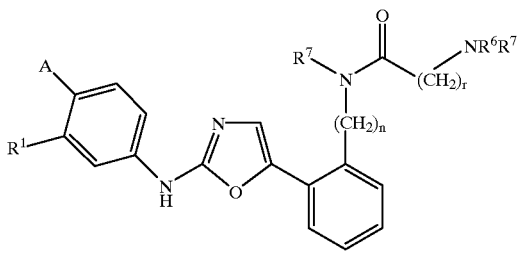

or a pharmaceutically acceptable salt thereof.

14. A pharmaceutical composition for treating an IMPDH-associated disorder, comprising a pharmaceutically acceptable carrier, adjuvant or vehicle and at least one compound of claim 1, or pharmaceutically acceptable salt thereof, in an amount effective therefor.

15. A pharmaceutical composition for treating an IMPDH-associated disorder, comprising a pharmaceutically acceptable carrier, adjuvant or vehicle and at least one compound of claim 1, or pharmaceutically acceptable salt thereof, in an amount effective therefor.

16. The pharmaceutical composition of claim 14, wherein the IMPDH-associated disorder is selected from an autoimmune disorder, an inflammatory disorder, a cancer or tumor disorder, and a DNA or RNA viral replication disease.

17. The pharmaceutical composition of claim 14, for treating an IMPDH-associated disorder wherein the IMPDH-associated disorder is selected from transplant rejection, rheumatoid arthritis, inflammatory bowel disease, asthma, and psoriasis.

18. The pharmaceutical composition of claim 14, for treating an IMPDH-associated disorder wherein the IMPDH-associated disorder is selected from restenosis, stenosis, artherosclerosis, and ischemic or reperfusion injury.

19. A pharmaceutical composition comprising (i) a pharmaceutically acceptable carrier, adjuvant or vehicle; (ii) at least one compound of claim 1, or pharmaceutically acceptable salt thereof, and (iii) one or more second compounds or compositions wherein said pharmaceutical composition is effective for treating an IMPDH-associated condition.

20. A pharmaceutical composition comprising (i) a pharmaceutically acceptable carrier, adjuvant or vehicle; (ii) at least one compound of claim 11, or pharmaceutically acceptable salt thereof, and (iii) one or more second compounds or compositions wherein said pharmaceutical composition is effective for treating an IMPDH-associated condition.

21. The pharmaceutical composition of claim 19, wherein said second compound or composition is selected from one or more of: another IMPDH inhibitor; a cyclosporin; CTLA4-Ig; an antibody selected from anti-ICAM-3, anti-IL-2 receptor (Anti-Tac), anti-CD45RB, anti-CD2, anti-CD3 (OKT-3), anti-CD4, anti-CD80, anti-CD86, and monoclonal antibody OKT3; an agent blocking the interaction between CD40 and CD154; a fusion protein constructed from CD40 and/or CD154/gp39; an inhibitor of NF-kappa B function; a non-steroidal antiinflammatory drug (NSAID); a gold compound; an antiviral agent; an antiproliferative; a cytotoxic drug; an TNF-α inhibitor; an anti-TNF antibody; a soluble TNF receptor; and rapamycin (sirolimus or Rapamune); or derivatives thereof.

22. A method for inhibiting IMPDH in a mammal, comprising the step of administering to a subject in need thereof an amount effective of at least one compound of claim 1.

23. A method for inhibiting IMPDH in a mammal, comprising the step of administering to a subject in need thereof an amount effective of at least one compound of claim 11.

24. The method of claim 23, wherein method comprises administering said pharmaceutical composition simultaneously or sequentially with one or more of: an immunosuppressant, an anti-cancer agent, an anti-viral agent, an anti-inflammatory agent, an anti-fungal agent, an antibiotic, an anti-vascular hyperproliferation compound, or a IMPDH inhibitor.

25. A method of treating a disorder selected from transplant rejection, rheumatoid arthritis, inflammatory bowel disease, asthma, and psoriasis, comprising the step of administering to a subject in need thereof an amount effective of at least one compound of claim 11.

26. A method of treating a disorder selected from restenosis, stenosis, artherosclerosis, and ischemic or reperfusion injury, comprising the step of administering to a subject in need thereof an amount effective of at least one compound of claim 11.

* * * * *